United States Patent [19]

Barker et al.

[11] Patent Number: 4,849,419
[45] Date of Patent: Jul. 18, 1989

[54] 7-OXO-4-THIA-AZABICYCLO[3,2,0]HEPT-2-ENE DERIVATIVES

[75] Inventors: Andrew J. Barker; Nicholas I. Carruthers, both of Milton Keynes; Michael D. Cooke, Newport Pagnell, all of Great Britain

[73] Assignee: Hoechst UK Limited, Hounslow Middx., United Kingdom

[21] Appl. No.: 127,542

[22] Filed: Dec. 1, 1987

Related U.S. Application Data

[63] Continuation of Ser. No. 773,657, Sep. 9, 1985, abandoned.

[30] Foreign Application Priority Data

Sep. 10, 1984 [GB] United Kingdom ................ 8422842
Nov. 16, 1984 [GB] United Kingdom ................ 8428968

[51] Int. Cl.[4] .................... C07D 499/00; A61K 31/425
[52] U.S. Cl. .................................. 514/192; 540/310; 514/195
[58] Field of Search ................. 540/310; 514/192, 195

[56] References Cited

U.S. PATENT DOCUMENTS 4,585,767 4/1986 Cooke et al. ................ 540/310

FOREIGN PATENT DOCUMENTS 2104511 3/1983 United Kingdom .

Primary Examiner—Nicholas S. Rizzo
Attorney, Agent, or Firm—Finnegan, Henderson, Farabow, Garrett & Dunner

[57] ABSTRACT

A compound of formula I

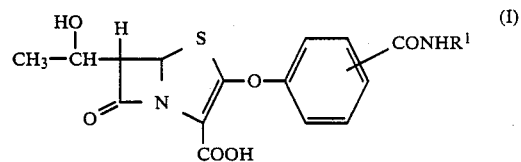

with $R^1$ being an alkyl group substituted by one or more substituents and esters thereof at the 2-carboxy group or at the 8-hydroxy group or both; and salts thereof. Compounds I have antibacterial effect. Various intermediates are described. This compound of the formula I, or an ester at the 2-carboxy group or at the 8-hydroxy group or both or a salt thereof is produced by reacting a compound of formula II or of formula IX

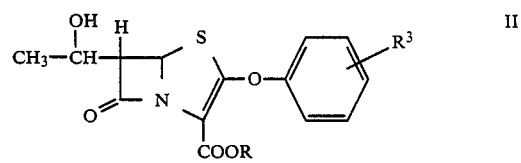

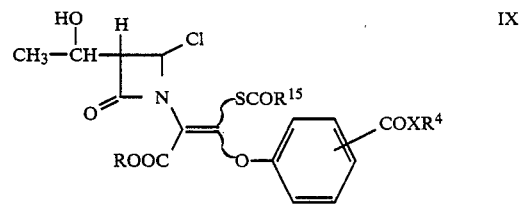

in which R represents a hydrogen atom or a carboxy protecting group, $R^3$ represents an activated carboxylic acid group, $R^4$ represents an alkyl group having 1 to 4 carbon atoms, or a phenyl group which may be unsubstituted or substituted, $R^{15}$ represents a phenyl group or an alkyl group having from 1 to 4 carbon atoms, and X represents an oxygen or sulphur with an amine of the formula III $R^1NH_2$ (III) to give a compound of formula I, or an ester thereof of formula Ia

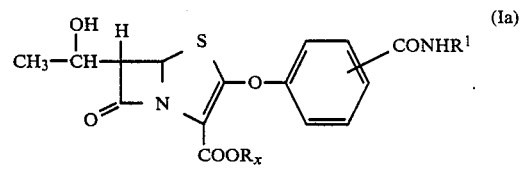

11 Claims, No Drawings

7-OXO-4-THIA-AZABICYCLO[3,2,0]HEPT-2-ENE DERIVATIVES

This application is a continuation of application Ser. No. 773,657, filed Sept. 9, 1985, now abandoned.

This invention relates to 7-oxo-4-thia-1-azabicyclo[3,2,0]hept-2-ene derivatives, to a process for their preparation, to pharmaceutical preparations comprising them, and to intermediates for use in the preparation of substances having antibacterial activity and/or $\beta$-lactamase inhibitory and/or inactivating activity.

7-Oxo-4-thia-1-azabicyclo[3,2,0]hept-2-ene has the following formula A, and derivatives thereof having an aliphatic side chain at position 6 are numbered as shown in formula B:

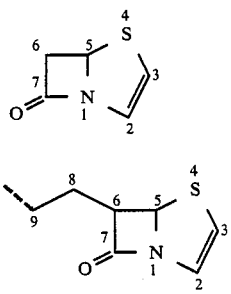

By an alternative system of nomenclature, the above nucleus A may be described as a "penem", in which case the ring numbering is as shown in formula C, with derivatives having an aliphatic side chain at position 6 being numbered as chain in formula D:

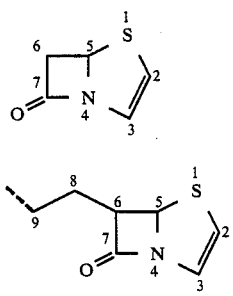

The present invention provides a compound of formula I

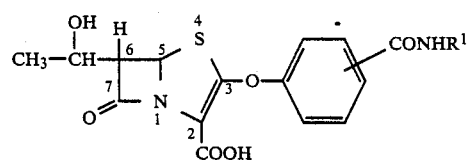

in which $R^1$ represents a straight or branched chain alkyl group having from 1 to 5 carbon atoms, for example, a methyl, ethyl, n-propyl, iso-propyl, n-butyl, iso-butyl, sec-butyl, t-butyl or n-pentyl group, which alkyl group is substituted by one or more, for example, one or two, especially one, substituent selected from
(i) unsubstituted phenyl groups;
(ii) heterocyclic groups having 5 or 6 ring members and from 1 to 3 heteroatoms, which may be the same or different, selected from nitrogen, oxygen and sulphur atoms;
(iii) —CH groups;
(iv) guanidino and formimidoylamino groups;
(v) —$OR_a^2$ and —$SR_a^2$ groups in which $R_a^2$ represents a hydrogen atom or an alkyl group having from 1 to 4 carbon atoms; especially a methyl or ethyl group;
(vi) —$COOR_b^2$ groups in which $R_b^2$ represents a hydrogen atom or a carboxy protecting group;
(vii) —$SO_2N(R_a^2)_2$ groups in which $R_a^2$ is as defined above,
(viii) —$SO_2R_c^2$ and —$SOR_c^2$ groups, in which $R_c^2$ represents an alkyl group having from 1 to 4 carbon atoms;
(ix) —$N(R_a^2)_2$ in which $R_a^2$ is as defined above;
(x) —$OCON(R_a^2)_2$ and —$NHCON(R_a^2)_2$ groups, in which $R_a^2$ is as defined above;
(xi) —$NHCOR_a^2$, and —$CONHOR_a^2$ groups, in which $R_a^2$ is as defined above;
(xii) —$NHCOOR_d^2$ and —NH—Q—$COOR_d^2$ groups in which $R_a^2$ is as defined above, $R_d^2$ represents a carboxy protecting group, and Q represents a methylene group which may be substituted by a methyl group or a phenyl group, or Q represents a straight or branched chain alkylene group having two or three carbon atoms which may be substituted by one or two substituents selected from amino, methyl and phenyl groups;
(xiii) —$CON(R_a^2)_2$ groups in which $R_a^2$ is as defined above;
(xiv) groups of the formula

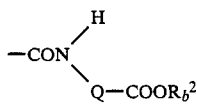

in which Q and $R_b^2$ are as defined above; and
(xv) groups of the formula

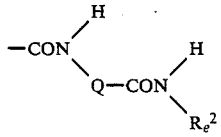

in which Q is as defined above and $R_e^2$ represents a hydrogen atoms, an alkyl group having from 1 to 4 carbon atoms or a group

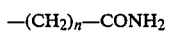

in which n represents an integer of from 1 to 4; or
$R^1$ represents an amidino group which may be unsubstituted or substituted by one, two or three groups, which may be the same or different, selected from methyl and ethyl groups.

If $R^1$ has more than one substituent, then the substituents may be the same or different. Moreover, if a substituent of $R^1$ can, itself, have more than one substituent, then these, too, may be the same or different.

The present invention also provides esters of a compound of formula I at the 2-carboxy group, for example, esters that can be converted by hydrolysis, by photolysis, by reduction or, especially, by esterase enzyme action, to give the free acid of fromula I.

The present invention further provides esters of a compound of formula I at the 8-hydroxy group. Such ester groups at the 8-position are, for example, alkanoyloxy groups having from 1 to 4 carbon atoms. Ester groups at positions 8- and 2- may be present independently.

Furthermore, in a compound of formula I, an alkyl group R¹ may be substitued by a carboxylic acid group or by a protected (esterified) caboxylic acid group either directly (see (vi) above) or as part of another substituent (see (xii) and (xiv) above). Such ester groups are as described for ester groups at the 2-position.

The hydroxyl group and the carboxylic acid group(s) may be esterified independently, but in general if two carboxylic acid groups are present, these are both in the same state, ie both free or both esterified, and the 8-hydroxy group is esterified independently.

The present invention further provides salts of a compound of formula I, especially physiologically tolerable salts thereof. A salt may be formed at the 2-carboxylic acid group or at any other acidic or basic centre present. Moreover, when both an acidic centre and a basic centre are present, a compound of formula I may exist in a zwitterionic form.

The stereochemistry at positions 5, 6 and 8 of a compound of formula I can be R or S, independently (R and S being as defined by the Cahn-Ingold-Prelog system of nomenclature). The preferred stereochemistry at position 5 is R, at position 6 is S, and at position 8 is R.

The present invention also provides a process for the production of a compound of the general formula I, or an ester or salt thereof, which comprises reacting a compound of formula II or of formula IX

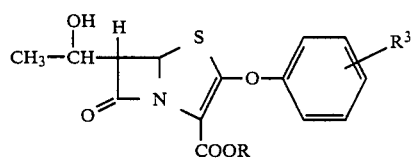

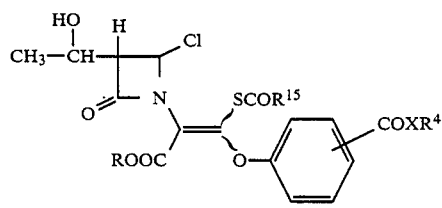

in which R represents a hydrogen atom or a carboxy protecting group, R³ represents an activated carboxylic acid group, R⁴ represents an alkyl group having from 1 to 4 carbon atoms, or a phenyl group which may be unsubstituted or substituted by one or more substituents, which may be the same or different, selected from chlorine and fluorine atoms, cyano and nitro groups, and alkoxy groups, R¹⁵ represents a phenyl group or an alkyl group having from 1 to 4 carbon atoms, and X represents an oxygen or sulphur atoms, with an amine of formula III $R^1NH_2$ (III)

in which R¹ is as above to give a compound of formula I or an ester thereof of formula Ia

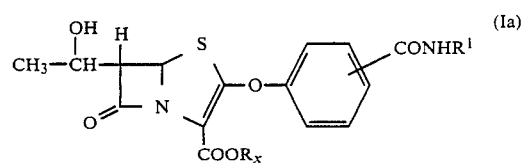

in which $R_x$ represents a carboxy protecting group and, if desired, carrying out any one or more of the following steps in any desired order:
(a) hydrolysing an ester of formula Ia to give the corresponding free acid of formula I,
(b) reacting a free acid of formula I or a salt thereof with an agent cabable of forming an ester, for example, with an alcohol, a phenol or a reactive derivative thereof to give an ester of formula Ia,
(c) carrying out an acid or base catalysed ester interchange on an ester of formula Ia to give a different ester of formula Ia,
(d) reacting a free acid of formula I with a base to give a salt at the carboxylic acid group at position 2,
(e) reacting a free acid of formula I or an ester of formula Ia having a basic group with an acid to give an acid addition salt thereof,
(f) hydrolysing the ester group from an ester of formula Ia in the presence of a salt-forming agent, for example, an alkali metal salt, to give a salt of a compound of formula I,
(g) reacting a salt of a compound of formula I with an acid to give a free acid of formula I, and
(h) reacting a compound of formula I or a salt thereof, or an ester of formula Ia, with an organic acid to give a compound of formula I or an ester of formula Ia having an esterified hydroxy group at the 8-position.

In a particularly preferred case, the activated carboxylic acid group R³ in compound II is a group of formula —COXR⁴ in which X and R⁴ are as defined above, giving a compound of formula IV

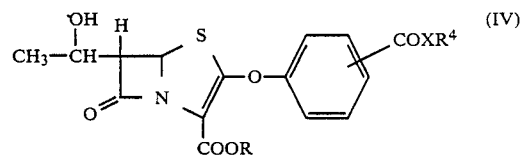

In a compound of formula IV or formula IX, R⁴ preferably represents a phenyl group substituted by one or more chlorine and/or fluorine atoms. When X represents a sulphur or oxygen atom, R⁴ especially represents a pentafluorophenyl group, and when X represents a sulphur atom, 4-chlorophenyl and 2,4,5-trichlorophenyl groups are also particularly preferred as R⁴.

Reaction of the compound of formula IV with the amino compound of formula III is preferably carried out at a temperature within the range of from −40° to +40° C., preferably from 0° to 20° C. The choice of solvent is wide, provided that the solvent does not itself react with any of the reagents or intermediates. For this reason it is often preferable to use a solvent or solvent mixture that is substantially free of water. Examples of suitable solvents are dimethylformamide and acetonitrile.

The reaction between an amine of formula III and a compound of formula IV may be carried out in the presence of a metal salt, especially a salt of a metal selected from Groups IB, IIB and VIII of the Periodic Classification of the Elements (cf E. Cartmell & G. W. A. Fowles, Valency and Molecular Structure, Butterworths, 1966), for example, a salt of copper, rhodium, mercury, zinc, cadmium or, especially, silver. The salt is, for example, a salt with an organic or inorganic acid, for example, with perchloric, tetrafluoroboric, acetic, trifluoromethanesulphonic, or trifluoroacetic acid, or with imidazole. Examples of preferred salts are silver acetate, silver trifluoroacetate, silver trifluoromethanesulphonate, and silver imidazolide.

The degree of advantage resulting from the presence of a metal salt during the reaction between an amine of formula III and a compound of formula IV depends on the reactivity of the —COXR$^4$ group in the compound of formula IV, and may be determined empirically, for example, there is not generally a substantial advantage when X represents an oxygen atom. In the case of a compound of formula IV having a pentalfuorophenythio -(carbonyl) ester group, a metal salt may be used if desired, but the resulting advantage is not large, whereas for other compounds of formula IV in which X represents a sulphur atom, the presence of a metal salt during the reaction with an amine of formula III results in a greatly improved yield.

A compound of formula IX may be reacted with an amine of formula III under conditions analogous to those described above for compounds IV and III to give a compound of formula I or an ester thereof directly. In this case, it is generally necessary to use at least two molar equivalents of the amine. In formula IX, R$^4$ especially represents a pentafluorophenyl group.

An advantage of the preferred compounds of formula IV over other compounds of formula II is that the activated carboxylic acid group —COXR$^4$ can be introduced at an early stage in the reaction sequence leading to the production of compound IV and is carried through the reaction sequence as shown in Reaction Scheme I below. The production of the other activated acids of formula II involves an extra activating step as shown in Reaction Scheme II below, as in this case, these compounds must be produced via a free carboxylic acid of formula V

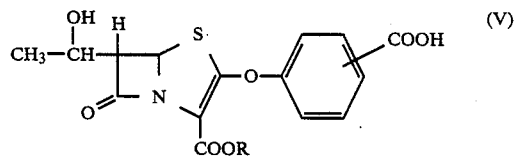

in which R is as defined above.

Overall, a free carboxylic acid group (in compound V) is converted into an amide group (in compound I). The intermediate activated compound of formula II may be produced in a separate reaction step and isolated, if desired, or it may be converted in situ into a compound of formula I.

The conversion of a carboxylic acid group into an amide group is well known in chemistry, and there is available to those versed in the art a wide range of reagents and methods. In general, the reagents function by converting a carboxylic acid group into an activated derivative thereof, which derivative is then reacted with an amine. Examples of the activation of a carboxylic acid group are by conversions as follows:

(i) to an activated ester, for example, to a phenyl ester using, for example, a bisphenyl carbonate;

(ii) to a phosphorous or phosphoric ester, or a phosphoric acid anhydride, using for example, a phosphinyl halide or a phosphoryl halide;

(iii) to a carboxylic acid anhydride, especially a mixed anhydride, using for example, an acid chloride or bromide, for example, pivaloyl bromide, a carbodiimide, for example, dicyclohexylcarbodiimide or 1-(3-dimethylaminopropyl)-3-ethylcarbodiimide, or a chloroformate;

(iv) to an imidazolide using, for example, N,N'-carbonyldimmidazole;

(v) to an acid chloride using, for example, thionyl chloride; or (vi) to an O-acylurea using, for example, a carbodiimide, for example, as described above, and if desired, converting the O-acylurea into an activer ester, for example, an ester with 1-hydroxybenzotriazole or with N-hydroxysucciinimide.

Examples of activated acid groups R$^3$ that can be converted into groups of formula —CONHR$^1$ under reaction conditions that do not affect other parts of the compound of formula II (other than groups —COXR$^4$ as defined above) are, for example, groups of the formula —COOR$^5$ in which R$^5$ represents one of the following groups

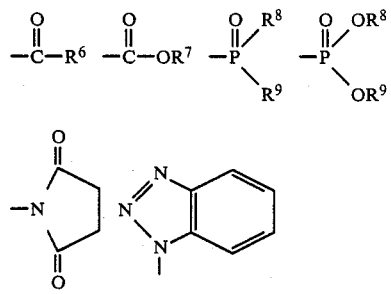

in which R$^6$ represents an alkyl group having up to 4 carbon atoms, especially a t-butyl group; R$^7$ represents an alkyl group having up to 4 carbon atoms, especially an iso-butyl group, R$^8$ and R$^9$, which may be the same or different, each represents an alkyl group having up to 4 carbon atoms or a phenyl group.

The above methods are examples of the techniques available in the art, and do not constitute an exhaustive list. For further information see, for example, M. Bodanszky, Y. S. Flausner and M. A. Ondetti, "Peptide Synthesis", J. Wiley and Sons, New York, 1976, and N. F. Norton, Organic Reactions, Vol. 12, 157 (1962).

Some of the methods for converting a carboxylic acid group into an amide are extremely mild and therefore well suited to the conversion of a penem containing a carboxylic acid group into a penem containing an amide group without damage to any other part of the molecule. Thus, for example, a solution of a carboxylic acid of formula V in an inert solvent, for example, dichloromethane, acetonitrile or tetrahydrofuran, may be treated with a carbodimmide, for example, dicyclohexylcarbodimmide and 1-hydroxybenzotriazole at a temperature within the range of from −40° to +40° C., preferably from 0° to 20° C., to form the benzotriazol-1-yl ester.

An activated penem of formula II formed from a free acid of formula V may be reacted in situ with the amino compound of formula III to form a compound of formula I or an ester thereof, or the activated penem of formula II may first be isolated and purified before reaction with the amino compound. Reaction of the activated penem in either case with the amino compound III is preferably carried out at a temperature within the range of from −40° to +40° C., preferably from 0° to 20° C. The choice of solvent is wide, provided that the solvent does not itself react with any of the reagents or intermediates. For this reason it is often preferable to use a solvent or solvent mixture that is substantially free of water.

The compound of formula I produced from compound II or from compound IV may be converted, if desired, into an ester of formula Ia, and an ester of formula Ia produced from compound II or IV may be converted into the corresponding free acid of formula I, as described above. Other acid/ester/salt interconversions can also be carried out as described above.

As indicated above, a compound of formula I may be in the form of an ester at the carboxy group at position 2, that is to say, a compound of formula Ia. Such as ester is particularly one that can be converted into the free acid by hydrolysis, photolysis, reduction or esterase enzyme action. Examples of such esters are those formed with unsubstituted or substituted aliphatic alcohols or phenols having up to 20 carbon atoms in total. In an esterified carboxy group of formula —COOR$_x$, the group R$_x$ may be, for example, a straight or branched chain substituted or unsubstituted alkyl, alkenyl or alkynyl group having up to 18 carbon atoms, preferably up to 8 carbon atoms, and especially up to 4 carbon atoms, for example, a methyl, ethyl, n-propyl, iso-propyl, n-butyl, sec-butyl, iso-butyl, tert-butyl, n-pentyl, n-hexyl, allyl or vinyl group. An aliphatic group R$_x$, especially a methyl or ethyl group, may be substituted, for example, by an acyloxy group (further details of such groups are given below); by an aminoalkanoyloxy group; by an optionally substituted 2-amino group; or by one or more unsubstituted or substituted phenyl groups. A phenyl group, either as a phenol or as a substituent of an aliphatic group, may be substituted, for example, by one or more substituents, selected especially from nitro groups and halogen atoms. Examples of phenyl substituted-aliphatic groups, are benzyl, p-nitrobenzyl, benzhydryl and trityl groups.

As indicated above, an ester group is especially one that can be removed by hydrolysis, photolysis, reduction or enzyme action, or two or more of these methods may be used, for example, reduction followed by hydrolysis. A group R$_x$ that can be removed readily without substantial degradation of the rest of the molecule is particularly useful as a carboxy protecting group. Examples of esters that are readily split by reduction are phenyl substituted-methyl esters, which may be unsubstituted or substituted, for example, benzyl, p-nitrobenzyl, benzhydryl and trityl esters.

Reduction of an ester, for example, a phenyl substituted-methyl ester, for example, a p-nitrobenzyl ester, may be carried out using hydrogen and a metal catalyst, for example, a noble metal catalyst, for example, platinum, palladium or rhodium, which catalyst may be supported, for example, on charcoal or kieselguhr.

Alternatively, a p-nitrobenzyl ester may be converted into the corresponding free acid by a two-step method, with an initial reduction of the nitro group followed by hydrolysis. The nitro group may be reduced by noble metal catalysed hydrogenation, for example, using platinum, or palladium on carbon, or by a metal reducing agent, for example, zinc in acetic acid. Other metal reducing agents are, for example, aluminium amalgam, and iron and ammonium chloride, see for example, British Patent Specification No. 1,582,960. Reduction of the nitro group is followed by hydrolysis which may occur in situ during reduction of the nitro group or which may be carried out subsequently by treatment with an acid or a base.

An o-nitrobenzyl ester may be converted into the corresponding free acid by photolysis.

Certain ester groups may be split off by base hydrolysis, for example, acetylmethyl and acetoxymethyl ester groups.

There may be used an esterifying group that is removable under physiological conditions, that is to say, the esterifying group is split off in vivo to give the free acid or the carboxylate, for example, an acyloxymethyl or acyloxyethyl ester, for example, an acetoxymethyl, 1′-(acetoxy)ethyl or pivaloyloxymethyl ester, a 5-methyldioxalen-2-on-4-yl-methyl ester, an aminoalkanoyloxymethyl ester, for example, a glycyloxymethyl, L-valyloxymethyl or L-leucyloxymethyl ester, or a phthalidyl ester, or a 1′-(alkoxycarbonyloxy)ethyl ester, for example, a 1′-methoxycarbonyloxy)ethyl or 1′-(ethoxycarbonyloxy)ethyl ester, or an optionally substituted 2-aminoethyl ester, for example, a 2-diethylaminoethyl or 2-(1-morpholino)-ethyl ester, acyl and alkanoyl groups having from 2 to 12 carbon atoms.

Preferred esters are the p-nitrobenzyl, phthalidyl, pivaloyloxymethyl, ethoxycarbonyloxymethyl, 5-methyldioxalen-2-on-4-yl-methyl, acetylmethyl, acetoxymethyl, 1′-(acetoxy)ethyl, 1′-(acetyl)ethyl and 1′-(ethoxycarbonyloxy)ethyl esters.

An ester of a compound of formula I, or of any other free acid described herein, may be prepared by reaction of the appropriate free acid with an alcohol, a phenol or a reactive derivative thereof. The reaction is preferably carried out under mild conditions in order to prevent rupture of the ring system, for example, under neutral or mild acidic or basic conditions, and at temperatures within the range of from −70° to +35° C.

An ester derived from an alcohol may also be produced by reaction of a reactive derivative of the alcohol, for example, a halide, for example, a chloride, bromide or iodide, or hydrocarbonsulphonyl derivative, for example, a mesyl or tosyl ester, with a salt of an acid of formula I or of another free acid described herein, for example, an alkali or alkaline earth metal salt, for example, a lithium, sodium, potassium, calcium or barium salt, or an amine salt, for example, a triethylammonium salt. The reaction is preferably carried out in a substituted sulphoxide or amide solvent, for example, in dimethyl sulphoxide, dimethylformamide, or hexamethylphosphoramide or, alternatively, an ester may be prepared by reaction of the acid with the alcohol or phenol in the presence of a condensing agent, for example, dicyclohexylcarbodiimide.

The above considerations regarding free and esterified carboxylic acid groups at position 2 also apply to free and esterified carboxylic acid groups present as a substitutent of R$^1$ or as part of a substituent or R$^1$.

As described above, a compound of formula I may also form an ester at the 8-hydroxy group. Such an ester group is especially one that can be removed in vivo to give the free hydroxy group, that is to say, an ester group that can be removed under physiological conditions. Examples of suitable esterifying groups are those of the formula $R_zCO-$ in which $R_z$ represents a hydrogen atom or a straight or branched chain alkyl group having from 1 to 4 carbon atoms, especially a methyl, ethyl or t-butyl group, or represents a phenyl group or a phenoxyalkyl group in which the alkyl moiety is straight-chained or branched and has 1 to 4 carbon atoms, and is especially a methyl group.

An ester group at the 8-position may be the only ester group present, or it may be present in addition to an ester group at the 2-carboxyl group and/or as a substituent of $R^1$ or as part of a substituent of $R^1$. An ester group may be introduced at the 8-hydroxy group by a reaction with an organic acid in known manner. A particularly convenient method is to react a compound of formula I or an ester thereof of formula Ia with an activated acid derivative, for example, an acid anhydride. In this case, it is advantageous to carry out the reaction in the presence of a catalyst, for example, 4-dimethylaminopyridine.

It has been found that compounds of formula I (and esters thereof at the 2-carboxylic acid group) having an esterified hydroxy group at the 8-position have antibacterial and/or $\beta$-lactamase inhibiting properties, in particular since the 8-ester group can be cleaved in vivo by esterases. In addition, esterification at the 8-hydroxy group can enhance the degree of absorption on oral administration.

The present invention also provides salts of those compounds of formula I that have salt-forming groups, especially the salts of a free acid of formula I and acid addition salts of compounds of formula I having a basic group. The salts are especially physiologically tolerable salts, for example, alkali metal and alkaline earth metal salts, for example, sodium, potassium, lithium, calcium, and magnesium salts, ammonium salts, and salts with organic amines; also physiologically tolerable acid addition salts. These may be formed with a suitable inorganic or organic acid, for example, hydrochloric acid, sulphuric acid, or an organic carboxylic or organic sulphonic acid, for example, p-toluene-sulphonic acid.

A salt of a free acid of formula I may be produced by reacting the free acid with the appropriate base in a solvent, preferably under those conditions under which the salt precipitates. A preferred base is potassium 2-ethylhexanoate.

A salt may be produced directly from an ester by splitting off the ester group under suitable reaction conditions, for example, catalytic reduction of an ester, for example, a p-nitrobenzyl ester, in an aqueous/organic solvent, for example, comprising water and ethyl acetate, dioxane or tetrahydrofuran, in the presence of a metal salt, especially a metal bicarbonate, for example, in an equivalent amount or in a slight excess, yields the salt directly.

A compound of formula IV may be produced as shown in the following Reaction Scheme I:

Reaction Scheme I

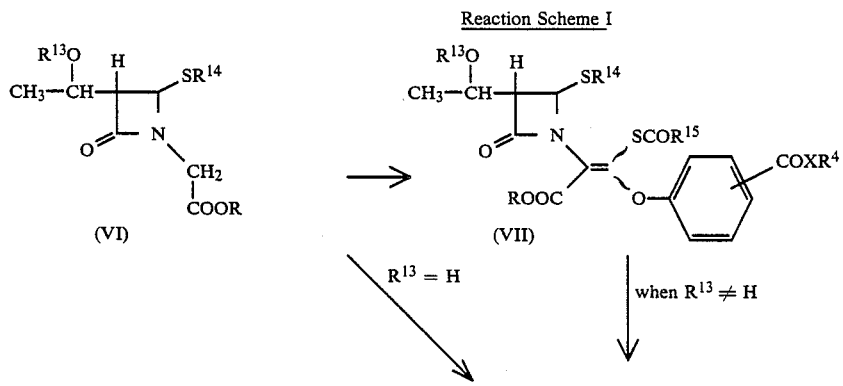

-continued
Reaction Scheme I

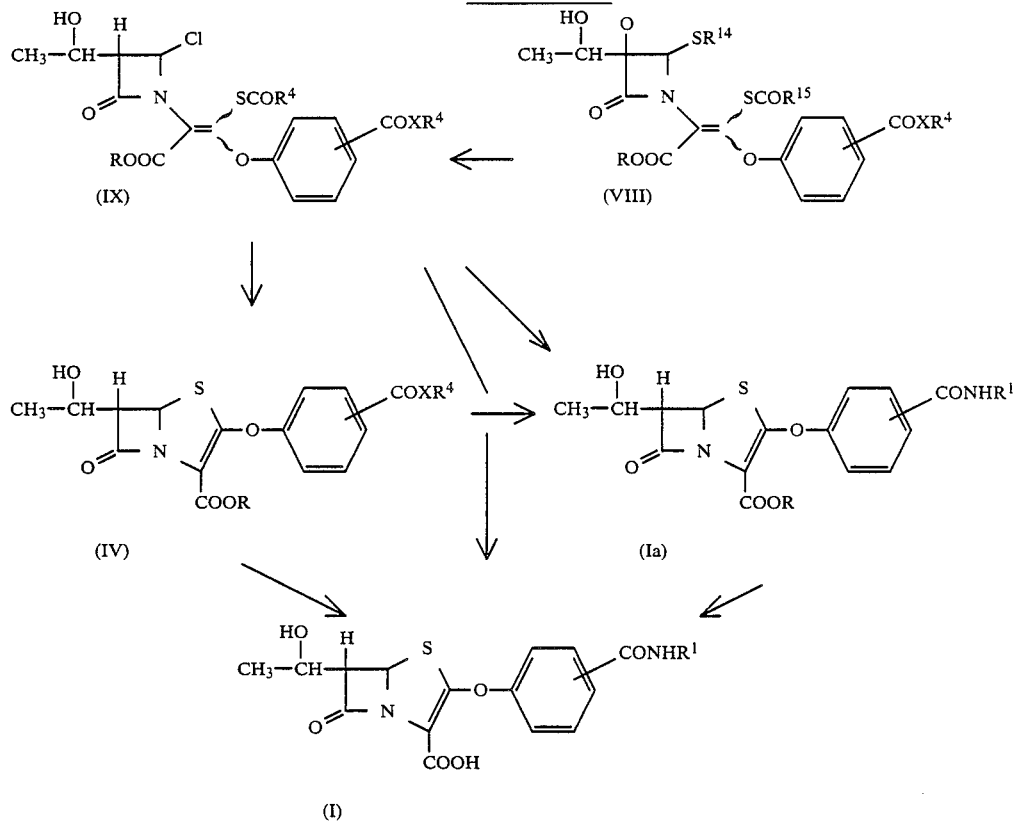

In Reaction Scheme I, X, R, $R^1$ and $R^4$ are as defined above, and preferred meanings for $R^4$ are as given above; $R^{13}$ represents a hydrogen atom or a hydroxy protecting group, and $R^{14}$ and $R^{15}$ each independently represents a phenyl group or an alkyl group having up to 4 carbon atoms.

Compound VI is reacted, in the presence of a base, with a compound of formula X

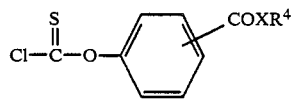 (X)

in which X and $R^4$ are as defined above, followed by reaction with an activated carboxylic acid derivative which comprises the group $R^{15}$ as defined above, for example, with an acyl halide of formula XI

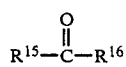 (XI)

in which $R^{15}$ is as defined above and $R^{16}$ represents a chlorine or bromine atom.

While many phenyl chlorothionoformates are known, certain compounds of formula X have not been described before; they may be prepared by methods analogous to those described for the preparation of known compounds, see for example, Rivier & Schalch, Helv. Chem. Acta., Vol 6, 1923, p 605, and Reich & Martin, Chem. Berichte, Vol 98, 1965, p 2063.

The reaction between compound X and compound VI is carried out in the presence of a base, preferably having a $pK_a \geq 20$, preferably a metallated amine, and examples of preferred bases are lithium diisopropylamide, lithium hexamethyldisilazide, lithium 2,2,6,6-tetramethylpiperidide, lithium cyclohexyl isopropylamide, and sodamide.

The reaction is generally carried out in an aprotic solvent, for example, an oxygenated hydrocarbon, preferably an ether, for example, diethyl ether, tetrahydrofuran, dioxane, glyme or diglyme. The reaction temperature is, for example, from $-120°$ to $+30°$ C., preferably from $-78°$ to $-20°$ C.

The amount of base used is, for example, from 1 to 3 moles, calculated per mole of compound VI, preferably from 1.5 to 2.5 moles of base. The compound of formula X is preferably used in an amount of from 1 to 1.5 moles per mole of compound VI, preferably from 1 to 1.1 moles of compound X per mole of compound VI.

The reaction may be carried out as follows: The base may be added to a stirred solution of compounds VI and X. Alternatively, to a stirred solution of compound VI under an inert atmosphere is added the base and subsequently a solution of compound X in the same or a different solvent.

The activated acid derivative, perferably of formula XI, is preferably added to the mixture resulting from the reaction of compounds VI and X, especially in an amount of from 1 to 2 moles calculated on compound VI. The reaction is preferably carried out at a temperature of from $-40°$ to $+40°$ C., adding the compound of formula XI to the reaction mixture at the temperature at which the reaction between compounds VI and X took place, and then warming, or working-up at this temperature.

The —SCOR$^{15}$ group in the resulting compound of formula VII may be E or Z to the —COOR group. (The terms E and Z are as defined on page 142 of Allinger et al. "Organic Chemistry" 1971, Worth, N.Y.) The isomers may be separated for the subsequent reaction, but this is not generally necessary, and the isomeric mixture is generally used as both iosmers give a compound of formula I.

It is preferably that R$^{13}$ in compound VI represents a hydroxy protecting group to prevent the hydroxy group from reacting with the compound of formula X. The protective group is then removed from compound VII in order to obtain the desired 5R stereochemistry in the final product. The protective group may be removed in any conventional manner to give compound VIII. Preferred hydroxy-protecting groups R$^{13}$ are those that are compatible with the synthesis of the compound of formula VII and which may be removed under conditions in which the resulting compound VIII is stable. Compound VIII has been found to be substantially stable in the presence of a proton source, for example, hydrogen chloride, aqueous hydrochloric acid or aqueous hydrofluoric acid. Accordingly, one type of preferred hydroxy protecting group R$^{13}$ is that which can be removed under acidic conditions. Such groups are well known in the art and are, for example, tetrahydropyranyl and tetrahydrofuranyl groups; acetal and ketal groups, for example, of formula

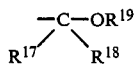

in which R$^{17}$ and R$^{18}$, which may be the same or different, each represents a hydrogen atom or a lower alkyl group, preferably a methyl group, or R$^{17}$ and R$^{18}$ together with the carbon atoms to which they are attached, represent a cycloalkyl ring having from 4 to 7 carbon atoms, and R$^{19}$ represents a lower alkyl group, preferably a methyl or ethyl group, or R$^{17}$ and R$^{19}$, together with the carbon atom and the oxygen atom to which they are attached, respectively, represent a tetrahydropyranyl ring; also silyl ethers, for example, having three substituents on the silicon atom, and preferably up to 24 carbon atoms in total, the three substituents being the same or different, and selected from alkyl, alkenyl and cycloalkyl groups, and phenyl and phenalkyl groups which may be unsubstituted or substituted as defined above, for example, —SiR$^8$R$^9$R$^{10}$ groups, in which R$^8$, R$^9$ and R$^{10}$ are as defined above, that is to say, they may be the same or different, and each represents a lower alkyl group or a phenyl group, for example, giving trimethylsilyl, triethylsilyl, diphenyl-t-butylsily, dimethyl-t-butylsilyl, and methyldiphenylsilyl groups; and stannyl groups, for example, having up to 24 carbon atoms and three substituents, which may be the same or different, selected from alkyl, alkenyl, cycloalkyl, alkoxy and phenoxy groups, and phenyl and phenalkyl groups which may be unsubstituted or substituted, for example, groups of the formula SnR$^{20}$R$^{21}$R$^{22}$, in which R$^{20}$, R$^{21}$ and R$^{22}$, which may be the same or different, each represents a lower alkyl group, for example, a tri-n-butylstannyl group. (The term "lower" is used in the present specification to denote groups having up to 4 carbon atoms).

Preferred R$^{13}$ groups are tetrahydropyranyl, 2-methoxyprop-2-yl, trimethylsilyl, triethylsilyl and, especially, t-butyldimethylsilyl groups.

Such groups may be removed by acid hydrolysis, for example, using 0.1 to 2M, preferably 0.5M hydrochloric acid, for example, 6M HCl in, for example, tetrahydrofuran, cf. Belgian Patent Specification No. 881 012; n-Bu$_4$NF in an acidic medium, for example, in acetic acid, cf. Belgian Patent Specification No. 882 764; or aqueous hydrogen fluoride, for example, in the presence of acetonitrile, cf. J. Chem. Soc. Perkin 1, 1981, 2055.

The resulting compound VIII having a free hydroxy group is then chlorinated using an agent capable of splitting a carbon-sulphur bond and of introducing a chlorine atom. Such agents are well known in the art and include, for example, molecular chlorine, sulphuryl chloride, t-butyl hypochlorite and cyanogen chloride.

The reaction is generally carried out at a temperature within the range of from $-60°$ to $+20°$ C. The reaction is generally carried out in a solvent or diluent that is non-protic, and is inert under the reaction conditions, for example, an ether, a hydrocarbon or a halogenated hydrocarbon, for example, dioxane, benzene, chloroform or methylene chloride. A mixture of two or more solvents may be used. Examples of halogenating systems are: chlorine in chloroform, chlorine in benzene and t-butyl hypochlorite in benzene. In the latter two cases, the temperature is preferably from 5° to 20° C., and normally from 5° to 10° C. Generally, 1 to 2 moles of chlorine are used per mole of compound VIII, cf. S. Kukolja, J. Amer. Chem. Soc. (1971), 93, 6267 and P. C. Cherry, C. E. Newall and N. S. Watson, J.C.S. Chem. Comm. 1979 p. 663.

The resulting compound of formula IX may be converted into a compound of formula IV in the presence of a base. The base used for this reaction should not affect the 13 COXR$^4$ group. The base may be inorganic or organic, and may be chosen, for example, from ammonia, or an alkali metal, especially a sodium or potassium, carbonate, bicarbonate, or hydroxide; a primary amine, for example, methylamine, ethylamine, aniline or benzylamine; an alkali metal alkoxide, for example, sodium methoxide; or a heterocyclic base, for example, having a pK$_a$ within the range of from 5 to 9, for example, imidazole, pyridine or a substituted pyridine, for example, an alkyl, amino or alkylamino-substituted pyridine, for example, 4-methylpyridine or 4-dimethylaminopyridine. Imidazole is particularly preferred.

The reaction is generally carried out in a solvent or diluent, the choice of which is wide, provided that it is inert under the reaction conditions. Examples of solvents and diluents are oxygenated hydrocarbons, for example, alcohols, for example, having up to 4 carbon atoms, for example, ethanol; ethers, for example, having up to 4 carbon atoms, for example, diethyl ether, also tetrahydrofuran and dioxane; ketones, for example, having up to 4 carbon atoms, for example, acetone and methyl ethyl ketone; esters, for example, methyl acetate and ethyl acetate; and amides, for example, dimethylformamide and dimethylacetamide; also chlorinated hydrocarbons, for example, chloroform, methylene chloride and carbon tetrachloride; aromatic hydrocarbons, for example, benzene and toluene; and other solvents for example, acetonitrile and nitromethane. A mixture of two or more solvents may be used, and solvents are preferably used in admixture with water, preferably a water-miscible solvent is used in admixture with 5 to 20% (v/v) water.

The reaction is generally carried out at a temperature within the range of from 0° to 40° C., preferably from 0° to 20° C.

A compound of formula IV may be converted into a compound of formula I or Ia as described above.

As mentioned above, if the base that is reacted with compound IX is an amine of formula III

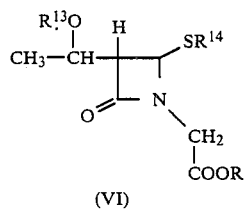

in which $R^1$ is as defined above, then compound IX can be converted directly into compound I or Ia. In this case it is generally necessary to use two or more moles of the amine of formula III per mole of compound IX. For direct conversion to compound I or Ia, $R^4$ in compound IX preferably represents a 4-chlorophenyl or 2,4,5-trichlorophenyl group when X represents a sulphur atom or, especially, represents a pentafluorophenyl group when X represents an oxygen or sulphur atom. Particularly preferred are compounds of formula IX wherein X represents an oxygen atom and $R^4$ represents a pentafluorophenyl group.

Compound IX may be converted to compound I or Ia via the in situ formation of compound IV, or the $XR^4$ group in compound IX may be displaced by the amine before cyclisation. Both pathways are part of the present invention.

A compound of formula I or an ester of formula Ia may be prepared as shown in the following Reaction Scheme II:

Reaction Scheme II

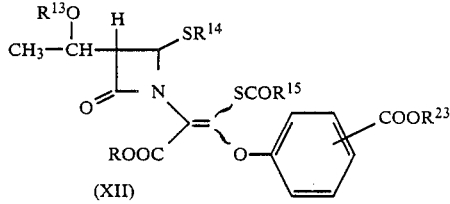

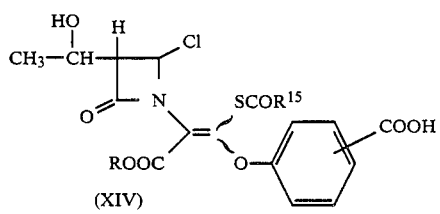

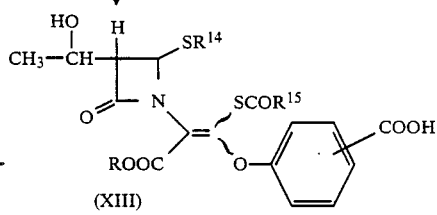

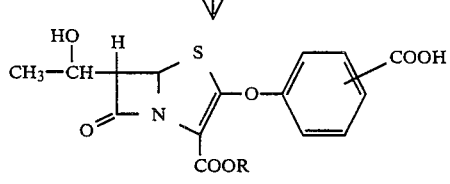

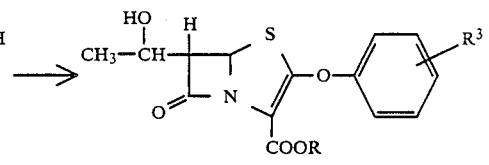

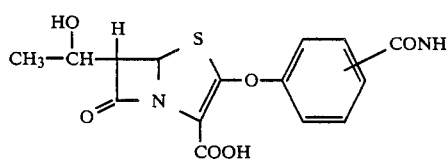

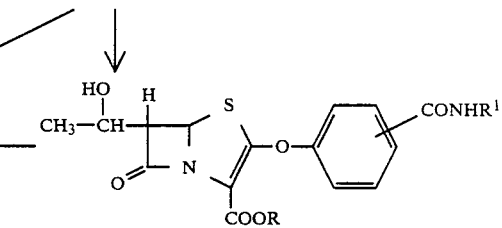

in which R, $R^1$, $R^3$, $R^{13}$ $R^{14}$ and $R^{15}$ are as defined above, and $R^{23}$ represents a carboxy protecting group.

A compound of formula VI may be converted into a compound of formula XII by reaction, in the presence of a base, with a compound of formual XVI

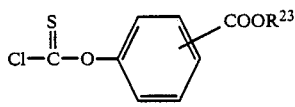 (XVI)

in which R²³ is as defined above, followed by reaction with an activated carboxylic acid derivative which comprises the group R¹⁵, for example, with an acyl halide of formula XI as defined above to give a compound of formula XIII. These reactions are carried out as described in Reaction Scheme I for the reaction of the corresponding compounds VI and X followed by reaction with compound XI to give the corresponding compound of formula VII.

In compound XII, R²³ represents a carboxy protecting group, and it is preferable to use a carboxy protecting group that can be removed under the same conditions as the hydroxy protecting group R¹³, that is to say, preferably under acidic conditions. Examples of such hydroxy protecting groups are given above with reference to compound VII. Preferably R²³ is a silyl group, for example, as described above for R¹³, and is especially a diphenyl-t-butylsilyl group. Compound XII can thus be converted into compound XIII in one step by the simultaneous removal of the two protecting groups R¹³ and R²³.

The chlorination of compound XIII may be carried out as described above in Reaction Scheme I for the chlorination of compound VIII, and the resulting compound of formula XIV may be converted into a compound of formula V in the presence of a base, as described above in Reaction Scheme I for the ring closure of compound IX to give compound II.

A compound of formula V may be converted into a compound of formula II and then into a compound of formula I or Ia as described above.

In both of the above Reaction Schemes, in some cases it may be preferable to retain the carboxy protecting group R until after formation of the desired compound of formula Ia. The carboxy protecting group R is as defined above, and preferably represents a p-nitrobenzyl group. In other cases, for example, when a compound of formula IV is used, it may be desirable that R represents a hydrogen atom. A carboxy protecting group R may be removed from the 2-carboxy group at any appropriate point in the reaction sequence.

If desired, an ester group —COOR can be transesterified by ester interchange at any stage of the reaction scheme, and especially after formation of an ester of formula Ia, to give another ester of formula Ia, for example, an ester that can be converted into the free acid of formula I or a carboxylate under physiological conditions. Alternatively, a resulting ester of formula Ia can be converted into the free acid or a salt; a free acid can be esterified or converted into a salt; or a salt can be converted into the free acid, an ester or a different salt. In each case, the salt is especially a physiologically tolerable salt, and an ester is especially one that can be removed under physiological conditions Examples of such procedures are given above.

At each stage of either of the reaction sequences, the desired compound may be isolated from the reaction mixture and, if desired, purified by the appropriate techniques used for the purification of organic compounds, for example, chromatography and crystallisation.

As indicated above, various intermediates may be produced in the form of mixtures of isomers of various kinds. Such mixtures may be separated or resolved at any stage, or an isomeric mixture may be used per se for subsequent reactions.

Chlorination of the 4R-isomer of a compound of formula VIII or XIII gives predominantly the 4S-isomer of compound IX or XIV, respectively. The proportion of 4S:4R-isomers of compound IX or XIV depends on the chlorination agent and reaction conditions used, but in general varies from 3:1 to as high as 18:1. The 4R- and 4S-isomers can be separated readily, for example, by chromatography. A compound of formula IX or XIV also has E/Z isomerism at the double bond, and in some cases, the chlorinated compound of formula IX or XIV is obtained in the form of a substantially pure E or Z isomer. In other cases, an E/Z isomeric mixture is obtained, and the 4R- and 4S-isomers may be separated further into the individual E and Z isomers if desired. It is not generally necessary to separate the E and Z isomers, but it is preferable to separate the 4R- and 4S-isomers before conversion into a compound of formula IV or V, respectively, as the 4S-isomer is converted by reaction with a base into the more desirable 5R-isomer of formula IV or V and, subsequently, of formula I or Ia.

As mentioned above, a compound of formula I may have the R or S stereochemistry independently at positions 5, 6 and 8. Any mixture of two or more isomeric forms may be resolved, if desired, or a compound of formula I can be used in the form of an isomeric mixture. The preferred stereochemistry at position 5 in compound I is generally R, corresponding to that in naturally occurring penicillins and cephalosporins, at position 6 is S and at position 8 is R.

The compounds of formula I and salts thereof are β-lactamase inhibitors, and the compounds are generally stable to the action of β-lactamases produced by gram positive organisms, for example, *Staphylococcus aureus* and gram negative organisms, for example, *Enterobacter cloacae*. They also possess antibacterial properties themselves and may be used in humans and other animals, for example, to treat bacterial infections caused by gram-positive and gram-negative bacteria, for example, *Staphylococcus aureus, Streptococcus pyogenes, Bacillus subtilis, Escherichia coli, Pseudomonas aeruginosa,* and *Proteus morganii*, some strains of which are penicillin resistant.

The present invention accordingly provides a pharmaceutical preparation which comprises a compound of formula I, or a physiologically tolerable salt thereof, or a mixture of two or more such substances as active ingredient, in admixture or conjunction with a pharmaceutically suitable carrier. The preparation may also comprise one or more other pharmaceutically active substances, for example another antibacterial substance, especially one having a β-lactam ring. The preparations may be in a form suitable for enteral or parenteral administration, for example, for oral intravenous or intramuscular administration, for example, as tablets, capsules, syrups, or sterile injectable or infusion solutions. The preparations are advantageously in unit dosage form and preferably comprise from 10 to 2000 mg of the active ingredient per unit dose. The daily dosage of the active ingredient is generally from 20 to 8000 mg, in divided doses, generally up to 4 doses.

The invention also provides the use of a compound of formula I or a physiologically tolerable ester or salt thereof for the manufacture of a medicament for the treatment of bacterial infections.

The invention further provides a method of treating mammals, especially humans, to combat a bacterial infection, which comprises administering to the mammal a compound of formula I or a physiologically tolerable ester or salt thereof.

The invention further provides a pharmaceutical preparation which comprises an active ingredient as defined above, in unit dosage form.

The invention also provides a pharmaceutical preparation which comprises an active ingredient as defined above, or a physiologically tolerable salt thereof or a mixture of two or more such substances, and one or more further pharmaceutically active substances, in unit dosage form.

Unit dosages are preferably as described above.

The present invention also provides compounds of the general formulae II, IV, V, IX, VIII, VII, XIV, XIII and XII.

All the compounds of the present invention may exist in various isomeric forms. The invention includes all isomeric forms, either in the form of isolated isomers or of mixtures of any two or more isomers.

Those compounds of formula I in which $R^1$ represents an alkyl group having from 1 to 5 carbon atoms substituted by a substituent as defined in (xii), (xiii), (xiv) or (xv) above, may be regarded as amino acid or peptide derivatives. Examples of such compounds are (1) 5R,3-[3-(N-(carbamoylmethyl)carbamoyl)phenoxy]-6S-(1R-hydroxyethyl)-7-oxo-4-thia-1-azabicyclo[3,2,0]hept-2-ene-2-carboxylic acid;

(2) 5R,3-[4-(N-(carbamoylmethyl)carbamoyl)phenoxy]-6S-(1R-hydroxyethyl)-7-oxo-4-thia-1-azabicyclo[3,2,0]hept-2-ene-2-carboxylic acid; and (3) 5R,3-[4-(N-(N-(carbamoylmethyl)carbamoylmethyl)carbamoyl)phenoxy]-6S-(1R-hydroxyethyl)-7-oxo-4-thia-1-azabicyclo[3,2,0]hept-2-ene-2-carboxylic acid.

Examples of preferred compounds of the present invention are peptide and amino acid derivatives of formula I described in general terms above, particularly those in which the 3-substituent has a terminal carbamoyl group, and especially those compounds (1) to (3) named above. Also preferred are the following compounds of formula I:

(4) 5R,3-[4-((N-hydroxycarbamoyl)methylcarbamoyl)phenoxy]-6S-[1R-hydroxyethyl]-7-oxo-4-thia-1-azabicyclo[3,2,0]hept-2-ene-2-carboxylic acid;

(5) 5R,3-[4-((1-carbamoyl-2-hydroxyethyl)carbamoyl)phenoxy]-6S-[1R-hydroxyethyl]-7-oxo-4-thia-1-azabicyclo[3,2,0]hept-2-ene-2-carboxylic acid;

(6) 5R,3-[4-((cyanomethyl)carbamoyl)phenoxy]-6S-[1R-hydroxyethyl]-7-oxo-4-thia-1-azabicyclo[3,2,0]hept-2-ene-2-carboxylic acid; and (7) 5R,3-[4-((2-aminoethyl)carbamoyl)phenoxy]-6S-[1R-hydroxyethyl]-7-oxo-4-thia-1-azabicyclo[3,2,0]hept-2-ene-2-carboxylic acid.

In each case, the preferred compound is the free carboxylic acid, or a salt thereof, or an ester at the 2-and/or 8-position.

Physiologically tolerable salts and esters removable by esterase enzyme action under physiological conditions are the preferred salts and esters of these preferred compounds.

The following Examples illustrate the invention, but are not limiting. Values indicated by "δ" are obtained by $^1$NMR spectroscopy.

EXAMPLE 1

S-(2,4,5-Trichlorophenyl) 4-(acetoxy)thiobenzoate

A solution of 4-acetoxybenzoyl chloride (8.37 g) in dry acetonitrile (20 ml) was added to a solution of 2,4,5-trichlorothiophenol (9.00 g) in dry acetonitrile (120 ml) and the mixture stirred at room temperature whilst pyridine (3.41 ml) was added dropwise over 10 minutes. Stirring was continued until the reaction was complete, when ethyl acetate was added and the solution washed with water. Evaporation of the solution, which had been dried over magnesium sulphate, afforded the desired thioester (15.36 g).

δ (CDCl$_3$) 2.30 (3H, s); 7.10–8.30 (2H, m); 7.28, 8.11 (4H, AA'BB', J=9 Hz).

EXAMPLE 2

S-(Pentafluorophenyl) 4-(acetoxy)thiobenzoate

A solution of 4-acetoxybenzoyl chloride (4.96 g) in dry dichloromethane (20 ml) was added dropwise over 15 minutes to a stirred solution of pentafluorothiophenol (5.00 g), pyridine (2.1 ml) and 4-N,N-dimethylaminopyridine (50 mg) in dry dichloromethane (75 ml), the mixture being maintained close to 5° C. by immersion in an ice-bath. The reactants were allowed to reach room temperature overnight and the organic solution was washed successively with aqueous 2M hydrochloric acid, a saturated sodium bicarbonate solution and water. Evaporation of the solution, which had been dried over magnesium sulphate, afforded the desired thioester (8.79 g).

$v_{max}$ (film) 1765, 1700, 1685, 1638 cm$^{-1}$.

δ (CDCl$_3$) 2.33 (3H, s); 7.28, 8.06 (4H, AA'BB', J=9 Hz).

EXAMPLE 3

S-Phenyl 4-(acetoxy)thiobenzoate

Copper (I) thiopenoxide (4.06 g) was added to a solution of 4-acetoxybenzoyl chloride (4.67 g) in dry acetonitrile (40 ml). The mixture was heated to reflux for 2 hours, cooled, and the solvent evaporated in vacuo. The residue was taken up in ethyl acetate, and the filtered solution washed successively with a cold, dilute ammonia solution, water and brine. Evaporation of the solution, which had been dried over magnesium sulphate, afforded the desired thioester (5.53 g).

δ (CDCl$_3$) 2.30 (3H, s); 7.00–7.60 (5H, m); 7.14, 7.98 (4H, AA'BB', J=9 Hz).

EXAMPLE 4

S-(4-Chlorophenyl) 4-(acetoxy)thiobenzoate

4-Chlorothiophenol (21.6 g) was dissolved in dry acetonitrile (500 ml) and a solution of 4-acetoxybenzoyl chloride (29.7 g) in acetonitrile (50 ml) was added. The mixture was stirred at room temperature whilst pyridine (12.1 ml) was added rapidly dropwise. When the reaction was complete the bulk of the solvents was removed by evaporation in vacuo and the residue partitioned between ethyl acetate and water. The separated organic layer was washed with water and brine, dried over magnesium sulphate, and evaporated to afford the desired thioester as a pale yellow solid (41.0 g).

δ (CDCl$_3$) 2.31 (3H, s); 6.95–7.55 (4H, m); 7.15, 7.98 (4H, AA'BB', J=9 Hz).

EXAMPLE 5

S-(4-Fluorophenyl) 4-(acetoxy)thiobenzoate

A solution of 4-acetoxybenzoyl chloride (7.74 g) in dry acetonitrile (10 ml) was added to a solution of 4-fluorothiophenol (5.00 g) in acetonitrile (40 ml). The mixture was cooled to 5° C. by immersion in an ice-water bath and pyridine (3.15 ml) added dropwise to the stirred solution. The mixture was stirred at 5° C. for 1 hour, allowed to reach room temperature and stirred for a further 2 hours, and then the solvents were evaporated in vacuo. The residue was partitioned between ethyl acetate and water and the separated organic layer was washed successively with water, dilute hydrochloric acid, and water again. Evaporation of the solution, which had been dried over magnesium sulphate, afforded the desired thioester as a pale yellow solid (10.81 g).

$\delta$ (CDCl$_3$) 2.31 (3H, s); 6.85–7.65 (4H, m); 7.19, 8.01 (4H, AA'BB', J=8.5 Hz).

EXAMPLE 6

S-(4-Methoxyphenyl) 4-(acetoxy)thiobenzoate

A solution of 4-acetoxybenzoyl chloride (7.06 g) in dry acetonitrile (15 ml) was added to a solution of 4-methoxythiophenol (5.00 g) in dry acetonitrile (60 ml), and the mixture cooled (ice-bath) and stirred whilst pyridine (2.83 ml) was added dropwise over 10 minutes. The solution was allowed to reach room temperature, stirred for a further 2 hours and the volatile solvents evaporated in vacuo. The residue was partitioned between ethyl acetate and water and the separated organic layer was washed successively with water and brine, dried over magnesium sulphate, and evaporated. Column chromatography of the crude material (silica; ethyl acetate/hexane mixtures as eluant) gave the pure thioester as a pale yellow foam (8.84 g).

$\delta$ (CDCl$_3$) 2.29 (3H, s); 3.76 (3H, s); 6.80–8.15 (4H, m); 7.15, 7.94 (4H, AA'BB', J=9 Hz).

EXAMPLE 7

S-(4-Cyanophenyl) 4-(acetoxy)thiobenzoate

A solution of 4-acetoxybenzoyl chloride (3.33 g) in dry dichloromethane (20 ml) was added over 10 minutes to a cool (5° C.), stirred solution of 4-cyanothiophenol (2.06 g), pyridine (1.45 ml) and 4-N,N-dimethylaminopyridine (25 mg) in dry dichloromethane (30 ml). The stirred solution was allowed to reach room temperature overnight and the organic solution was washed successively with aqueous 2M hydrochloric acid, a saturated sodium bicarbonate solution and water. Evaporation of the extracts, which had been dried over magnesium sulphate, afforded the desired thioester (4.53 g).

$\nu_{max}$ (Nujol mull) 2220, 1757, 1672 cm$^{-1}$.

$\delta$ (CDCl$_3$) 2.35 (3H, s); 7.31, 8.24 (4H, AA'BB', J=9 Hz); 7.40–7.85 (4H, m).

EXAMPLE 8

S-(2-Methylprop-2-yl) 4-(acetoxy)thiobenzoate

4-Acetoxybenzoyl chloride (3.00 g) in dry acetonitrile (10 ml) was addd to a vigorously stirred suspension of copper (I) (2-methylprop-2-yl)thiolate (2.53 g) in dry acetonitrile (35 ml). The mixture was heated under reflux with the exclusion of moisture for 3.5 hours. After cooling, evaporation of the solvent left a residue which was taken up in ethyl acetate (50 ml) and filtered. The filtrate was washed with cold, dilute, aqueous ammonia, then water and finally dried over magnesium sulphate. Evaporation of the filtered solution afforded the desired thioester (3.44 g).

$\nu_{max}$ (film) 1773, 1659 cm$^{-1}$.

$\delta$ (CDCl$_3$) 1.62 (9H, s); 2.33 (3H, s); 7.23, 8.07 (4H, AA'BB', J=8.5 Hz).

EXAMPLE 9

S-(2,4,5-Trichlorophenyl) 4-(hydroxy)thiobenzoate

S-(2,4,5-Trichlorophenyl) 4-(acetoxy)thiobenzoate (10 g) in tetrahydrofuran was treated with 25 ml of 5.6M hydrochloric acid and stirred at room temperature overnight. The solvents were evaporated in vacuo to give a product which was purified by column chromatography (silica; ethyl acetate-hexane mixtures as eluant) to afford the title compound (5.4 g).

$\delta$ (d$_8$-THF) 6.22 (1H, br.s); 6.8–8.2 (6H, m).

EXAMPLE 10

S-(Pentafluorophenyl) 4-(hydroxy)thiobenzoate

The title compound (6.32 g) was prepared from S-(pentafluorophenyl) 4-(acetoxy)thiobenzoate (9.32 g) in a manner analogous to that described in Example 9.

$\delta$ (CDCl$_3$) 5.70 (1H, br.s); 6.98, 8.05 (4H, AA'BB', J=9 Hz).

EXAMPLE 11

S-Phenyl 4-(hydroxy)thiobenzoate

The title compound (4.08 g) was prepared from S-phenyl 4-(acetoxy)thiobenzoate (5.53 g) in a manner analogous to that described in Example 9.

$\delta$ (d$_6$-DMSO) 7.58 (5H, br.s); 7.06, 8.03 (4H, AA'BB', J=9 Hz).

EXAMPLE 12

S-(4-Chlorophenyl) 4-(hydroxy)thiobenzoate

The title compound (5.87 g) was prepared from S-(4-chlorophenyl) 4-(acetoxy)thiobenzoate (10.5 g) in a manner analogous to that described in Example 9.

$\delta$ (CDCl$_3$-d$_6$-acetone) 7.48 (5H, br.s); 6.96, 7.95 (4H, AA'BB', J=9 Hz).

EXAMPLE 13

S-(4-Fluorophenyl) 4-(hydroxy)thiobenzoate

The title compound (8.71 g) was prepared from S-(4-fluorophenyl) 4-(acetoxy)thiobenzoate (13 g) in a manner analogous to that described in Example 9.

$\delta$ (d$_6$-acetone) 6.8–8.15 (9H, br.m).

EXAMPLE 14

S-(4-Methoxyphenyl) 4-(hydroxy)thiobenzoate

The title compound (5.5 g) was prepared from S-(4-methoxyphenyl) 4-(acetoxy)thiobenzoate (8.84 g) in a manner analogous to that described in Example 9.

$\delta$ (CDCl$_3$) - d$_6$-acetone) 3.70 (3H, s); 6.8–8.08 (9H, br.m).

EXAMPLE 15

S-(4-Cyanophenyl)4-(hydroxy)thiobenzoate

The title compound (1.77 g) was prepared from S-(4-cyanophenyl) 4-(acetoxy)thiobenzoate (2.36 g) in a manner analogous to that described in Example 9.

$\delta$ (d$_6$-DMSO) 6.9–8.2 (9H, br.m).

EXAMPLE 16

S-(2-Methylprop-2-yl) 4-(hydroxy)thiobenzoate

The title compound (1.55 g) was prepared from S-(2-methylprop-2-yl) 4-(acetoxy)thiobenzoate (1.93 g) in a manner analogous to that described in Example 9.

δ (CDCl$_3$) 1.57 (9H, s); 6.03 (1H, br.s); 6.86–7.85 (4H, AA'BB', J=9 Hz).

EXAMPLE 17

S-(2,4,5-Trichlorophenyl) 4-(chlorothiocarbonyloxy)thiobenzoate

S-(2,4,5-Trichlorophenyl) 4-(hydroxy)thiobenzoate (5.4 g) in dry chloroform (70 ml) at −20° C. was treated sequentially with sodium hydroxide (0.78 g) in water (3 ml) and thiophosgene (1.85 ml). The solution was allowed to warm to room temperature and was stirred for a further 2 hours. The reaction mixture was then dried over calcium chloride and the filtered solution evaporated to give a crude solid. Purification by chromatography on silica gel using ethyl acetate/hexane mixtures as eluants afforded 3.4 g of the title compound.

δ (CDCl$_3$) 7.10, 8.23 (6H, br.m).

EXAMPLE 18

S-(Pentafluorophenyl) 4-(chlorothiocarbonyloxy)thiobenzoate

S-(Pentafluorophenyl) 4-(hydroxy)thiobenzoate (6.82 g) in dry chloroform (120 ml) was treated with thiophosgene (2.4 ml). This solution was treated with sodium hydroxide (0.85 g) in water (3 ml) with vigorous stirring for 10 minutes. Stirring was continued for 2 hours, when the solution was treated with calcium chloride and stirred for a further hour. Filtration and evaporation of the filtrate gave the title compound (7.6 g) as a homogeneous oil.

$\nu_{max}$ (film) 1755, 1735 cm$^{-1}$.

δ (CDCl$_3$) 7.34, 8.12 (4H, AA'BB', J=8.5 Hz).

EXAMPLE 19

S-Phenyl 4-(chlorothiocarbonyloxy)thiobenzoate

A solution of sodium hydroxide (1.55 g in 150 ml of water was added dropwise with vigorous stirring to a solution of 8.8 g of S-phenyl 4-(hydroxy)thiobenzoate and 3.70 ml of thiophosgene in 250 ml of chloroform, the temperature being kept below 10° C. The mixture was stirred at room temperature for 2 hours and the organic layer separated. The organic layer was washed successively with water and brine, dried over calcium chloride, and evaporated to dryness in vacuo to give 11.57 g of the title compound.

$\nu_{max}$ (film) 1665 cm$^{-1}$.

δ (CDCl$_3$) 7.28, 8.14 (4H, AA'BB', J=9 Hz); 7.40–7.58 (5H, m).

EXAMPLE 20

S-(4-Chlorophenyl) 4-(chlorothiocarbonyloxy)thiobenzoate

A solution of sodium hydroxide (1.28 g) in 5 ml of water was added dropwise over 10 minutes to a vigorously stirred solution of 7.06 g of S-(4-chlorophenyl) 4-(hydroxy)thiobenzoate and 3.09 ml of thiosphosgene in 100 ml of chloroform with cooling. Stirring was continued for 2 hours at room temperature and the filtered solution treated with calcium chloride for a further 30 minutes. Evaporation of the filtered solution afforded 7.11 g of the title compound.

δ (CDCl$_3$) 7.18–7.57 (4H, m); 7.31, 8.15 (4H, AA'BB', J=9 Hz).

EXAMPLE 21

S-(4-Fluorophenyl) 4-(chlorothiocarbonyloxy)thiobenzoate

A solution of sodium hydroxide (1.20 g) in 5 ml of water was added dropwise over 10 minutes to a vigorously stirred solution of 6.30 g of S-(4-fluorophenyl) 4-(hydroxy)thiobenzoate and 2.90 ml of thiophosgene in 100 ml of chloroform cooled to 10° C. Stirring was continued for 2 hours at room temperature and the filtered solution stirred a further 30 minutes with calcium chloride. Evaporation of the filtered solution gave 3.41 g of the title compound.

$\nu_{max}$ (film) 1669 cm$^{-1}$.

δ (CDCl$_3$) 6.88–7.61 (4H, m); 7.19, 8.05 (4H, AA'BB', J=9 Hz).

EXAMPLE 22

S-(4-Methoxyphenyl) 4(chlorothiocarbonyloxy)thiobenzoate

A solution of sodium hydroxide (1.01 g) in 2 ml of water was added to a cool (10° C. or below) solution of 5.50 g of S-(4-methoxyphenyl) 4-(hydroxy)thiobenzoate and 2.42 ml of thiophosgene in 75 ml of chloroform. Vigorous stirring was continued for 2 hours at room temperature and the filtered solution treated with calcium chloride for a further 30 minutes. Evaporation of the filtered solution and chromatography of the residue on silica gel using hexane/ethyl acetate mixtures as eluant gave 2.75 g of the title compound.

$\nu_{max}$ (film) 1670 cm$^{-1}$.

δ (CDCl$_3$) 3.74 (3H, s); 6.75–7.52 (6H, m); 7.85–8.28 (2H, m).

EXAMPLE 23

S-(4-Cyanophenyl) 4-(chlorothiocarbonyloxy)thiobenzoate

A solution of 566 mg of sodium hydroxide in 5 ml of water was added dropwise with vigorous stirring to a solution of 3.00 g of S-(4-cyanophenyl) 4-(hydroxy)thiobenzoate and 1.35 ml of thiophosgene in 60 ml of chloroform. Stirring was continued for 2 hours when the filtered solution was treated with calcium chloride and stirred for a further 30 minutes. Evaporation of the filtered solution gave 3.66 g of the title compound.

$\nu_{max}$ (film) 2225, 1674 cm$^{-1}$.

δ (CDCl$_3$) 7.26, 8.20 (4H, AA'BB', J=9 Hz); 7.40–7.85 (4H, m).

EXAMPLE 24

S-(2-Methylprop-2-yl) (4-chlorothiocarbonyloxy)thiobenzoate

A solution of S-(2-methylprop-2-yl) 4-(hydroxy)thiobenzoate (1.55 g) in dry benzene (30 ml) was added over 5 minutes to a vigorously stirred suspension of finely powdered sodium hydroxide (295 mg) in dry benzene (30 ml) and stirring continued for 2 hours at room temperature. Thiophosgene (0.84 ml) was added in one portion and stirring continued for a further 1.5 hours. Evaporation of the filtered solution gave the title compound as a pale yellow gum (1.92 g).

$\nu_{max}$ (film) 1661, 1600 cm$^{-1}$.

δ (CDCl$_3$) 1.63 (9H, s); 7.25, 8.07, (4H, AA'BB', J=8.9 Hz).

EXAMPLE 25

4-Nitrobenzyl 2-[3(S)-(1(R)-dimethyl-(2-methylprop-2-yl)silyloxyethyl)-4(R)-ethylthioazetidin-2-on-1-yl]-3-[4-(2,4,5-trichlorophenylthio-(carbonyl))-phenoxy]-3-trimethylacetylthiopropenoate To a stirred solution of 4-nitrobenzyl 2-[3(S)-(1(R)-dimethyl-(2-methylprop-2-yl)-silyloxyethyl)-4(R)-ethylthioazetidin-2-on-1-yl]acetate (3.60 g) and S-(2,4,5-trichlorophenyl) 4-(chlorothiocarbonyloxy)thiobenzoate (3.69 g) in dry tetrahydrofuran at −40° C. under argon was added a solution of a mixture of 3.93 ml of hexamethyldisilazane and 11.7 ml of a 1.60 molar hexane solution of n-butyllithium in dry tetrahydrofuran. The mixture was stirred at −40° C. for 20 minutes and 1.98 ml of trimethylacetyl bromide was added. After stirring at −40° C. for a further hour, the mixture was poured into cold 0.1 molar aqueous hydrochloric acid and extracted with ether. The combined organic layers were washed with saturated sodium bicarbonate, with brine, and were then dried over magnesium sulphate and evaporated to dryness.

Chromatography over silica gel, eluting with hexane/ethyl acetate mixtures afforded the title compound as a yellow gum (4.29 g).

$\nu_{max}$ (film) 1767 cm$^{-1}$.

δ (CDCl$_3$) 0.02, 0.07 (6H, 2s); 0.80, 0.88 (9H, 2s); 1.06, 1.14 (9H, 2s); 1.14–1.44 (6H, m); 2.52–2.84 (2H, m); 3.20–3.29 (1H, m); 4.20–4.38 (1H, m); 5.21–5.54 (3H, m); 7.10–7.82 (6H, m); 7.94–8.26 (4H, m).

EXAMPLE 26

4-Nitrobenzyl 2-[3(S)-(1(R)-dimethyl-(2-methylprop-2-yl)silyloxyethyl)-4(R)-ethylthioazetidin-2-on-1-yl]-3-[4-(pentafluorophenylthio-(carbonyl))-phenoxy]-3-trimethylacetylthiopropenoate 8.34 g of the title compound were obtained by a procedure analogous to that described in Example 25 using 8.63 g of 4-nitrobenzyl 2-[3(S)-(1(R)-dimethyl-(2-methylprop-2-yl)-silyloxyethyl)-4(R)-ethylthioazetidin-2-on-1-yl]acetate; 9.43 ml of hexamethyldisilazane; 7.87 g of S-(pentafluorophenyl) 4-(chlorothiocarbonyloxy)-thiobenzoate; 44.7 mmol of n-butyllithium; and 4.75 ml of trimethylacetyl bromide.

δ (CDCl$_3$) 0.05, 0.06 (6H, 2s); 0.82, 0.88 (9H, 2s); 1.24 (9H, s); 1.07–1.40 (6H, m); 2.45–2.60 (2H, m); 3.10–3.25 (1H, m); 4.15–4.35 (1H, m); 5.20–5.55 (3H, m); 6.94–7.94 (4H, AA'BB', J=8.8 Hz); 7.54–8.24 (4H, AA'BB', J=8.8 Hz).

EXAMPLE 27

4-Nitrobenzyl 2-[3(S)-(1(R)-dimethyl-(2-methylprop-2-yl)silyloxyethyl)-4(R)-ethylthioazetidin-2-on-1-yl]-3-[4-(phenylthio-(carbonyl))-phenoxy]-3-trimethylacetylthiopropenoate 695 mg of the title compound were obtained by a procedure analogous to that described in Example 25 using 540 mg of 4-nitrobenzyl 2-[3(S)-(1(R)-dimethyl-(2-methylprop-2-yl)-silyloxyethyl)-4(R)-ethylthioazetidin-2-on-1-yl]acetate; 0.532 ml of hexamethyldisilazane; 415 mg of S-phenyl 4-(chlorothiocarbonyloxy)thiobenzoate; 2.52 mmol of n-butyllithium: and 0.3 ml of trimethylacetyl bromide.

δ (CDCl$_3$) 0.01, 0.02 (6H, 2s); 0.77, 0.83 (9H, 2s); 1.03, 1.11 (9H, 2s); 1.15–1.50 (6H, m); 2.50–2.85 (2H, m); 3.15–3.25 (1H, m); 4.15–4.25 (1H, m); 5.20–5.45 (3H, m); 6.85–7.60 (9H, m); 7.90–8.25 (4H, m).

EXAMPLE 28

4Nitrobenzyl 3-[4-(4-chlorophenylthio-(carbonyl))phenoxy]-2-[3(S)-(1(R)-dimethyl-(2-methylprop-2-yl)-silyloxyethyl)-4(R)-ethylthioazetidin-2-on-1-yl]-3-trimethylacetylthiopropenoate 7.38 g of the title compound were obtained by a procedure analogous to that described in Example 25 using 4.60 g of 4-nitrobenzyl 2-[3(S)-(1(R)-dimethyl-(2-methylprop-2-yl)-silyloxyethyl)-4(R)-ethylthioazetidin-2-on-1-yl]acetate; 4.52 ml of hexamethyldisilazane; 3.52 g of S-(4-chlorophenyl) 4-(chlorothiocarbonyloxy)-thiobenzoate; 21.4 mmol of n-butyllithium; and 2.53 ml of trimethylacetyl bromide.

δ (CDCl$_3$) 0.01, 0.02 (6H, 2s); 0.80, 0.88 (9H, 2s); 1.05, 1.06 (9H, 2s); 1.20–1.40 (6H, m); 2.55–2.95 (2H, m); 3.23 (1H, dd, J=3.3 Hz and 6.2 Hz); 4.15–4.40 (1H, m); 5.20–5.45 (3H, m); 7.10–7.65 (8H, m); 7.95–8.30 (4H, m).

EXAMPLE 29

4-Nitrobenzyl 2-[3(S)-(1(R)-dimethyl-(2-methylprop-2-yl)silyloxyethyl)-4(R)-ethylthioazetidin-2-on-1-yl]-3-[4-(4-fluorophenylthio-(carbonyl))-phenoxy]-3-trimethylacetylthiopropenoate 4.86 g of the title compound were obtained by a procedure analogous to that described in Example 25 using 4.63 g of 4-nitrobenzyl 2-[3(S)-(1(R)-dimethyl-(2-methlprop-2-yl)-silyloxyethyl-4(R)-ethylthioazetidin-2-on-1-yl]acetate; 4.55 ml of hexamethyldisilazane; 3.27 mg of S-(4-fluorophenyl) 4-(chlorothiocarbonyloxy)-thiobenzoate; 21.6 mmol of n-butyllithium; and 2.55 ml of trimethylacetyl bromide.

δ (CDCl$_3$) 0.04, 0.06 (6H, 2s); 0.80, 0.87 (9H, 2s); 1.04, 1.10 (9H, 2s); 1.18–1.38 (6H, m); 2.48–2.90 (2H, m); 3.14–3.29 (1H, m); 4.15–4.43 (1H, m); 5.16–5.48 (3H, m); 7.01–7.61 (8H, m); 7.95–8.30 (4H, m).

EXAMPLE 30

4-Nitrobenzyl 2-[3(S)-(1(R)-dimethyl-(2-methylprop-2-yl)silyloxyethyl)-4(R)-ethylthioazetidin-2-on-1-yl]-3-[4-(4-methoxyphenylthio-(carbonyl))-phenoxy]-3-trimethylacetylthiopropenoate 4.66 g of the title compound were obtained by a procedure analogous to that described in Example 25 using 3.56 g of 4-nitrobenzyl 2-[3(S)-(1(R)-dimethyl-(2-methylprop-2-yl)-silyloxyethyl)-4(R)-ethylthioazetidin-2-on-1-yl]acetate; 3.37 ml of hexamethyldisilazane; 2.75 g of S-(4-methoxyphenyl) 4-(chlorothiocarbonyloxy)-thiobenzoate; 16 mmol of n-butyllithium; and 2.31 g of trimethylacetyl bromide.

δ (CDCl$_3$) 0.01, 0.03 (6H, 2s); 1.06, 1.14 (9H, 2s); 1.20–1.40 (6H, m); 2.55–2.85 (2H, m); 3.23 (1H, dd, J=2.6 Hz and 6.3 Hz); 3.84–3.86 (3H, 2s); 4.20–4.35 (1H, m); 5.20–5.50 (3H, m); 7.00–7.65 (8H, m); 7.90–8.30 (4H, m).

EXAMPLE 31

4-Nitrobenzyl 3-[4-(4-cyanophenylthio-(carbonyl))phenoxy]-2-[3(S)-(1(R)-dimethyl-(2-methylprop-2-yl)-silyloxyethyl)-4(R)-ethylthioazetidin-2-on-1-yl]-3-trimethylacetylthiopropenoate 2.67 g of the title compound were obtained by a procedure analogous to that described in Example 25 using 2.62 g of 4-nitrobenzyl 2-[3(S)-(1(R)-dimethyl-(2-methylprop-2-yl)-silyloxyethyl)-4(R)-ethylthioazetidin-2-on-1-yl]acetate; 3.20 ml of hexamethyldisilazane; 2.18 g of S-(4-cyanophenyl) 4-(chlorothiocarbonyloxy)-thiobenzoate; 15.3 mmol of n-butyllithium; and 1.80 g of trimethylacetyl bromide.

δ (CDCl$_3$) 0.04, 0.06 (6H, 2s); 0.77, 0.83 (9H, 2s); 1.07, 1.13 (9H, 2s); 1.18–1.40 (6H, m); 2.45–2.90 (2H, m); 3.10–3.28 (1H, m); 4.15–4.33 (1H, m); 5.15–5.50 (3H, m); 6.80–7.48 (8H, m); 7.67–8.20 (4H, m).

EXAMPLE 32

4-Nitrobenzyl 2-[3(S)-(1(R)-dimethyl-(2-methylprop-2-yl)silyloxyethyl)-4(R)-ethylthioazetidin-2-on-1-yl]-3-[4-((2-methylprop-2-yl)thio-(carbonyl))-phenoxy]-3-trimethylacetylthiopropeonate 3.92 g of the title compound were obtained by a procedure analogous to that described in Example 25 using 5.00 g of 4-nitrobenzyl 2-[3(S)-(1(R)-dimethyl-(2-methylprop-2-yl)-silyloxyethyl)-4(R)-ethylthioazetidin-2-on-1-yl]acetate; 5.47 ml of hexamethyldisilazane; 3.88 g of S-(2-methylprop-2-yl) 4-(chlorothiocarbonyloxy)-thiobenzoate; 25.9 mmol of n-butyllithium; and 1.99 ml of trimethylacetyl bromide.

δ (CDCl$_3$) 0.01, 0.06 (6H, 2s); 0.79, 0.86 (9H, 2s); 1.04, 1.11 (9H, 2s); 1.15–1.35 (6H, m); 1.57, 1.58 (9H, 2s); 2.54–2.88 (2H, m); 3.17–3.27 (1H, m); 4.15–4.40 (1H, m); 5.20–5.45 (3H, m); 7.04–7.88 (4H, AA'BB', J=8.8 Hz); 7.57–8.23 (4H, AA'BB', J=8.7 Hz).

EXAMPLE 33

4-Nitrobenzyl 2-[4(R)-ethylthio-3(S)-(1(R)-hydroxyethyl)azetidin-2-on-1-yl]-3-[4-(2,4,5-trichlorophenylthio(carbonyl))-phenoxy]-3-trimethylacetylthiopropenoate To a stirred solution of 3.03 g of 4-nitrobenzyl 2-[3(S)-(1(R)-dimethyl-(2-methylprop-2-yl)-silyloxyethyl)-4(R)-ethylthioazetidin-2-on-1-yl]-3-[4-(2,4,5-trichlorophenyltio-(carbonyl))-phenoxy]-3-trimethylacetylthiopropenoate in 47 ml of tetrahydrofuran at room temperature was added 2.34 ml of water and 2.34 ml of concentrated hydrochloric acid. The mixture was stirred until t.l.c. showed the reaction to be complete. The mixture was partitioned between ethyl acetate and water, the separated organic layer washed with sodium bicarbonate solution and brine and dried over magnesium sulphate. Evaporation of the filtered solution followed by chromatography of the residue (silica gel, ethyl acetate/hexane mixtures as eluant) afforded the title compound (1.27 g) as a yellow oil.

The product is isolated as a mixture of E and Z isomers, observed as double peaks in the nmr spectrum. The E and Z isomers are separable by chromatography if required.

δ (CDCl$_3$) 1.09 (9H, s); 1.27 (3H, t, J=7.6 Hz); 1.29 (3H, d, J=6.1 Hz); 1.68 (1H, broad s); 2.63–2.82 (2H, m); 3.25 (1H, dd, J=2.6 Hz and 4.9 Hz); 4.15–4.35 (1H, m); 5.24 (1H, d, J=2.6 Hz); 5.28, 5.39 (2H, ABq, J=13.5 Hz); 7.16, 7.99 (4H, AA'BB', J=8.8 Hz); 7.60, 8.25 (4H, AA'BB', J=8.8 Hz); 7.68 (1H, s); 7.70 (1H, s).

Small signals due to the other propenoate isomer could also be seen in the $^1$H n.m.r. spectrum.

EXAMPLE 34

4-Nitrobenzyl 2-[4(R)-ethylthio-3(S)-(1(R)-hydroxyethyl)azetidin-2-on-1-yl]-3-[4-(pentafluorophenylthio(carbonyl))-phenoxy]-3-trimethylacetylthiopropenoate 3.03 g of the above compound were obtained from 5.62 g of the corresponding [1(R)-dimethyl-(2-methylprop-2-yl)silyloxyethyl] compound (see Example 26) by a procedure analogous to that described in Example 33, using 4.5 ml of water and 4.5 ml of concentrated hydrochloric acid.

ν$_{max}$ (film) 3480, 1783 cm$^{-1}$.

δ (CDCl$_3$) 1.10 (9H, s); 1.27 (3H, t, J=7.6 Hz); 1.29 (3H, d, J=6.5 Hz); 1.62 (1H, broad s); 2.55–2.80 (2H, m); 3.26 (1H, dd, J=2.7 Hz and 4.8 Hz); 4.10–4.30 (1H, m); 5.25 (1H, d, J=2.7 Hz); 5.30, 5.39 (2H, ABq, J=13.4 Hz); 7.18, 8.00 (4H, AA'BB', J=8.8 Hz); 7.60, 8.24 (4H, AA'BB', J=8.6 Hz).

EXAMPLE 35

4-Nitrobenzyl 2-[4(R)-ethylthio-3(S)-(1(R)-hydroxyethyl)azetidin-2-on-1-yl]-3-[4-(phenylthio-(carbonyl))-phenoxy]-3-trimethylacetylpropenoate 2.32 g of the above compound were obtained from 5.04 g of the corresponding [1(R)-dimethyl-(2-methylprop-2-yl)silyloxyethyl] compound (see Example 27) by a procedure analogous to that described in Example 33, using 5 ml of water and 5 ml of concentrated hydrochloric acid.

δ (CDCl$_3$) 1.12, 1.19 (9H, s); 1.25–1.45 (6H, m); 1.68, 1.80 (1H, 2d, broad s); 2.67–2.90 (2H, m); 3.27–3.33 (1H, m); 4.22–4.50 (1H, m); 5.25–5.47 (3H, m); 7.08–7.68 (9H, m); 7.99–8.35 (4H, m).

EXAMPLE 36

4-Nitrobenzyl 3-[4-(4-chlorophenylthio-(carbonyl))phenoxy]-2-[4(R)-ethylthio-3(S)-(1(R)-hydroxyethyl)-azetidin-2-on-1-yl]-3-trimethylacetylthiopropenoate 2.10 g of the above compound were obtained from 4.96 g of the corresponding [1(R)-dimethyl-(2-methylprop-2-yl)silyloxyethyl] compound (see Example 28) by a procedure analogous to that described in Example 33, using 5 ml of water and 5 ml of concentrated hydrochloric acid.

ν$_{max}$ (film) 3420, 1760 cm$^{-1}$.

δ (CDCl$_3$) 1.07 (9H, s); 1.27 (3H, t, J=7.2 Hz); 1.28 (3H, d, J=6.2 Hz); 1.62 (1H, broad s); 2.62–2.85 (2H, m); 3.25 (1H, dd, J=2.7 Hz and 4.9 Hz); 4.15–4.25 (1H, m); 5.25 (1H, d, J=2.7 Hz); 5.29, 5.38 (2H, ABq, J=13.8 Hz); 7.14, 7.98 (4H, AA'BB', J=8.8 Hz); 7.38–7.48 (4H, m); 7.60, 8.24 (4H, AA'BB', J=8.8 Hz).

EXAMPLE 37

4-Nitrobenzyl 2-[4(R)-ethylthio-3(S)-(1(R)-hydroxyethyl)azetidin-2-on-1-yl]-3-[4-(4-fluorophenylthio(carbonyl))-phenoxy]-3-trimethylacetylthiopropenoate 2.32 g of the above compound were obtained from 4.86 g of the corresponding [1(R)-dimethyl-(2-methylprop-2-yl)silyloxyethyl] compound (see Example 29) by a procedure analogous to that described in Example 33, using 5 ml of water and 5 ml of concentrated hydrochloric acid.

$\nu_{max}$ (film) 3440, 1760 cm$^{-1}$.

δ (CDCl$_3$) 1.08, 1.15 (9H, 2s); 1.20–1.38 (6H, m); 1.66 (1H, broad s); 2.60–2.84 (2H, m); 3.22–3.34 (1H, m); 4.15–4.40 (1H, m); 5.17, 5.26 (1H, 2d, J=2.7 Hz); 5.25–5.44 (2H, m); 7.03–7.65 (8H, m); 7.99–8.30 (4H, m).

EXAMPLE 38

4-Nitrobenzyl 2-[4(R)-ethylthio-3(S)-(1(R)-hydroxyethyl)azetidin-2-on-1-yl]-3-[4-(4-methoxyphenylthio(carbonyl))-phenoxy]-3-trimethylacetylthiopropenoate 2.80 g of the above compound were obtained from 4.66 g of the corresponding [1(R)-dimethyl-(2-methylprop-2-yl)silyloxyethyl] compound (see Example 30) by a procedure analogous to that described in Example 33, using 5 ml of water and 5 ml of concentrated hydrochloric acid.

δ (CDCl$_3$) 1.12, 1.15 (9H, 2s); 1.18–1.60 (6H, m); 2.03 (1H, broad s); 2.47–2.84 (2H, m); 3.15–3.38 (1H, m); 3.80, 3.81 (3H, 2s, OCH$_3$); 3.96–4.37 (1H, m); 5.18–5.44 (3H, m); 6.81–7.71 (8H, m); 7.76–8.34 (4H, m).

EXAMPLE 39

4-Nitrobenzyl 3-[4-(4-cyanophenylthio-(carbonyl))phenoxy]-2-[4(R)-ethylthio-3(S)-(1(R)-hydroxyethyl)-azetidin-2-on-1yl]-3-trimethylacetylthiopropenoate 2.79 g of the above compound were obtained from 5.12 g of the corresponding [1(R)-dimethyl-(2-methylprop-2-yl)silyloxyethyl] compound (see Example 31) by a procedure analogous to that described in Example 33, using 5 ml of water and 5 ml of concentrated hydrochloric acid.

$\nu_{max}$ (film) 3450, 2223, 1765 cm$^{-1}$.

δ (CDCl$_3$) 1.08 (9H, 2s); 1.22–1.45 (6H, m); 1.94 (1H, broad s); 2.64–2.87 (2H, m); 3.19–3.37 (1H, m); 4.03–4.31 (1H, m); 5.16–5.45 (3H, m); 6.97–7.70 (8H, m); 7.84–8.27 (4H, m).

EXAMPLE 40

4-Nitrobenzyl 2-[4(R)-ethylthio-3(S)-(1(R)-hydroxyethyl)azetidin-2-on-1-yl]-3-[4-((2-methylprop-2-yl)thio(carbonyl))-phenoxy]-3-trimethylacetylthiopropenoate 1.54 g of the above compound were obtained from 3.14 g of the corresponding [1(R)-dimethyl-(2-methylprop-2-yl)silyloxyethyl] compound (see Example 32) by a procedure analogous to that described in Example 33, using 3 ml of water and 3 ml of concentrated hydrochloric acid.

$\nu_{max}$ (film) 3490, 1770 cm$^{-2}$.

δ (CDCl$_3$) 1.03, 1.10 (9H, 2s); 1.23 (3H, t, J=7.6 Hz); 1.25 (3H, d, J=6.2 Hz); 1.54, 1.55 (9H, 2s); 1.68 (1H, broad s); 2.60–2.78 (2H, m); 3.21 (1H, dd, J=2.6 Hz and 5.0 Hz); 4.05–4.20 (1H, m); 5.21 (1H, d, J=2.6 Hz); 5.25, 5.35 (2H, ABq, J=13.5 Hz); 7.03, 7.86 (4H, AA'BB', J=8.8 Hz); 7.56, 8.21 (4H, AA'BB', J=8.8 Hz).

Other smaller signals due to the alternative isomer were also present but are not quoted.

EXAMPLE 41

4-Nitrobenzyl 2-[4(S)-chloro-3(S)-(1(R)-hydroxyethyl)azetidin-2-on-1-yl]-3-[4-(2,4,5-trichlorophenylthio(carbonyl))-phenoxy]-3-trimethylacetylthiopropenoate To a stirred solution of 1.26 g of 4-nitrobenzyl 2-[4(R)-ethylthio-3(S)-(1(R)-hydroxyethyl)-azetidin-2-on-1-yl]-3-[4-(2,4,5-trichlorophenylthio-(carbonyl))-phenoxy]-3-trimethylacetylthiopropenoate in 30 ml of dry chloroform at −40° C. was added a solution of 1.83 mmol chlorine in 4 ml of carbon tetrachloride, and the solution was stirred for 30 minutes. The reaction mixture was allowed to reach room temperature and evaporated to dryness. Chromatography of the residue (silica gel, hexane/ethyl acetate mixtures as eluant) gave the title compound as a pale yellow foam (0.706 g). $\nu_{max}$ (CHCl$_3$) 1784 cm$^{-1}$.

δ (CDCl$_3$) 1.08, 1.09 (9H, 2s); 1.39 (3H, d, J=6.3 Hz); 2.26 (1H, d, broad s); 3.53, 3.77 (1H, 2dd, J=4.3 Hz and 9.7 Hz); 4.25–4.45 (1H, m); 5.33 (2H, apparent s); 6.10, 6.13 (1H, 2d, J=4.3 Hz); 7.06–7.78 (6H, m); 7.90–8.29 (4H, m).

EXAMPLE 42

4Nitrobenzyl 2-[4(S)-chloro-3(S)-(1(R)-hydroxyethyl)azetidin-2-on-1-yl]-3-[4-(pentafluorophenylthio(carbonyl))-phenoxy]-3-trimethylacetylthiopropenoate 0.82 g of the above compound was obtained by a procedure analogous to that described in Example 41, using 1.14 g of the 1(R)-hydroxyethylazetidinone derivative defined in Example 34 and a solution of 1.56 mmol of chlorine in carbon tetrachloride.

$\nu_{max}$ (CHCl$_3$) 1783 cm$^{-1}$.

δ (CDCl$_3$) 1.10 (9H, s); 1.39 (3H, d, J=6.4 Hz); 1.61 (1H, broad s); 3.54 (1H, dd, J=4.4 Hz and 9.5 Hz); 4.25–4.40 (1H, m); 5.33 (2H, apparent s); 6.13 (1H, d, J=4.4 Hz); 7.16, 8.02 (4H, AA'BB', J=8.8 Hz); 7.57, 8.25 (4H, AA'BB', J=8.8 Hz).

EXAMPLE 43

4-Nitrobenzyl 2-[4(S)-chloro-3(S)-(1(R)-hydroxyethyl)azetidin-2-on-1-yl]-3-[4-(phenylthio-(carbonyl))-phenoxy]-3-trimethylacetylthipropenoate 1.98 g of the above compound was obtained by a procedure analogous to that described in Example 41, using 2.75 g of the 1(R)-hydroxyethylazetidinone derivative defined in Example 35 and a solution of 4.17 mmol of chlorine in carbon tetrachloride.

δ (CDCl$_3$) 1.09 (9H, s); 1.41 (3H, d, J=6.3 Hz); 2.30 (1H, broad s); 3.54 (1H, dd, J=4.3 Hz and 9.6 Hz); 4.27–4.40 (1H, m); 5.34 (2H, apparent s); 6.16 (1H, d, J=4.3 Hz); 7.08–7.63 (9H, m); 7.98–8.28 (4H, m).

EXAMPLE 44

4-Nitrobenzyl 2-[4(S)-chloro-3(S)-(1(R)-hydroxyethyl)azetidin-2-on-1-yl]-3-[4-(4-chlorophenylthio-(carbonyl))phenoxy]-3-trimethylacetylthiopropenoate 1.60 g of the above compound was obtained by a procedure analogous to that described in Example 41, using 2.11 g of the 1(R)-hydroxyethylazetidinone derivative defined in Example 36 and a solution of 3.30 mmol of chloride in carbon tetrachloride.

δ ($CDCl_3$) 1.08 (9H, s); 1.39 (3H, d, J=6.3 Hz); 1.61 (1H, broad s); 3.53 (1H, dd, J=4.3 Hz and 9.6 Hz); 4.25–4.40 (1H, m); 5.33 (2H, apparent s); 6.14 (1H, d, J=4.3 Hz); 7.13, 8.01 (4H, AA'BB', J=8.8 Hz); 7.40–7.50 (4H, m); 7.56, 8.25 (4H, AA'BB', J=8.7 Hz).

EXAMPLE 45

4-Nitrobenzyl 2-[4(S)-chloro-3(S)-(1(R)-hydroxyethyl)azetidin-2-on-1-yl]-3-[4-(4-fluorophenylthio-(carbonyl))phenoxy]-3-trimethylacetylthiopropenoate 1.54 g of the above compound was obtained by a procedure analogous to that described in Example 41, using 2.32 g of the 1(R)-hydroxyethylazetidinone derivative defined in Example 37 and a solution of 3.10 mmol of chlorine in carbon tetrachloride.

δ ($CDCl_3$) 1.07, 1.08 (9H, 2s); 1.30–1.45 (3H, m); 1.63 (1H, broad s); 3.49–3.58 (1H, m); 4.12–4.43 (1H, m); 5.25–5.38 (2H, m); 6.11, 6.13 (1H, 2d, J=4.3 Hz); 7.08–7.29 (4H, m); 7.40–7.64 (4H, m); 7.94–8.29 (4H, m).

EXAMPLE 46

4Nitrobenzyl 2-[4(S)-chloro-3(S)-(1(R)-hydroxyethyl)azetidin-2-on-1-yl]-3-[4-(4-methoxyphenylthio-(carbonyl))phenoxy]-3-trimethylacetylthiopropenoate 1.19 g of the above compound was obtained by a procedure analogous to that described in Example 41, using 1.80 g of the 1(R)-hydroxyethylazetidinone derivative defined in Example 38 and a solution of 2.38 mmol of chlorine in carbon tetrachloride.

δ ($CDCl_3$) 1.07, 1.12 (9H, 2s); 1.40 (3H, d, J=6.3 Hz); 2.28–2.36 (1H, broad s); 3.48–3.62 (1H, m); 3.84, 3.85 (3H, 2s); 4.25–4.40 (1H, m); 5.32 (2H, apparent s); 6.14, 6.16 (1H, 2d, J=4.3 Hz); 6.98–7.63 (8H, m); 7.94–8.30 (4H, m).

EXAMPLE 47

4-Nitrobenzyl 2-[4(S)-chloro-3(S)-(1(R)-hydroxyethyl)azetidin-2-on-1-yl]-3-[4-(4-cyanophenylthio-(carbonyl))phenoxy]-3-trimethylacetylthiopropenoate 0.78 g of the above compound was obtained by a procedure analogous to that described in Example 41, using 1.38 g of the 1(R)-hydroxyethylazetidinone derivative defined in Example 39 and a solution of 2.02 mmol of chlorine in carbon tetrachloride.

δ ($CDCl_3$) 1.07, 1.09 (9H, 2s); 1.34–1.44 (3H, m); 2.20 (1H, broad s); 3.49–3.57 (1H, m); 4.25–4.40 (1H, m); 5.33 (2H, apparent s); 6.13, 6.11 (1H, 2d, J=4.3 Hz); 7.04–7.72 (8H, m); 7.94–8.29 (4H, m).

EXAMPLE 48

4-Nitrobenzyl 2-[4(S)-chloro-3(S)-(1(R)-hydroxyethyl)azetidin-2-on-1-yl]-3-[4-((2-methylprop-2-yl)thio(carbonyl))phenoxy]-3-trimethylacetylthiopropenoate 1.01 g of the above compound was obtained by a procedure analogous to that described in Example 41, using 1.36 g of the 1(R)-hydroxyethylazetidinone derivative defined in Example 40 and a solution of 2.14 mmol of chlorine in carbon tetrachloride.

δ ($CDCl_3$) 1.07, 1.09 (9H, 2s); 1.38, 1.40 (3H, 2d, J=6.3 Hz); 1.57, 1.59 (9H, 2s); 2.26 (1H, broad s); 3.48–3.58 (1H, m); 4.24–4.40 (1H, m); 5.24–5.39 (2H, m); 6.12, 6.15 (1H, 2d, J=4.3 Hz); 7.01–8.30 (8H, m).

EXAMPLE 49

4-Nitrobenzyl 5(R),6(S)-[1(R)-hydroxyethyl]-7-oxo-3-[4-(2,4,5-trichlorophenylthio-(carbonyl))phenoxy]-4-thia-1-azabicyclo[3.2.0]hept-2-ene-2-carboxylate 66 mg of imidazole was added to a stirred solution of 703 mg of 4-nitrobenzyl 2-[4(S)-chloro-3(S)-(1(R)-hydroxyethyl)-azetidin-2-on-1-yl]-3-[4-(2,4,5-trichlorophenylthio-(carbonyl))-phenoxy]-3-trimethylacetylthiopropenoate in dioxan-water (9:1 v/v) at 5° C. Stirring was continued for 30 minutes and the mixture was then allowed to reach room temperature and was partitioned between ethyl acetate and water. The organic layer was washed with cold dilute hydrochloric acid, saturated sodium bicarbonate and brine, dried over magnesium sulphate and evaporated in vacuo to dryness. Chromatography of the residue over silica gel and eluting with hexane/ethyl acetate mixtures afforded the title compound (327 mg) as a yellow foam.

$v_{max}$ ($CDCl_3$) 1780 $cm^{-1}$.

δ ($CDCl_3$) 1.40 (3H, d, J=6.3 Hz); 1.88 (1H, broad s); 3.85 (1H, d, J=1.4 Hz and 6.6 Hz); 4.22–4.38 (1H, m); 5.22,5.41 (2H, ABq, J=13.6 Hz); 5.73 (1, d, J=1.4 Hz); 7.24,8.04 (4H, AA'BB', J=8.8 Hz); 7.51,8.19 (4H, AA'BB', J=8.8 Hz); 7.69 (1H, s); 7.72 (1H, s)

EXAMPLE 50

4-Nitrobenzyl 5(R),6(S)-[1(R)-hydroxyethyl]-7-oxo-3-[4-(pentafluorophenylthio-(carbonyl))phenoxy]-4-thia-1-azabicyclo[3.2.0]hept-2-ene-2-carboxylate 423 mg of the above compound were obtained by a procedure analogous to that described in Example 49, using 820 mg of the 4(S)-chloroazetidinone derivative defined in Example 42, and 78 mg of imidazole.

$v_{max}$ ($CDCl_3$) 1790 $cm^{-1}$.

δ ($CDCl_3$) 1.39 (3H, d, J=6.3 Hz); 1.87 (1H, broad s); 3.85 (1H, dd, J=1.4 Hz and 6.6 Hz); 4.25–4.38 (1H, m); 5.21,5.40 (2H, ABq, J=13.7 Hz); 5.71 (1H, d, J=1.4 Hz); 7.26,8.04 (4H, AA'BB', J=8.8 Hz); 7.51,8.19 (4H, AA'BB', J=8.8 Hz).

EXAMPLE 51

4-Nitrobenzyl 5(R),6(S)-[1(R)-hydroxyethyl]-7-oxo-3-[4(phenylthio-(carbonyl))phenoxy]-4-thia-1-azabicyclo[3.2.0]hept-2-ene-2-carboxylate 3.24 g of the above compound were obtained by a procedure analogous to that described in Example 49, using 5.06 g of the 4(S)-chloroazetidinone derivative defined in Example 43, and 0.542 g of imidazole.

$\nu_{max}$ (CDCl$_3$) 1786 cm$^{-1}$.

δ (CDCl$_3$) 1.39 (3H, d, J=6.3 Hz); 1.80 (1H, broad s); 3.83 (1H, dd, J=1.1 Hz and 6.7 Hz); 4.23–4.44 (1H, m); 5.22,5.41 (2H, ABq, J=13.7 Hz); 5.71 (1H, d, J=1.1 Hz); 7.22,8.05 (4H, AA'BB', J=8.8 Hz); 7.52,8.19 (4H, AA'BB', J=8.7 Hz); 7.40–7.54 (5H, m).

EXAMPLE 52

4-Nitrobenzyl 5(R),3-[4-(4-chlorophenylthio-(carbonyl))phenoxy]-6(S)-[1(R)-hydroxyethyl]-7-oxo-4-thia-1-azabicyclo[3.2.0]hept-2-ene-2-carboxylate 1.02 g of the above compound were obtained by a procedure analogous to that described in Example 49, using 1.60 g of the 4(S)-chloroazetidinone derivative defined in Example 44, and 0.163 g of imidazole.

$\nu_{max}$ (CDCl$_3$) 1784 cm$^{-1}$.

δ (d$_6$-DMSO) 1.18 (3H, d, J=6.1 Hz); 3.98 (1H, dd, J=1.32 Hz and 5.7 Hz); 3.95–4.09 (1H, m); 5.25,5.36 (2H, ABq, J=13.4 Hz); 5.83 (1H, d, J=1.3 Hz); 7.44,7.99 (4H, AA'BB', J=8.8 Hz); 7.44–7.65 (4H, m); 7.52,8.16 (4H, AA'BB', J=8.8 Hz).

EXAMPLE 53

4-Nitrobenzyl 5(R),3-[4-(4-fluorophenylthio-(carbonyl))phenoxy]-6(S)-[1(R)-hydroxyethyl]-7-oxo-4-thia-1-azabicyclo[3.2.0]hept-2-ene-2-carboxylate 0.574 g of the above compound were obtained by a procedure analogous to that described in Example 49, using 1.54 g of the 4(S)-chloroazetidinone derivative defined in Example 45, and 160 mg of imidazole.

$\nu_{max}$ (CDCl$_3$) 1780 cm$^{-1}$.

δ (d$_6$-acetone) 1.31 (3H, d, J=6.3 Hz); 3.98 (1H, dd, J=1.4 Hz and 6.2 Hz); 4.18–4.34 (1H, m); 4.42 (1H, d, J=3.9 Hz); 5.27,5.41 (2H, ABq, J=13.8 Hz); 5.92 (1H, d, J=1.4 Hz); 7.22–7.68 (8H, m); 8.00–8.24 (4H, m).

EXAMPLE 54

4-Nitrobenzyl 5(R),6(S)-[1(R)-hydroxyethyl]-3-[4-(4-methoxyphenylthio-(carbonyl))phenoxy]-7-oxo-4-thia-1-azabicyclo[3.2.0]hept-2-ene-2-carboxylate 0.629 g of the above compound were obtained by a procedure analogous to that described in Example 49, using 1.19 g of the 4(S)-chloroazetidinone derivative defined in Example 46, and 122 mg of imidazole.

$\nu_{max}$ (CDCl$_3$) 1789 cm$^{-1}$.

δ (CDCl$_3$) 1.39 (3H, d, J=6.3 Hz); 3.84 (3H, s); 3.82 (1H, dd, J=1.4 Hz and 6 Hz); 4.26–4.34 (1H, m); 5.22,5.40 (2H, ABq, J=13.7 Hz); 5.71 (1H, d, J=1.4 Hz); 7.21,8.04 (4H, AA'BB', J=8.8 Hz); 7.00–7.43 (4H, m); 7.50,8.18 (4H, AA'BB', J=8.8 Hz).

EXAMPLE 55

4-Nitrobenzyl 5(R),3-[4-(4-cyanophenylthio-(carbonyl))phenoxy]-6(S)-[1(R)-hydroxyethyl]-7-oxo-4-thia-1-azabicyclo[3.2.0]hept-2-ene-2-carboxylate 201 mg of the above compound were obtained by a procedure analogous to that described in Example 49, using 452 mg of the 4(S)-chloroazetidinone derivative defined in Example 47, and 46 mg of imidazole.

$\nu_{max}$ (CDCl$_3$) 2225, 1783 cm$^{-1}$.

δ (CDCl$_3$) 1.43 (3H, d, J=6.3 Hz); 3.69 (1H, dd, J=1.5 Hz and 6.3 Hz); 4.15–4.28 (1H, m); 5.22,5.40 (2H, ABq, J=13.7 Hz); 5.69 (1H, d, J=1.5 Hz); 7.21–7.69 (8H, m); 8.03–8.25 (4H, m).

EXAMPLE 56

4-Nitrobenzyl 5(R),6(S)-[1(R)-hydroxyethyl]-3-[4-((2-methylprop-2-yl)thio-(carbonyl))phenoxy]-7-oxo-4-thia-1-azabicyclo[3.2.0]-hept-2-ene-2-carboxylate 442 mg of the above compound were obtained by a procedure analogous to that described in Example 49, using 899 mg of the 4(S)-chloroazetidinone derivative defined in Example 48, and 135 mg of imidazole.

$\nu_{max}$ (CDCl$_3$) 1785 cm$^{-1}$.

δ (CDCl$_3$) 1.36 (3H, d, J=6.2 Hz); 1.58 (9H, s); 2.20 (1H, broad s); 3.80 (1H, dd, J=1.3 Hz and 6.6 Hz); 4.22–4.35 (1H, m); 5.21,5.38 (2H, ABq, J=13.8 Hz); 5.68 (1H, d, J=1.3 Hz); 7.15,7.92 (4H, AA'BB', J=8.8 Hz); 7.48,8.16 (4H, AA'BB', J=8.8 Hz).

EXAMPLE 57

4-Nitrobenzyl 5(R),6(S)-[1(R)-hydroxyethyl]-3-[4-(N-(2-methoxyethyl)carbamoyl)phenoxy]-7-oxo-4-thia-1-azabicyclo[3.2.0]hept-2-ene-2-carboxylate 170 μl of 2-methoxyethylamine was added dropwise over 10 minutes to a cool (0° C.) stirred solution of 500 mg of 4-nitrobenzyl 5(R),6(S)-[1(R)-hydroxyethyl]-7-oxo-3-[4-(phenylthio-(carbonyl))phenoxy]-4-thia-1-azabicyclo[3.2.0]hept-2-ene-2-carboxylate and 330 mg of silver trifluoromethanesulphonate in dry acetonitrile. The mixture was stirred at room temperature protected from light until reaction was complete. The filtered solution was evaporated in vacuo and the residue chromatographed on silica gel using hexane/ethyl acetate mixtures as eluant to give 258 mg of the title compound as a pale yellow solid.

$\nu_{max}$ (CHCl$_3$) 1780 cm$^{-1}$.

δ (d$_6$-DMSO) 1.16 (3H, t, J=6.2 Hz); 3.26 (3H, s) 3.34–3.56 (4H, m); 3.91 (1H, dd, J=1 Hz and 5.8 Hz); 3.96–4.15 (1H, m); 5.22,5.40 (2H, ABq, J=13.8 Hz); 5.78 (1H, d, J=1 Hz); 7.36,7.90 (4H, AA'BB', J=8.8 Hz); 7.58,8.18 (4H, AA'BB', J=8.6 Hz); 8.57 (1H, broad s)

EXAMPLE 58

Potassium 5(R),6(S)-[1(R)-hydroxyethyl]-3-[4-(N-(2-methoxyethyl)carbamoyl)phenoxy]-7-oxo-4-thia-1-azabicyclo[3.2.0]hept-2-ene-2-carboxylate A mixture of a solution of 240 mg of 4-nitrobenzyl 5(R),6(S)-[1(R)-hydroxyethyl]-7-oxo-3-[4-(N-(2-methoxyethyl)carbamoyl)phenoxy]-4-thia-1-azabicyclo[3.2.0]hept-2-ene-2-carboxylate in ethyl acetate, and 44.5 mg of potassium bicarbonate in water, and 10% palladium/charcoal was hydrogenated at about 345 kPa (50 p.s.i.), until reaction was complete. The mixture was filtered through Celite (Trade Mark) and lyophilised to afford 181 mg of the title compound as an off-white solid.

$\nu_{max}$ (KBr) 1780 cm$^{-1}$.

δ (D$_2$O) 1.31 (3H, d, J=6.4 Hz); 3.40 (3H, s); 3.55–3.72 (4H, m); 3.96 (1H, dd, J=1.3 Hz and 6.0 Hz); 4.20–4.31 (1H, m); 5.71 (1H, d, J=1.3 Hz); 7.31,7.80 (4H, AA'BB', J=8.9 Hz)

EXAMPLE 59

4-Nitrobenzyl 5(R),3-[4-(N-(2-acetylaminoethyl)carbamoyl)phenoxy]-6(S)-[1(R)-hydroxyethyl]-7-oxo-4-thia-1-azabicyclo[3.2.0]-hept-2-ene-2-carboxylate 62 mg of the above compound were obtained by a procedure analogous to that described in Example 57 using 100 mg of the 4-nitrobenzyl 5(R),3-[4-(4-fluorophenylthio-(carbonyl))phenoxy]-6(S)-[1(R)-hydroxyethyl]-7-oxo-4-thia-1-azabicyclo[3.2.0]hept-2-ene-2-carboxylate defined in Example 53, 66 mg of silver trifluoromethanesulphonate, and 35 mg of 2-(acetylamino)ethylamine. The product was eluted from the silica gel column with ethyl acetate/hexane/methanol mixtures.

δ (d$_6$-acetone) 1.30 (3H, d, J=6.3 Hz); 1.89 (3H, s); 3.35–3.50 (4H, m); 3.91 (1H, dd, J=1.4 Hz and 6.2 Hz); 4.16–4.27 (1H, m); 5.28,5.45 (2H, ABq, J=14.1 Hz); 5.85 (1H, d, J=1.4 Hz); 7.47 (1H, broad s); 7.35,7.94 (4H, AA'BB', J=8.8 Hz); 7.66,8.19 (4H, AA'BB', J=8.8 Hz); 8.11 (1H, broad s).

EXAMPLE 60

Potassium 5(R),3-[4-(N-(2-acetylaminoethyl)carbamoyl)phenoxy]-6(S)-[1(R)-hydroxyethyl]-7-oxo-4-thia-1-azabicyclo[3.2.0]hept-2-ene-2-carboxylate 17 mg of the above compound were obtained from 59 mg of the corresponding 4-nitrobenzyl carboxylate defined in Example 59, by a procedure analogous to that described in Example 58, using 10.4 mg of potassium bicarbonate.

δ (D$_2$O) 1.27 (3H, d, J=6.4 Hz); 1.94 (3H, s); 3.30–3.54 (4H, m); 3.90 (1H, dd, J=1 Hz and 6.0 Hz); 4.14–4.28 (1H, m); 5.66 (1H, d, J=1 Hz); 7.26,7.73 (4H, AA'BB', J=8.6 Hz)

EXAMPLE 61

4-Nitrobenzyl 5(R),3-[4-(N-(carbamoylmethyl)carbamoyl)phenoxy]-6(S)-[1(R)-hydroxyethyl]-7-oxo-4-thia-1-azabicyclo[3.2.0]hept-2-ene-2-carboxylate 58 μl of triethylamine was added to a stirred solution of 121 mg of 4-nitrobenzyl 5(R),3-[4-(4-fluorophenylthio-(carbonyl))phenoxy]-6(S)-[1(R)-hydroxyethyl]-7-oxo-4-thia-1-azabicyclo[3.2.0]hept-2-ene-2-carboxylate and 80 mg of silver trifluoromethanesulphonate and 46 mg of glycinamide hydrochloride in DMF. The mixture was stirred in the dark until reaction was complete, ethyl acetate added and the organic solution washed successively with water and brine and dried over magnesium sulphate. The filtered solution was evaporated to dryness and the residue chromatographed on deactivated silica gel using hexane/ethyl acetate/methanol mixtures as eluant to afford 56 mg of the title compound as a pale yellow solid.

ν$_{max}$ (KBr disc) 1782 cm$^{-1}$.

δ (d$_6$-acetone) 1.29 (3H, d, J=6.3 Hz); 3.90 (1H, dd, J=1.5 Hz and 6.2 Hz); 3.97–4.15 (2H, m); 4.13–4.25 (1H, m); 5.27,5.44 (2H, ABq, J=13.3 Hz); 5.84 (1H, d, J=1.5 Hz); 7.35,7.99 (4H, AA'BB', J=8.9 Hz); 7.66,8.19 (4H, AA'BB', J=8.9 Hz); 7.95 (2H, broad s); 8.27 (1H, broad s).

EXAMPLE 62

Potassium 5(R),3-[4-(N-carbamoylmethyl))carbamoyl)phenoxy]-6(S)-[1(R)-hydroxyethyl]-7-oxo-4-thia-1-azabicyclo[3.2.0]hept-2-ene-2-carboxylate 19 mg of the above compound were obtained from 66 mg of the corresponding 4-nitrobenzyl carboxylate defined in Example 61, by a procedure analogous to that described in Example 58, using 12.5 mg of potassium bicarbonate.

δ (D$_2$O) 1.28 (3H, d, J=6.4 Hz); 3.93 (1H, dd, J=1.0 Hz and 5.9 Hz); 4.02–4.15 (2H, m); 4.17–4.34 (1H, m); 5.68 (1H, d, J=1.0 Hz); 7.29,7.84 (4H, AA'BB', J=8.8 Hz)

EXAMPLE 63

4-Nitrobenzyl 5(R),3-[4-(N-benzylcarbamoyl)phenoxy]-6(S)-[1(R)-hydroxyethyl]-7-oxo-4-thia-1-azabicyclo[3.2.0]hept-2-ene-2-carboxylate 46.6 mg of the above compound were obtained by a procedure analogous to that described in Example 57 using 400 mg of the 4-nitrobenzyl 5(R),6(S)-[1(R)-hydroxyethyl]-7-oxo-3-[4-(phenylthio-(carbonyl))phenoxy]-4-thia-1-azabicyclo[3.2.0]hept-2-ene-2-carboxylate defined in Example 53, 266 mg of silver trifluoromethanesulphonate, and 0.166 ml of benzylamine.

δ (CDCl$_3$-d$_6$-acetone) 1.37 (3H, d, J=6.3 Hz); 3.77 (1H, dd, J=1.2 Hz and 7.0 Hz); 4.18–4.28 (1H, m); 4.65 (2H, apparent d, J=5.7 Hz); 5.22,5.42 (2H, ABq, J=13.8 Hz); 5.68 (1H, d, J=1.2 Hz); 6.57 (1H, t, J=5.7 Hz); 7.19,7.83 (4H, AA'BB', J=8.7 Hz); 7.53,8.17 (4H, AA'BB', J=8.6 Hz); 7.20–7.45 (5H, m).

EXAMPLE 64

Potassium 5(R),3-[4-(N-benzylcarbamoyl)phenoxy]-6(S)-[1(R)-hydroxyethyl]-7-oxo-4-thia-1-azabicyclo[3.2.0]hept-2-ene-2-carboxylate 27 mg of the above compound were obtained from 34.7 mg of the corresponding 4-nitrobenzyl carboxylate defined in Example 63, by a procedure analogous to that described in Example 58, using 6 mg of potassium bicarbonate.

δ (D$_2$O) 1.30 (3H, d, J=6.3 Hz); 3.96 (1H, dd, J=1.1 Hz and 5.9 Hz); 4.11–4.28 (1H, m); 4.81 (2H, s); 5.72 (1H, d, J=1.1 Hz); 7.32,7.83 (4H, AA'BB', J=8.8 Hz); 7.35–7.73 (5H, m).

EXAMPLE 65

4-Nitrobenzyl 5(R),6(S)-[1(R)-hydroxyethyl]-7-oxo-3-[4-((N-(3-pyridyl)methyl)carbamoyl)phenoxy]-4-thia-1-azabicyclo[3.2.0]hept-2-ene-2-carboxylate 117 mg of the above compound were obtained by a procedure analogous to that described in Example 61 using 200 mg of the 4-nitrobenzyl 5(R),6(S)-[1(R)-hydroxyethyl]-7-oxo-3-[4-(4-chlorophenylthio-(carbonyl))phenoxy]-4-thia-1-azabicyclo[3.2.0]hept-2-ene-2-carboxylate defined in Example 52, 125 mg of silver trifluoromethanesulphonate, and 67 μl of 3-(aminomethyl)pyridine.

ν$_{max}$ (KBr disc) 1784 cm$^{-1}$.

δ (d$_6$-DMSO) 1.17 (3H, d, J=6.5 Hz); 3.9 (1H, dd, J=1.4 Hz and 5.8 Hz); 3.96–4.12 (1H, m); 4.50 (2H, broad d, J=5.8 Hz); 5.28,5.40 (2H. ABq, J=14.1 Hz); 5.79 (1H, d, J=1.4 Hz); 7.30–7.42 (1H, m); 7.39,7.95 (4H, AA'BB', J=8.8 Hz); 7.58,8.18 (4H, AA'BB', J=8.8 Hz); 7.73 (1H, broad d, J=7.9 Hz); 8.35–8.47 (1H, m); 8.48–8.59 (1H, m); 9.17 (1H, t, J=5.8 Hz).

EXAMPLE 66

Potassium 5(R),6(S)-[1(R)-hydroxyethyl]-7-oxo-3-[4-(N-((3-pyridyl)metyl)carbamoyl)phenoxy]-4-thia-1-azabicyclo[3.2.0]hept-2-ene-2-carboxylate 51 mg of the above compound were obtained from 115 mg of the corresponding 4-nitrobenzyl carboxylate defined in Example 65, by a procedure analogous to that described in Example 58, using 20 mg of potassium bicarbonate.

$\nu_{max}$ (KBr disc) 1778 cm$^{-1}$.

δ (D$_2$O) 1.29 (3H, d, J=6.4 Hz); 3.93 (1H, dd, J=1.1 Hz and 5.8 Hz); 4.18–4.27 (1H, m); 4.60 (2H, broad s); 5.69 (1H, d, J=1.1 Hz); 7.29,7.81 (4H, AA'BB', J=8.7 Hz); 7.38–7.48 (1H, m); 7.76–7.87 (1H, m); 8.36–8.55 (2H, m).

EXAMPLE 67

4-Nitrobenzyl 5(R),6(S)-[1(R)-hydroxyethyl]3-[4-(N-(2-(imidazol-4(5)-yl)ethyl)carbamoyl)phenoxy]-7-oxo-4-thia-1-azabicyclo[3.2.0]hept-2-ene-2-carboxylate 125 μl of triethylamine were added to a stirred solution of 4-nitrobenzyl 5(R),6(S)-[1(R)-hydroxyethyl]-3-[4-(4-chlorophenylthio-(carbonyl))phenoxy]-7-oxo-4-thia-1-azabicyclo[3.2.0]hept-2-ene-2-carboxylate, 86 mg of silver trifluoromethanesulphonate and 82 mg of histamine. dihydrochloride in dry dimethylformamide. Stirring was continued in the absence of light until t.l.c. indicated that reaction was complete, when water and ethyl acetate were added. The separated organic layer was washed with water and brine and dried over magnesium sulphate. Evaporation of the filtered solution followed by chromatography of the residue on deactivated silica gel using hexane/ethyl acetate/methanol mixtures as eluant gave the desired compound as a buff solid (117 mg).

$\nu_{max}$ (KBr disc) 1780 cm$^{-1}$.

δ (d$_6$-DMSO) 1.17 (3H, d, J=7.3 Hz); 3.00–3.19 (2H, m); 3.45–3.65 (2H, m); 3.91 (1H, dd, J=1.2 Hz and 6.0 Hz); 3.97–4.08 (1H, m); 5.28,5.40 (2H, ABq, J=14.0 Hz); 5.78 (1H, d, J=1.2 Hz); 7.24–7.75 (9H, m); 7.80–8.19 (2H, m); 8.65 (1H, broad t, J=4 Hz).

EXAMPLE 68

Potassium 5(R),6(S)-[1(R)-hydroxyethyl]-3-[4-(N-(2-imidazol-4(5)-yl)ethyl)carbamoyl)phenoxy]-7-oxo-4-thia-1-azabicyclo[3.2.0]hept-2-ene-2-carboxylate 57 mg of the above compound were obtained from 117 mg of the corresponding 4-nitrobenzyl carboxylate defined in Example 67, by a procedure analogous to that described in Example 58, using 20.2 mg of potassium bicarbonate.

$\nu_{max}$ (KBr disc) 1768 cm$^{-1}$.

δ (D$_2$O) 1.30 (3H, d, J=6.4 Hz); 2.85–3.00 (2H, m); 3.57–3.70 (2H, m); 3.95 (1H, dd, J=1.2 Hz and 6.0 Hz); 4.20–4.30 (1H, m); 5.71 (1H, d, J=1.2 Hz); 7.01 (1H, s); 7.27,7.69 (4H, AA'BB', J=8.8 Hz); 7.89 (1H, m).

EXAMPLE 69

4-Nitrobenzyl 5(R),6(S)-[1(R)-hydroxyethyl]-3-[4-(N-(methoxycarbonylmethyl)carbamoyl)phenoxy]-7-oxo-4-thia-1-azabicyclo[3.2.0]hept-2-ene-2-carboxylate 60 mg of the above compound were obtained by a procedure analogous to that described in Example 67 using 152 mg of 4-nitrobenzyl 5(R),6(S)-[1(R)-hydroxyethyl]-3-[4-(4-chlorophenylthio-(carbonyl))phenoxy]-7-oxo-4-thia-1-azabicyclo[3.2.0]hept-2-ene-2-carboxylate defined in Example 53, 95.6 mg of silver trifluoromethanesulphonate, and 62.3 mg of glycine methyl ester hydrochloride and 69 μl of triethylamine.

$\nu_{max}$ (CDCl$_3$) 1787 cm$^{-1}$.

δ (d$_6$-acetone) 1.29 (3H, d, J=6.3 Hz); 3.69 (3H, s); 3.91 (1H, dd, J=1.5 Hz and 6.2 Hz); 4.12 (2H, d, J=5.9 Hz); 4.10–4.25 (1H, m); 5.27,5.43 (2H, ABq, J=14.1 Hz); 5.85 (1H, d, J=1.5 Hz); 7.36,7.98 (4H, AA'BB', J=8.8 Hz); 7.65,8.18 (4H, AA'BB', J=8.9 Hz); 8.13 (1H, broad s).

EXAMPLE 70

Potassium 5(R),6(S)-[1(R)-hydroxyethyl]-3-[4-(N-(methoxycarbonylmethyl)carbamoyl)phenoxy]-7-oxo-4-thia-1-azabicyclo[3.2.0]hept-2-ene-2-carboxylate 35 mg of the above compound were obtained from 60 mg of the corresponding 4-nitrobenzyl carboxylate defined in Example 69, by a procedure analogous to that described in Example 58, using 10.8 mg of potassium bicarbonate.

$\nu_{max}$ (KBr) 1775 cm$^{-1}$.

δ (D$_2$O) 1.31 (3H, d, J=6.4 Hz); 3.79 (3H, s); 3.96 (1H, dd, J=1.2 Hz and 6.0 Hz); 4.19 (2H, s); 4.15–4.34 (1H, m); 5.72 (1H, d, J=1.2 Hz); 7.32,7.85 (4H, AA'BB', J=8.8 Hz).

EXAMPLE 71

4-Nitrobenzyl 5(R),6(S)-[1(R)-hydroxyethyl]-3-[4-(N-(4-nitrobenzyloxycarbonylmethyl)carbamoyl)phenoxy]-7-oxo-4-thia-1-azabicyclo[3.2.0]hept-2-ene-2-carboxylate

Method A 40 mg of the above compound were obtained by a procedure analogous to that described in Example 61 using 100 mg of 4-nitrobenzyl 5(R),6(S)-[1(R)-hydroxyethyl]-3-[4-(4-methoxyphenylthio-(carbonyl))phenoxy]-7-oxo-4-thia-1-azabicyclo-[3.2.0]hept-2-ene-2-carboxylate, 63 mg of silver trifluoromethanesulphonate, 106 mg of glycine 4-nitrobenzyl ester trifluoroacetate salt and 46 μl of triethylamine.

Method B 107 mg of the title compound were obtained by a procedure analogous to that described in Example 61 using 260 mg of 4-nitrobenzyl 5(R),6(S)-[1(R)-hydroxyethyl]-7-oxo-3-[4-(phenylthio-(carbonyl))phenoxy]-4-thia-1-azabicyclo[3.2.0]hept-2-ene-2-carboxylate, 173 mg of silver trifluoromethanesulphonate, 219 mg of glycine 4-nitrobenzyl ester trifluoroacetate salt and 125 μl of triethylamine.

Method C 99 mg of glycine 4-nitrobenzyl ester trifluoroacetate salt was added to a stirred solution of 102 mg of 4-nitrobenzyl 5(R),6(S)-[1(R)-hydroxyethyl]-7-oxo-3-[4-(pentafluorophenylthio-(carbonyl))phenoxy]-4-thia-1-azabicyclo[3.2.0]hept-2-ene-2-carboxylate and 59 mg of silver trifluoromethanesulphonate and 43 μl of triethylamine in dry acetonitrile. The mixture was stirred at room temperature protected from light until the reaction was complete. The solution was filtered, diluted with ethyl acetate, and the organic solution washed with water and dried over magnesium sulphate. The filtered solution was evaporated in vacuo and the residue chromatographed on silica gel using hexane/ethyl acetate mixtures to afford 8.8 mg of the title compound.

Method D 69 mg of glycine 4-nitrobenzyl ester trifluoroacetate salt were added to a stirred solution of 116 mg of 4-nitrobenzyl 5(R),6(S)-[1(R)-hydroxyethyl]-7-oxo-3-[4-(pentafluorophenylthio-(carbonyl))phenoxy]-4-thia-1-azabicyclo[3.2.0]hept-2-ene-2-carboxylate and 30 μl of triethylamine in dry acetonitrile. The mixture was stirred at room temperature until the reaction was complete, whereupon solvent was evaporated and the residue obtained chromatographed on silica gel using hexane/ethyl acetate mixtures to give 75 mg of the title compound.

$\delta$ ($d_6$-acetone) 1.31 (3H, d, J=6.3 Hz); 3.92 (1H, dd, J=1.3 Hz and 6.2 Hz); 4.10–4.25 (1H, m); 4.27 (2H, d, J=6.0 Hz); 5.21–5.50 (4H, m); 5.86 (1H, d, J=1.3 Hz); 7.37,8.01 (4H, AA'BB', J=8.8 Hz); 7.65,8.21 (4H, AA'BB', J=8.8 Hz); 7.71,8.25 (4H, AA',BB', J=8.6 Hz).

EXAMPLE 72

Potassium 5(R),3-[4-(N-(carboxymethyl)carbamoyl)phenoxy]-6(S)-[1(R)-hydroxyethyl]-7-oxo-4-thia-1-azabicyclo[3.2.0]hept-2-ene-2-carboxylate 40 mg of the above compound were obtained from 105 mg of the corresponding 4-nitrobenzyl carboxylate defined in Example 71, by a procedure analogous to that described in Example 58, using 15.5 mg of potassium bicarbonate.

$\delta$ ($D_2O$) 1.28 (3H, d, J=6.4 Hz); 3.93 (2H, s); 3.89–3.99 (1H, m); 4.20–4.34 (1H, m); 5.70 (1H, d, J=1.0 Hz); 7.31,7.84 (4H, AA'BB', J=8.8 Hz).

EXAMPLE 73

Pentafluorophenyl 4-acetoxybenzoate

A solution of 10.8 g of 4-acetoxybenzoyl chloride in dry acetonitrile was treated with 10 g of pentafluorophenol, and stirred at 0° C. whilst 4.4 ml of pyridine was added dropwise. The solution was permitted to warm to room temperature then heated to reflux temperature until the reaction was complete. Solvent was evaporated in vacuo and the residue obtained partitioned between ethyl acetate and water. The organic solution was washed with further portions of water and brine and dried over magnesium sulphate. Evaporation afforded 18 g of the title compound.

$\nu_{max}$ (film) 1760 cm$^{-1}$.

$\delta$ (CDCl$_3$) 2.25 (3H, s); 7.21,8.21 (4H, AA'BB', J=9 Hz).

EXAMPLE 74

Pentafluorophenyl 4-hydroxybenzoate

The title compound (8 g) was prepared from 10 g of pentafluorophenyl 4-acetoxybenzoate in an analogous manner to that described in Example 9.

$\nu_{max}$ (film) 1760 cm$^{-1}$.

$\delta$ (CDCl$_3$) 6.86,7.01 (4H, AA'BB', J=9 Hz); 7.30 (1H, broad s).

EXAMPLE 75

Pentafluorophenyl 4-chlorothiocarbonyloxybenzoate

A solution of 1.34 g of sodium hydroxide in water was added dropwise over 15 minutes with vigorous stirring to a solution of 8.5 g of pentafluorophenyl 4-hydroxybenzoate and 3.2 ml of thiophosgene in 100 ml of chloroform at −20° C. The mixture was stirred at 5° C. until the reaction was complete and the organic layer separated, dried over calcium chloride and the solvent evaporated. Chromatography of the residue on silica gel eluting with hexane/ethyl acetate mixtures afforded 5.9 g of the title compound.

$\nu_{max}$ (film) 1760 cm$^{-1}$.

$\delta$ (CDCl$_3$) 7.32,8.30 (4H, AA'BB', J=8 Hz).

EXAMPLE 76

4-Nitrobenzyl-2-[3(S)-1(R)-dimethyl-(2-methylprop-2-yl)silyloxyethyl)-4(R)-ethylthioazetidin-2-on-1-yl]-3-[4-(pentafluorophenoxycarbonyl)phenoxy]-3-trimethylacetylthiopropenoate 10.9 g of the title compound were obtained by a procedure analogous to that described in Example 25 using 6.76 g of 4-nitrobenzyl-2-[3(S)-1(R)-dimethyl-(2-methylprop-2-yl)silyloxyethyl)-4(R)-ethylthioazetidin-2-on-1-yl]acetate, 6.65 ml of hexamethyldisilazane, 5.89 g of pentafluorophenyl 4-chlorothiocarbonyloxybenzoate, 31.5 mmol of n-butyllithium and 3.72 ml of pivaloyl bromide.

$\delta$ (CDCl$_3$) 0.02 (6H, s); 0.81,0.89 (9H, 2s); 1.09,1.16 (9H, 2s); 1.16–1.32 (6H, m); 2.51–2.79 (2H, m); 3.24–3.32 (1H, m); 4.22–4.29 (1H, m); 5.25–5.47 (3H, m); 6.95–8.24 (8H, m).

EXAMPLE 77

4-Nitrobenzyl-2-[4(R)-ethylthio-3(S)-[1(R)-hydroxyethyl]-azetidin-2-on-1-yl]-3-[4-(pentafluorophenoxycarbonyl)phenoxy]-3-trimethylacetylthiopropenoate 3.7 g of the title compound were obtained from 10.9 g of the corresponding [1(R)-dimethyl-(2-methylprop-2-yl)silyloxyethyl] compound described in Example 76 by a process analogous to that described in Example 33 using 43 ml of 5M hydrochloric acid.

$\nu_{max}$ (film) 1760 cm$^{-1}$.

$\delta$ (CDCl$_3$) 1.09 (9H, s); 1.16–1.34 (6H, m); 1.75 (1H, broad s); 2.69–2.76 (2H, m); 3.26 (1H, dd, J=2.5 Hz and 4.8 Hz); 4.2–4.3 (1H, m); 5.26 (1H, d, J=2.5 Hz); 5.26,5.34 (2H, ABq, J=9 Hz); 7.18,8.17 (4H, AA'BB', J=8.8 Hz); 7.60,8.24 (4H, AA'BB', J=8.8 Hz).

Signals due to the minor propenoate isomer were also detectable.

EXAMPLE 78

4-Nitrobenzyl-2-[4(S)-chloro-3(S)-[1(R)-hydroxyethyl]azetidin-2-on-1-yl]-3-[4-(pentafluorophenoxycarbonyl)phenoxy]-3-trimethylacetylthiopropenoate 2.5 g of the title compound were obtained by a procedure analogous to that described in Example 41, using 3.73 g of the corresponding 1(R)-hydroxyethylazetidin-2-one described in Example 77 and a solution of 5.6 mmol of chlorine in carbon tetrachloride.

$\delta$ (CDCl$_3$) 1.10 (9H, s); 1.39 (3H, d, J=6.3 Hz); 1.61 (1H, broad s); 3.54 (1H, dd, J=4.3 Hz and 9.4 Hz); 4.29–4.35 (1H, m); 5.33 (2H, s); 6.13 (1H, d, J=4.3 Hz); 7.17,8.19 (4H, AA'BB', J=8.8 Hz); 7.56,8.25 (4H, AA'BB', J=8.8 Hz).

EXAMPLE 79

4-Nitrobenzyl 5(R),6(S)-[1(R)-hydroxyethyl]-7-oxo-3-[4-(pentafluorophenoxycarbonyl)phenoxy]-4-thia-1-azabicyclo[3.2.0.]hept-2-ene-2-carboxylate 2.56 g of the title compound were obtained by a procedure analogous to that described in Example 49 using 3.73 g of the 4(S)-chloroazetidinone defined in Example 78 and 243 mg of imidazole.

$\nu_{max}$ (KBr) 1770 cm$^{-1}$.

$\delta$ (CDCl$_3$) 1.39 (3H, d, J=6.3 Hz); 1.75 (1H, broad s); 3.85 (1H, dd, J=1.4 Hz and 6.5 Hz); 4.28–4.33 (1H, m); 5.21,5.40 (2H, ABq, J=14.7 Hz); 5.74 (1H, d, J=1.4 Hz); 7.27,8.18 84H, AA'BB', J=8.9 Hz); 7.62,8.22 (4H, AA'BB', J=8.7 Hz).

EXAMPLE 80

Diphenyl-(2-methylprop-2-yl)silyl 3-hydroxybenzoate

To stirred solution of 50.4 g of 3-hydroxybenzoic acid in 200 ml of dry dimethylformamide at 0° C. was added 24.85 g of imidazole, followed by 100 g of diphenyl-(2-methylprop-2-yl)silyl chloride. The mixture was stirred at room temperature for 16 hours, and partitioned between ethyl acetate and cold water. The organic layer was washed with water, with an aqueous potassium hydrogen carbonate solution and with brine, was dried over anhydrous magnesium sulphate and evaporated to dryness. The resulting white solid was slurried in dry chloroform and filtered to afford 72 g of the title compound.

$\delta$ (acetone-d$_6$) 1.18 (9H, s); 6.8–7.9 (14H, m); 8.7 (1H, broad s).

EXAMPLE 81

Diphenyl-(2-methylprop-2-yl)silyl 3-chlorothioformyloxybenzoate

To a stirred solution of 130 ml of thiophosgene in 250 ml of dry diethyl ether at −78° C. was added dropwise a mixture of 72 g of diphenyl- (2-methylprop-2-yl)silyl 3-hydroxybenzoate and 29 ml of triethylamine in 200 ml of dry diethyl ether. The mixture was stirred at −78° C. for 30 minutes, at room temperature for 120 minutes, and then partitioned between diethyl ether and water. The organic layer was washed with cold water and with brine, and was dried over anhydrous calcium chloride. Evaporation in vacuo, and repeated addition of dry diethyl ether and re-evaporation in vacuo afforded 86.5 g of the title compound as a viscous orange oil.

$\delta$ (CDCl$_3$) 1.20 (9H, s); 7.35–7.55 (7H, m); 7.54 (1H, t, J=7.8 Hz); 7.74 (4H, dm, J=6 Hz); 7.90 (1H, dd, J=2.2 and 1.6 Hz); 8.11 (1H, dm, J=7.8 Hz).

EXAMPLE 82

4-Nitrobenzyl 2-(3(S)-{1(R)[dimethyl(2-methylprop-2-yl)silyloxy]ethyl}-4(R)-ethylthioazetidin-2-on-1-yl)-3-(3-{diphenyl-[2-methylprop-2-yl]silyloxycarbonyl}phenoxy)-3-trimethylacetylthiopropenoate By a procedure analogous to that described in Example 90, and using 15 g of 4-nitrobenzyl 2-(3(S)-1(R)[dimethyl(2-methylprop-2-yl)silyloxy]ethyl -4(R)-ethylthioazetidin-2-on-1-yl)acetate, 17 g of diphenyl(2-methylprop-2-yl)silyl 3-chlorothioformyloxybenzoate, 70 mmol of n-butyllithium, 14.7 ml of hexamethyldisilazane, 750 ml of dry tetrahydrofuran, and 11.4 ml of trimethylacetyl bromide there was obtained 40 g of the title compound as an orange oil, which was used without further purification.

$\nu_{max}$ (film) 1710 and 1765 cm$^{-1}$.

$\delta$ (CDCl$_3$) 0.05 (6H, s); 0.83 (9H, s); 0.91 (9H, 2s); 1.04 and 1.11 (9H, 2s); 1.2–1.4 (6H, m); 2.5–2.9 (2H, m); 3.3 (1H, m); 4.35 (1H, m); 5.36 (2H, m); 5.48 (1H, d, J=2 Hz); 7.3–8.4 (18H, m).

EXAMPLE 83

4-Nitrobenzyl 3-(3-carboxyphenoxy)-2-(4(R)-ethylthio-3(S)-[1(R)-hydroxyethyl]azetidin-2-on-1-yl)-3-trimethylacetylthiopropenoate A mixture of 40 g of 4-nitrobenzyl 2-(3(S) -1(R)-[dimethyl-(2-methylprop-2-yl)silyloxy]ethyl -4(R)-ethylthioazetidin-2-on-1-yl)-3-(3-diphenyl[2-methylprop-2-yl]silyloxycarbonyl phenoxy)-3-trimethylacetylthiopropenoate, 150 ml of tetrahydrofuran, and 44 ml of 5.5M-hydrochloric acid was stirred at room temperature for 16 hours, and was then partitioned between ethyl acetate and water. The organic layer was washed with water and with brine, was dried over anhydrous magnesium sulphate, and was evaporated in vacuo. Chromatography of the residue over silica gel, and elution with hexane-ethyl acetate-formic acid mixtures afforded 6.0 g of the title product as an E/Z mixture.

$\nu_{max}$ 1735, 1715(sh), 1770(sh), 3450 cm$^{-1}$.

$\delta$ (CDCl$_3$) 1.00 and 1.07 (9H, 2s); 1.2–1.4 (6H, m); 2.6–2.9 (2H, m); 3.28 (1H, dd, J=2.7 and 4.4 Hz); 4.3 (1H, m); 5.32 (2H, AB, J=13.5 Hz); 5.37 (1H, d, J=2.7 Hz); 7.29 (1H, m); 7.37 (1H, dd, J=2 and 7.8 Hz); 7.59 and 7.40 (2H, AA'BB', J=7.8 Hz); 7.71 (1H, m); 7.86 (1H, dm, J=7.8 Hz); 8.08 and 8.22 (2H AA'BB', J=7.8 Hz).

EXAMPLE 84

4-Nitrobenzyl 3-(3-carboxyphenoxy)-2-(4(S)-chloro-3(S)-(1(R)-hydroxyethyl)azetidin-2-on-1-yl)-3-trimethylacetylthiopropenoate To a stirred solution of 5.5 g of 4-nitrobenzyl 3-(3-carboxyphenoxy)-2-(4(R)-ethylthio-3(S)-[1(R)-hydroxyethyl]azetidin-2-on-1-yl)-3-trimethylacetylthiopropenoate in 50 ml of dry deuterochloroform at −40° C. was added a solution of 10.6 mmol of chlorine in carbon tetrachloride. The mixture was stirred for a further 30 minutes at −40° C., and for 30 minutes at room temperature, and was evaporated in vacuo. Chromatography of the residue over silica gel, and elution with hexane-ethyl acetate-formic acid mixtures afforded 4.6 g of the title compound.

$\nu_{max}$ (CDCl$_3$) 1700, 1730, 1783 cm$^{-1}$.

δ (CDCl$_3$) 1.03 and 1.07 (9H, 2s); 1.40 (3H, d, J=6.4 Hz); 3.55 (1H, m); 4.4 (1H, m); 5.32 (1H, s); 6.15 and 6.20 (1H, 2d, J=4.2 Hz); 7.29 (1H, m); 7.4–7.7 (3H, m); 7.74 (1H, m); 7.9–8.05 (1H, m); 8.12 and 8.24 (2H, 2d, J=8.8 Hz).

EXAMPLE 85

4-Nitrobenzyl 5(R),3-(3-carboxyphenoxy)-6(S)-(1(R)-hydroxyethyl)-7-oxo-4-thia-1-azabicyclo[3,2,0]hept-2-ene-2-carboxylate To a stirred solution of 2.02 g of 4-nitrobenzyl 3-(3-carboxyphenoxy)-2-(4(S)-chloro-3(S)-(1(R)-hydroxyethyl)azetidin-2-on-1-yl)-3-trimethyl-acetylthiopropenoate in 80 ml of a mixture of dioxane and water (9:1 v/v) at 5° C. was added 682 mg of imidazole. The mixture was stirred for a further 30 minutes at 5°, and was then partitioned between ethyl acetate and water. The aqueous layer was acidified to pH2 by the addition of 1M-citric acid, and extracted with ethyl acetate. The combined organic layers were washed with 1M-citric acid, with water and with brine, were dried over anhydrous magnesium sulphate and evaporated in vacuo. The residue was chromatographed over silica gel; elution with hexane-ethyl acetate-formic acid mixtures afforded 992 mg of the title compound as a pale yellow foam.

$\nu_{max}$ (CDCl$_3$) 1710, 1788 cm$^{-1}$.

δ (CDCl$_3$) 1.38 (3H, d, J=6.4 Hz); 3.81 (1H, dd, J=1.4 and 6.7 Hz); 4.3 (1H, m); 5.24 and 5.43 (2H, AB, J=13.8 Hz); 5.69 (1H, d, J=1.4 Hz); 7.38–7.5 (2H, m); 7.55 and 8.18 (4H, AA'BB', J=8.8 Hz); 7.85 (1H, m); 7.99 (1H, m).

EXAMPLE 86

4-Nitrobenzyl 5(R),3-(3-carbamoylmethylcarbamoylphenoxy)-6(S)-(1(R)-hydroxyethyl)-7-oxo-4-thia-1-azabicyclo[3,2,0-]hept-2-ene-2-carboxylate To a stirred solution of 200 mg of 4-nitrobenzyl 5(R),3-(3-carboxyphenoxy)-6(S)-(1(R)-hydroxyethyl)-7-oxo-4-thia-1-azabicyclo[3,2,0]hept-2-ene-2-carboxylate in 10 ml of acetonitrile was added a solution of 246 mg of 1-hydroxybenzotriazole hydrate in 5 ml of tetrahydrofuran, followed after 5 minutes by 249 mg of 1-(3-dimethylaminopropyl)-3-ethylcarbodiimide hydrochloride. After 20 minutes, the mixture was cooled to 0° C., 177 μl of triethylamine was added, followed by a solution of 144 mg of glycinamide hydrochloride in 2 ml of water. The mixture was warmed to 20° C. over one hour, and then partitioned between ethyl acetate and water. The organic layer was washed with water, with 1M-citric acid, with water, with saturated aqueous sodium bicarbonate, and with brine, was dried over anhydrous magnesium sulphate and evaporated in vacuo to afford 161 mg of the title compound as a pale yellow solid.

(acetone -d$_6$)δ1.30 (3H, d, J=6.3 Hz); 3.89 (1H, dd, J=1.5 and 6.3 Hz); 4.04 (2H, d, J=5.7 Hz); 4.20 (1H, m); 4.5 (1H, broad s); 5.28 and 5.47 (2H, ABq, J=14.2 Hz); 5.83 (1H, d, J=1.5 Hz); 6.5 (1H, broad s); 7.1 (1H, broad s); 7.4–7.6 (2H, m); 7.69 and 8.20 (4H, AA'BB', J=8.8 Hz); 7.75–7.9 (2H, m); 8.15 (1H, broad)

EXAMPLE 87

Potassium 5(R),3-(3-carbamoylmethylcarbamoylphenoxy)-6(S)-(1(R)-hydroxyethyl)-7-oxo-4-thia-1-azabicyclo[3,2,0-]hept-2-ene-2-carboxylate A mixture of 100 mg of 4-nitrobenzyl 5(R),3-(3-carbamoylmethylcarbamoylphenoxy)-6(S)-(1(R)-hydroxyethyl)-7-oxo-4-thia-1-azabicyclo[3,2,0]hept-2-ene-2-carboxylate, 5 ml of dioxane, 18 mg of potassium bicarbonate, 50 mg of 10% palladium on charcoal and 5 ml of distilled water was hydrogenolysed at 3.5 bar for 30 minutes. The mixture was then filtered through Hyflo Supercel filter aid (BDH); the filter aid was washed with further portions of water and dioxane, and the combined filtrate lyophilised to afford 120 mg of a dark yellow solid. This solid was partitioned between water and ethyl acetate, and the aqueous layer was lyophilised to afford 80 mg of the title compound.

δ (D$_2$O) 1.25 (3H, d, J=6 Hz); 3.89 (1H, dd, J=1 and 6 Hz); 4.03 (2H, s); 4.18 (1H, m); 5.65 (1H, d, J=1 Hz); 7.0–7.8 (4H, m).

EXAMPLE 88

Diphenyl-(2-methylprop-2-yl)silyl 4-hydroxybenzoate

To a solution of 20 g of 4-hydroxybenzoic acid and 10 g of imidazole in 100 ml of dry dimethylformamide at 0° C. was added 40 g of t-butylchlorodiphenylsilane. The mixture was stirred at 0° C. for 30 minutes, then at 20° C. for 18 hours, and then partitioned between diethyl ether and water. The organic layer was washed with water, with 10% aqueous potassium hydrogen carbonate, with water and with brine, and then dried over magnesium sulphate. Evaporation in vacuo of the solvent afforded 47.5 g of the title compound as a crystalline white powder.

δ (CDCl$_3$) 1.18 (9H, s); 6.16 (1H, broad s); 6.68 and 7.95 (4H, AA'BB', J=8.8 Hz); 7.35–7.50 (6H, m); 7.70–7.90 (4H, m).

EXAMPLE 89

Diphenyl-(2-methylprop-2-yl)silyl 4-chlorothioformyloxybenzoate

To a solution of 40.7 ml of thiophosgene in 300 ml of dry diethyl ether at −78° C. was added dropwise a solution of 20 g of diphenyl-(2-methylprop-2-yl)silyl 4-hydroxybenzoate and 8.5 ml of triethylamine. After having been stirred for a further 30 minutes at −78° C. and 90 minutes at room temperature, the mixture was partitioned between diethyl ether and water. The organic layer was washed with water and brine, was dried over calcium chloride, and then evaporated in vacuo to afford 25.9 g of an orange oil. Chromatography over silica gel and elution with hexane-ethyl acetate mixtures afforded 16.8 g of the title compound.

δ (CDCl$_3$) 1.19 (9H, s); 7.26 and 8.24 (4H, AA'BB', J=8.8 Hz); 7.4–7.6 (6H, m); 7.7–7.9 (4H, m).

EXAMPLE 90

4-Nitrobenzyl 2-(3(S)-1(R)-[dimethyl(2-methylprop-2-yl)silyloxy]ethyl -4(R)-ethylthio-azetidin-2-on-1-yl)-3-(4-diphenyl-[2-methylprop-2-yl]silyloxycarbonyl phenoxy)-3-trimethylacetylthiopropenoate To a stirred solution at −40° C. of 25 g of 4-nitrobenzyl 2-(3(S)-[1(R)-dimethyl(2-methylprop-2-yl)silyloxyethyl]-4(R)-ethylthioazetidin-2-on-1-yl)acetate was added a solution of 35 g of diphenyl-(methylprop-2-yl)silyl 4-chlorothioformyloxybenzoate in 200 ml of dry tetrahydrofuran, followed by a mixture of 155 mmol of n-butyllithium and 155 mmol of hexamethyldisilazane in 200 ml of dry tetrahydrofuran which had been precooled to −78° C. After 5 minutes, 13.8 ml of trimethylacetyl bromide was added and the mixture stirred for a further 60 minutes at −40° C., and then poured directly into a mixture of 500 ml of diethyl ether and 500 ml of 0.1M hydrochloric acid. The aqueous layer was extracted in diethyl ether, and the combined organic extracts were washed with brine, dried over aqueous magnesium sulphate and evaporated in vacuo to afford 50 g of an orange oil. The product was used without further purification.

EXAMPLE 91

4-Nitrobenzyl 3-(4-carboxyphenoxy)-2-(4(R)-ethylthio-3(S)-[1(R)-hydroxyethyl]azetidin-2-on-1-yl)-3-trimethylacetylthiopropenoate A mixture of 50 g of 4-nitrobenzyl 2-(3(S)-[1(R)-[dimethyl-(2-methylprop-2-yl)silyl]oxyethyl]-4(R)-ethylthioazetidin-2-on-1-yl)-3-(4-{diphenyl[2-methylprop-2-yl]silyloxycarbonyl}phenoxy)-3-trimethylacetylthiopropenoate, 500 ml of tetrahydrofuran and 100 ml of 5.5M hydrochloric acid was stirred at room temperature for 24 hours, and then partitioned between diethyl ether and water. The organic layer was washed with water, and with brine, was dried over anhydrous magnesium sulphate, and evaporated in vacuo. Chromatography of the residue over silica gel, and elution with hexane-ethyl acetate-formic acid mixtures afforded 10.2 g of the title compound.

$v_{max}$ (CDCl$_3$) 1765 cm$^{-1}$.

δ (CDCl$_3$) 1.05 and 1.13 (9H, 2s); 1.20–1.30 (6H, m) 2.6–2.8 (2H, m); 3.27 (1H, dd, J=2.5 and 4.5 Hz); 4.2–4.4 (1H, m); 5.30 (1H, d, J=2.5 Hz); 5.31 (2H, AB, J=13.5 Hz); 7.10 and 8.03 (4H, AA'BB', J=9 Hz); 7.60 and 8.24 (4H, AA'BB', J=9 Hz).

EXAMPLE 92

4-Nitrobenzyl 3-(4-carboxyphenoxy)-2-(4(S)-chloro-3(S)-[1(R)-hydroxyethyl]azetidin-2-on-1-yl)-3-trimethylacetylthiopropenoate To a stirred solution of 10 g of 4-nitrobenzyl 3-(4-carboxyphenoxy)-2-(4(R)-ethylthio-3(S)- [1(R)-hydroxyethyl]azetidin-2-on-1-yl)-3-trimethylacetylthiopropenoate in 60 ml of chloroform at −60° C. was added a solution of 192 mmoles of chlorine in 17.8 ml of carbon tetrachloride. After 30 minutes, the reaction mixture was left to warm to room temperature, and the solvent was then removed in vacuo. Chromatography over silica gel using hexane-ethyl acetate-formic acid mixtures afforded 7.3 g of the title compound as a pale yellow foam.

$v_{max}$ (CDCl$_3$) 1787, 1731 cm$^{-1}$.

δ (CDCl$_3$) 1.06 and 1.10 (9H, 2s); 1.39 (3H, d, J=6.2 Hz); 3.53 (1H, dd, J=4.3 and 9.5 Hz); 4.33 (1H, dq, J=6.2 and 9.5 Hz); 5.30 (2H, s); 6.14 (1H, d, J=4.3 Hz); 7.10 and 8.09 (4H, AA'BB', J=8.8 Hz); 7.56 and 8.25 (4H, AA'BB', J=8.7 Hz).

EXAMPLE 93

4-Nitrobenzyl 5(R),3-(4-carboxyphenoxy)-6(S)-(1(R)-hydroxyethyl)-7-oxo-4-thia-1-azabicyclo[3,2,0]hept-2-ene-2-carboxylate To a stirred solution of 5.3 g of 4-nitrobenzyl 3-(4-carboxyphenoxy)-2-(4(S)-chloro-3(S)-[1(R)-hydroxyethyl]azetidin-2-on-1-yl)-3-trimethylacetylthiopropenoate in a mixture of 90 ml of dioxane and 10 ml of water at 5° C. was added 1.78 g of imidazole. After 30 minutes at 5° C., the mixture was warmed to room temperature, and then partitioned between ethyl acetate and water. The organic layer was washed successively with water, 1M-citric acid, water, and brine, was dried over magnesium sulphate, and the solvent removed in vacuo. Chromatography over silica gel using ethyl acetate-hexane-formic acid mixtures afforded 3.2 g of the title compound as a pale yellow solid. Further purification by crystallisation from ethyl acetate yielded 1.8 g of a white solid.

$v_{max}$ (CDCl$_3$) 1788, 1794(sh) cm$^{-1}$.

δ (CDCl$_3$) 1.39 (3H, d, J=6.3 Hz); 3.83 (1H, dd, J=1.4 and 6.7 Hz); 4.30 (1H, m); 5.21 and 5.40 (2H, AB, J=13.7 Hz); 5.71 (1H, d, J=1.4 Hz); 7.20 and 8.11 (4H, AA'BB', J=8.9 Hz); 7.51 and 8.18 (4H, AA'BB', J=8.8 Hz).

EXAMPLE 94

1,2-Di(4-nitrobenzyloxycarbonylamino)ethane

To a vigorously shaken solution of 1.39 g of ethylene diamine in 20 ml of water and 20 ml of tetrahydrofuran was added over 45 minutes a solution of 5 g of 4-nitrobenzyl chloroformate in 20 ml of dioxane. The mixture was allowed to warm to room temperature, and 150 ml of ethyl acetate and 200 ml of water were added. The mixture was filtered, and the filtrate dried to afford 2.67 g of the title compound.

δ (DMSO-d$_6$) 3.08 (4H, broad s); 5.16 (4H, s) 7.49 (2H, broad s); 7.59 and 8.21 (4H, AA'BB', J=8.7 Hz).

EXAMPLE 95

4-Nitrobenzyl 2-aminoethylcarbamate hydrochloride

A mixture of 355 mg of 1,2-di(4-nitrobenzyloxycarbonylamino)ethane, 4 ml of acetic acid and 0.5 ml of 11M-hydrochloric acid was heated under reflux for 2.5 hours, and then lyophilised in vacuo. The solid residue was partitioned between ethyl acetate and water, and the insoluble material removed by filtration. The aqueous layer was separated and washed with ethyl acetate and then lyophilised to afford 139 mg of an off-white solid. Recrystallisation from ethanol afforded 100 mg of the title compound, m.p. 170°–171° C. dec.

δ (D$_2$O) 3.11 (2H, t, J=5.8 Hz); 3.43 (2H, t, J=5.8 Hz) 5.22 (2H, s); 7.57 and 8.22 (4H, AA'BB', J=8.5 Hz).

EXAMPLE 96

4-Nitrobenzyl 5(R),6(S)-(1(R)-hydroxyethyl)-3-(4-(4-nitrobenzyloxycarbonylaminoethyl)carbamoylphenoxy)-7-oxo-4-thia-1-azabicyclo[3,2,0]hept-2-ene-2-carboxylate To a well stirred slurry of 160 mg of 4-nitrobenzyl 5(R),3-(4-carboxyphenoxy)-6(S)-(1(R) -hydroxyethyl)-7-oxo-4-thia-1-azabicyclo[3,2,0]hept-2-ene-2-carboxylate in 12 ml of acetonitrile at 20° C. was added a solution of 89 mg of 1-hydroxybenzotriazole hydrate in 4 ml of tetrahydrofuran. After 5 minutes, 94 mg of 1-(3-dimethyl(aminopropyl)-3-ethylcarbodiimide hydrochloride was added. The mixture was stirred for a further 60 minutes at room temperature, and then cooled to 0° C.; 185 μl of triethylamine were added, followed by 100 mg of 4-nitrobenzyl 2-aminoethylcarbamate hydrochloride. The mixture was warmed over 60 minutes to 20° C. The solid product was filtered off and washed with 2 ml of acetonitrile to afford 113 mg of substantially pure title material. The combined filtrate was partitioned between ethyl acetate and water; the organic layer was washed successively with 1M-citric acid, saturated aqueous sodium bicarbonate, and brine, was dried over anhydrous magnesium sulphate and evaporated in vacuo to afford a further 121 mg of substantially pure title compound. Chromatography of the substantially pure title compound over silica gel and elution with ethyl acetate/acetonitrile/ethanol mixtures afforded 109 mg of pure title compound.

δ (DMSO-$d_6$) 1.16 (3H, d, J=6.2 Hz); 3.2–3.4 (4H, m); 3.91 (1H, dd, J=5.2 and 1.4 Hz); 4.1 (1H, m); 5.17 (2H, s); 5.26 (1H, bs); 5.28 and 5.39 (2H, AB, J=14.3 Hz); 5.77 (1H, d, J=1.4 Hz); 7.36 (2H, d, J=8.6 Hz); 7.50 (1H, br.m); 7.58 (4H, d, J=8.4 Hz); 7.88 (2H, d, J=8.6 Hz); 8.19 (4H, m); 8.57 (1H, m)

EXAMPLE 97

5(R),3-(4-(2-Aminoethyl)carbamoylphenoxy)-6(S)-(1(R)-hydroxyethyl)-7-oxo-4-thia-1-azabicyclo[3,2,0-]hept-2-ene-2-carboxylic acid A mixture of 109 mg of 4-nitrobenzyl 5(R),6(S)-(1(R)-hydroxyethyl)-3-(4-(4-nitrobenzyloxycarbonylaminoethyl)carbamoylphenoxy)-7-oxo-4-thia-1-azabicyclo[3,2,0]hept-2-ene-2-carboxylate, 15.4 mg of potassium bicarbonate, 75 mg of 10% palladium on charcoal, 5 ml of water and 5 ml of dioxane was hydrogenolysed at about 300 kPa (45 psi) for 90 minutes. 1 ml of acetic acid was added and the mixture filtered through 2 g of Hyflo (Trade Mark). The filter pad was washed with further portions of dioxane and water; the combined filtrate was lyophilised to afford 104 mg of a solid. A slurry of this solid in 10 ml of water and 100 μl of formic acid was applied to a HP-20 (Trade Mark) column; elution with water/ethanol mixtures afforded 30 mg of the title compound as a white solid.

δ ($D_2O$) 1.26 (3H, d, J=6.4 Hz); 3.22 (2H, t, J=6 Hz); 3.67 (2H, t, J=6 Hz); 3.92 (1H, dd, J=1.2 and 5 Hz); 4.2 (1H, m); 5.66 (1H, d, J=1.2 Hz); 7.28 and 7.81 (4H, AA'BB', J=8.8 Hz).

EXAMPLE 98

4-Nitrobenzyl 5(R),6(S)-(1(R)-hydroxyethyl)-3-(4-(2-hydroxyethyl)carbamoylphenoxy)-7-oxo-4-thia-1-azabicyclo[3,2,0-]hept-2-ene-2-carboxylate To a suspension of 100 mg of 4-nitrobenzyl 5(R),3-(4-carboxyphenoxy)-6(S)-(1(R)-hydroxyethyl)-7-oxo-4-thia-1-azabicyclo[3,2,0]hept-2-ene-2-carboxylate in dry dichloromethane at −20° C. was added 27 μl of N-methylmorpholine. The mixture was stirred for 5 minutes, then 32.8 μl of trimethylacetyl bromide was added; after 30 minutes at −20° C. 27 μl of N-methylmorpholine was added, followed by 30 μl of ethanolamine. After 30 minutes at −20° C., the reaction mixture was warmed to room temperature, partitioned between dichloromethane and water, the organic layer was washed successively with 1M-citric acid solution, water, saturated sodium bicarbonate solution, and brine, dried over magnesium sulphate and the solvent removed in vacuo. Chromatography over silica gel using ethyl acetate/hexane mixtures as eluant afforded 40 mg of the title compound as a pale yellow solid.

$v_{max}$ Kbr disc 1781 $cm^{-1}$.

δ ($CDCl_3$) 1.16 (3H, d, J=6.2 Hz); 3.74 (2H, m); 3.88 (1H, dd, J=1.2 and 6.2 Hz); 3.92 (2H, m); 4.34 (1H, m); 5.28 and 5.50 (2H, AB, J=14 Hz); 5.67 (1H, d, J=1.2 Hz) 6.66 (1H, m); 7.28 and 7.90 (4H, AA'BB', J=8.9 Hz); 7.60 and 8.24 (4H, AA'BB', J=8.7 Hz).

EXAMPLE 99

Potassium 5(R),6(S)-(1(R)-hydroxyethyl)-3-(4-(2-hydroxyethyl)-carbamoylphenoxy)-7-oxo-4-thia-1-azabicyclo[3,2,0-]hept-2-ene-2-carboxylate A mixture of 70 mg of 4-nitrobenzyl 5(R), 6(S)-(1(R)-hydroxyethyl)-3-(4-(2-hydroxyethyl)carbamoylphenoxy)-7-oxo-4-thia-1-azabicyclo[3,2,0]hept-2-ene-2-carboxylate, 70 mg of 10% palladium on charcoal, 5 ml of dioxane, 13.3 mg of potassium bicabonate and 5 ml of water was hydrogenolysed at about 300 kPa (45 psi) for 1 hour, and then filtered through diatomaceous earth. Lyophilisation of the filtrate afforded 50 mg of a yellow solid, which was dissolved in water and extracted with ethyl acetate. Lyophilisation of the water layer afforded 35 mg of the title product as a pale yellow solid.

δ ($D_2O$) 1.30 (3H, d, J=6.2 Hz); 3.51 (2H, m); 3.75 (2H, m); 3.94 (1H, dd, J=1.3 and 6.2 Hz); 4.25 (1H, m); 5.70 (1H, d, J=1.3 Hz); 6.90 (1H, m); 7.30 and 7.79 (4H, AA'BB', J=8.9 Hz).

EXAMPLE 100

4-Nitrobenzyl 5(R),3-[4-(N-(N-(carbamoylmethyl)carbamoylmethyl)-carbamoyl)phenoxy]-6(S)-[1(R)-hydroxyethyl]-7-oxo-4-thia-1-azabicyclo[3.2.0]hept-2-ene-2-carboxylate 49 μl of triethylamine were added to a stirred solution of 190 mg of 4-nitrobenzyl 5(R),6(S)-[1(R)-hydroxyethyl]-7-oxo-3-[4-(pentafluorophenoxycarbonyl)phenoxy]-4-thia-1-azabicyclo[3.2.0]hept-2-ene-2-carboxylate and glycylglycinamide hydrochloride (59 mg) in 5 ml of dry dimethylformamide. Stirring was continued at room temperature until reaction was complete (as judged by t.l.c.) when the mixture was partitioned between ethyl acetate and water. The aqueous layer was extracted with ethyl acetate and the combined organic layers washed with water and brine, dried and evaporated. The solid residue was extracted with hexane to leave the title compound as a grey solid (117 mg).

δ ($d_6$-DMSO) 1.16 (3H, d, J=7.0 Hz); 3.63 (2H, d, J=5.7 Hz); 3.85–4.03 (3H, m); 5.20–5.53 (3H, m); 5.78 (1H, d, J=1.3 Hz); 7.10 (1H, br. s); 7.23 (1H, br. s); 7.45 (1H, br. s); 7.40,7.93 (4H, AA'BB', J=8.7 Hz); 7.60,8.19 (4H, AA'BB', J=8.8 Hz); 8.89 (1H, br. t).

EXAMPLE 101

Potassium 5(R),3-[4-(N-(N-(carbamoylmethyl)carbamoylmethyl)-carbamoyl)phenoxy]-6(S)-[1(R)-hydroxyethyl]-7-oxo-4-thia-1-azabicyclo[3.2.0]hept-2-ene-2-carboxylate 90 mg of the above compound were obtained from 168 mg of the corresponding 4-nitrobenzyl carboxylate defined Example 100 by a procedure analogous to that described in Example 58, using 28.1 mg of potassium bicarbonate.

$\nu_{max}$ (KBr disc) 1780 cm$^{-1}$.

δ (D$_2$O) 1.29 (3H, d, J=6.4 Hz); 3.94 (2H, s); 3.96 (1H, dd, J=1.0 and 5.6 Hz); 4.14 (2H, s); 4.20–4.31 (1H, m); 5.71 (1H, d, J=1.0 Hz); 7.32,7.86 (4H, AA'BB', J=8.8 Hz).

EXAMPLE 102

4-Nitrobenzyl 5(R),6(S)-[1(R)-hydroxyethyl]-3-[4-(1-(1-(4-nitrobenzyloxycarbonyl)ethylcarbamoyl)ethylcarbamoyl)-phenoxy]-7-oxo-4-thia-1-azabicyclo[3.2.0]hept-2-ene-2-carboxylate 77.0 mg of the title compound were obtained by a procedure analogous to that described in Example 96 using 100 mg of 4-nitrobenzyl 5(R),3-(4-carboxy-phenoxy)-6(S)-[1(R)-hydroxyethyl]-7-oxo-4-thia-1-azabicyclo[3.2.0]hept-2-ene-2-carboxylate, 77.0 mg of 1-hydroxybenzotriazole hydrate, 78.0 mg of 1-(3-dimethylaminopropyl)-3-ethylcarbodiimide hydrochloride, 114.3 μl of triethylamine and 91.8 mg of L-alanyl-L-alanine 4-nitrobenzyl ester p-toluenesulphonate salt.

δ (d$_6$-DMSO) 1.10 (3H, d, J=5.7 Hz); 1.20–1.40 (6H, m); 3.62 (1H, br.s); 3.92 (1H, dd, J=1.3, 5.7 Hz); 3.92–4.10 (1H, m); 4.0–4.54 (2H, m); 5.26 (2H, s); 5.28,5.40 (2H, ABq, J=14 Hz); 5.77 (1H, d, J=1.3 Hz); 7.37, 7.94 (4H, AA'BB', J=8.8 Hz); 7.52–7.66 (4H, m); 8.14–8.28 (4H, m); 8.50 (1H, d, J=6.7 Hz); 8.58 (1H, d, J=7.4 Hz).

EXAMPLE 103

Dipotassium 5(R),3-[4-(1-(1-carboxyethylcarbamoyl)ethylcarbamoyl)phenoxy]-6(S)-[1(R)-hydroxyethyl]-7-oxo-4-thia-1-azabicyclo[3.2.0]hept-2-ene-2-carboxylate 17.8 mg of the above compound were obtained by a procedure analogous to that described in Example 99 using 77.0 mg of the 4-nitrobenzyl carboxylate defined in Example 102, 80 mg of 10% palladium on charcoal, 10 mg of dioxane, 20 mg of potassium bicarbonate and 10 ml of water.

δ (D$_2$O) 1.20–1.58 (9H, m); 3.95 (1H, dd, J=1.1, 5.3 Hz); 4.05–4.60 (3H, m); 5.73 (1H, d, J=1.1 Hz); 7.30, 7.84 (4H, AA'BB', J=8.8 Hz).

EXAMPLE 104

4-Nitrobenzyl 5(R),6(S)-[1(R)-hydroxyethyl]-3-[4-(N-(1-(4-nitrobenzyloxycarbonyl)-2-phenylethyl)carbamoyl)phenoxy]-7-oxo-4-thia-1-azabicyclo[3.2.0]hept-2-ene-2-carboxylate 144 mg of the above compound were obtained by a procedure analogous to that described in Example 61 using 224 mg of 4-nitrobenzyl 5(R),3-[4-(4-chlorophenylthio(carbonyl))phenoxy]-6(S)-[1(R)-hydroxyethyl]-7-oxo-4-thia-1-azabicyclo[3.2.0]hept-2-ene-2-carboxylate, 141 mg of silver trifluoromethanesulphonate, 334 mg of D,L-phenylalanine 4-nitrobenzyl ester p-toluenesulphonate salt and 74 mg of triethylamine in dimethylformamide. The product was eluted from a silica gel column using ethyl acetate/hexane mixtures as eluants and obtained as a pale yellow foam.

δ (CDCl$_3$) 1.36 (3H, d, J=6.3 Hz); 3.26 (2H, d, J=6.3 Hz); 3.79 (1H, dd, J=6.6 and 1.1 Hz); 4.26 (1H, t, J=6.3 Hz); 5.05–5.50 (5H, m); 5.68 (1H, d, J=1.1 Hz); 7.05–7.35 (6H, m); 7.16,7.72 (4H, AA'BB', J=8.6 Hz); 7.40,8.15 (4H, AA'BB', J=8.8 Hz); 7.50, 8.19 (4H, AA'BB', J=8.6 Hz).

EXAMPLE 105

Dipotassium 5(R),6(S)-[1(R)-hydroxyethyl]-3-[4-(N-(1-carboxylato-2-phenylethyl)carbamoyl)phenoxy]-7-oxo-4-thia-1-azabicyclo[3.2.0]hept-2-ene-2-carboxylate 25 mg of the above compound were obtained by a procedure analogous to that described in Example 58 using 96.5 mg of the 4-nitrobenzyl carboxylate defined in Example 104, 25 mg of potassium bicarbonate and 95 mg of 10% palladium-on-carbon catalyst.

δ (D$_2$O) 1.30 (3H, d, J=6.4 Hz); 3.25–3.37 (2H, m); 3.96 (1H, dd, J=5.9 and 1.0 Hz); 4.14–4.30 (1H, m); 4.76–5.00 (1H, m); 5.71 (1H, d, J=1.0 Hz); 7.20–7.45 (7H, m); 7.65–7.75 (2H, m).

EXAMPLE 106

4-Nitrobenzyl 5(R),3-[4-(N-(1-carbamoyl-2-hydroxyethyl)carbamoyl)-phenoxy]-6(S)-[1(R)-hydroxyethyl]-7-oxo-4-thia-1-azabicyclo[3.2.0]hept-2-ene-2-carboxylate A mixture of 205 mg of 5(R),3-[4-(4-chlorophenylthio(carbonyl))phenoxy]-6(S)-[1(R)-hydroxyethyl]-7-oxo-4-thia-1-azabicyclo[3.2.0]hept-2-ene-2-carboxylate, 127 mg of silver trifluoromethanesulphonate, 70 mg of L-serinamide hydrochloride and 68 mg of triethylamine in 3 ml of dimethylformamide was stirred in the dark at 20° C. until reaction was complete. The mixture was diluted with ethyl acetate, washed with water and dried (anhydrous magnesium sulphate). Evaporation of the filtered mixture afforded a residue which, on chromatography on 10% deactivated silica gel using hexane/ethyl acetate mixtures as eluant, gave the title compound as a white solid (63 mg).

δ (DMSO-d$_6$) 1.17 (3H, d, J=6.2 Hz); 3.70 (2H, m); 3.91 (1H, dd, J=5.8 and 1.3 Hz); 3.94–4.05 (1H, m); 4.35–4.55 (1H, m); 4.91 (1H, t, J=5.9 Hz); 5.24, 5.39 (2H, ABq, J=14.8 Hz); 5.71 (1H, d, J=1.3 Hz); 7.12 (1H, br.s); 7.41 (1H, br.s); 7.40, 7.97 (4H, AA'BB', J=8.8 Hz); 7.60, 8.19 (4H, AA'BB', J=8.8 Hz); 8.28 (1H, br.d, J=7.9 Hz).

EXAMPLE 107

Potassium 5(R),3-[4-((1-carbamoyl-2-hydroxyethyl)carbamoyl)-phenoxy]-6(S)-[1(R)-hydroxyethyl]-7-oxo-4-thia-1-azabicyclo[3.2.0]hept-2-ene-2-carboxylate A mixture of 95.6 mg of the 4-nitrobenzyl carboxylate described in Example 106, 16.7 mg of potassium bicarbonate and 95 mg of 10% palladium-on-carbon catalyst in 10 ml of water and 10 ml of ethyl acetate was hydrogenated at about 345 kPa (50 psi) until reaction was complete. The mixture was filtered through Celite (Trade Mark), the aqueous layer extracted with ethyl acetate and finally lyophilised to afford the title compound as a pale grey powder (54 mg).

δ (DMSO-d$_6$) 1.17 (3H, d, J=6.2 Hz); 3.63 (1H, dd, J=5.9 and 1 Hz); 3.60–3.75 (2H, m); 3.83–4.03 (1H, m); 4.35–4.48 (1H, m); 5.20 (1H, br.d, J=5.0 Hz); 5.60 (1H, d, J=1 Hz); 7.01 (1H, br.s); 7.47 (1H, br.s); 7.11,7.91 (4H, AA'BB', J=8.7 Hz); 8.64 (1H, br.d, J=7.6 Hz).

EXAMPLE 108

4-Nitrobenzyl 5(R),3-[4-((N-(4-nitrobenzyloxycarbonylmethyl)carbamoyl)methylcarbamoyl)phenoxy]-6(S)-[1(R)-hydroxyethyl]-7-oxo-4-thia-1-azabicyclo[3.2.0]hept-2-ene-2-carboxylate 50 μl of triethylamine was added to a stirred solution of 155 mg of 4-nitrobenzyl 5NR),3-[4-(pentafluorophenoxycarbonyl)phenoxy]-6(S)-[1(R)-hydroxyethyl]-7-oxo-4-thia-1-azabicyclo-[3.2.0]hept-2-ene-2-carboxylate and 151 mg of 4-nitrobenzyl glycylglycinate p-toluenesulphonate salt in acetonitrile. The mixture was stirred until reaction was complete, the solvent was partially removed, ethyl acetate added and the organic solution washed successively with water and brine, and dried over magnesium sulphate. The filtered solution was evaporated to dryness and the residue chromatographed on deactivated silica gel using hexane/ethyl acetate/methanol mixtures as eluant to afford 103 mg of the title compound.

$\nu_{max}$ (CDCl$_3$) 1794 cm$^{-1}$.

δ (DMSO-d$_6$) 1.16 (3H, d, J=6.3 Hz); 3.31 (2H, s); 3.33 (2H, s); 3.92–4.06 (2H, m); 5.28 (2H, br.s); 5.28,5.40 (2H, ABq, J=13.9 Hz), 5.78 (1H, d, J=1.0 Hz); 7.40,7.95 (4H, AA'BB', J=8.8 Hz); 7.59,8.18 (4H, AA'BB', J=8.8 Hz); 7.65,8.23 (4H, AA'BB', J=8.7 Hz); 8.45 (1H, br.s); 8.89 (1H, br.s)

EXAMPLE 109

Potassium 5(R),3-[4-((N-carboxymethylcarbamoyl)methylcarbamoyl)phenoxy]-6(S)-[1(R)-hydroxyethyl]-7-oxo-4-thia-1-azabicyclo[3.2.0]hept-2-ene-2-carboxylate 45 mg of the above compound were obtained from 100 mg of the corresponding 4-nitrobenzyl carboxylate defined in Example 108 by a procedure analogous to that described in Example 58, using 13.6 mg of potassium bicarbonate.

$\nu_{max}$ (KBr) 1770 cm$^{-1}$.

δ (D$_2$O) 1.28 (3H, d, J=6.4 Hz); 3.77 (2H, s); 3.94 (1H, dd, J=1.1 Hz and 5.9 Hz); 4.12 (2H, s); 4.25–4.34 (1H, m); 5.69 (1H, d, J=1.1 Hz); 7.38,7.85 (4H, AA'BB', J=8.8 Hz).

EXAMPLE 110

4-Nitrobenzyl 5(R),3-[4-((5-amino-(4-nitrobenzyloxycarbonyl)pentyl)carbamoyl)phenoxy]-6(S)-[1(R)-hydroxyethyl]-7-oxo-4-thia-1-azabicyclo[3.2.0]hept-2-ene-2-carboxylate 325 μl of triethylamine was added to a stirred solution of 127 mg of 4-nitrobenzyl 5(R),3-[4-(pentafluorophenoxycarbonyl)phenoxy]-6(S)-[1(R)-hydroxyethyl]-7-oxo-4-thia-1-azabicyclo[3.2.0]hept-2-ene-2-carboxylate and 350 mg of L-lysine 4-nitrobenzyl ester bis-(toluenesulphonate) salt in acetonitrile. The mixture was stirred until reaction was complete, ethyl acetate was added and the organic solution washed successively with water and brine, and dried over magnesium sulphate. The filtered solution was evaporated to dryness and the residue chromatographed on deactivated silica gel using hexane/ethyl acetate/methanol mixtures as eluant to afford 105 mg of the title compound.

$\nu_{max}$ 1735, 1785 cm$^{-1}$.

δ (DMSO-d$_6$) 1.16 (3H, d, J=7.0 Hz); 1.28–1.70 (6H, m); 3.14–3.48 (3H, m); 3.91 (1H, dd, J=1.1 Hz and 5.8 Hz); 5.25 (2H, br.s); 5.27,5.40 (2H, ABq, J=14.2 Hz); 5.77 (1H, d, J=1.3 Hz); 7.35,7.88 (4H, AA'BB', J=8.7 Hz); 7.56–7.65 (4H, m); 8.15–8.24 (4H, m); 8.49 (1H, t, J=5.4 Hz).

EXAMPLE 111

Potassium 5(R),3-[4-((5-amino-5-carboxypentyl)carbamoyl)phenoxy]-6(S)-[1(R)-hydroxyethyl]-7-oxo-4-thia-1-azabicyclo[3.2.0]hept-2-ene-2-carboxylate 42 mg of the above compound were obtained from 100 mg of the 4-nitrobenzyl carboxylate defined in Example 110 by a procedure analogous to that described in Example 58, using 13.6 mg of potassium bicarbonate.

$\nu_{max}$ (KBr) 1770 cm$^{-1}$.

δ (D$_2$O) 1.28 (3H, d, J=6.3 Hz); 1.33–1.85 (6H, m); 3.27–3.44 (2H, m); 3.69 (1H, t, J=5.8 Hz); 3.92 (1H, dd, J=1.0 Hz and 6.1 Hz); 4.22–4.32 (1H, m); 5.68 (1H, d, J=1.0 Hz); 7.29,7.78 (4H, AA'BB', J=8.3 Hz).

EXAMPLE 112

4-Nitrobenzyl 5(R),3-[4-((2-(carboxymethylamino)ethyl)carbamoyl)phenoxy]-6(S)-[1(R)-hydroxyethyl]-7-oxo-4-thia-1-azabicyclo[3.2.0]hept-2-ene-2-carboxylate 132 μl of triethylamine was added to a stirred solution of 155 mg of 4-nitrobenzyl 5(R),3-[4-(pentafluorophenoxycarbonyl)phenoxy]-6(S)-[1(R)-hydroxyethyl]-7-oxo-4-thia-1-azabicyclo[3.2.0]hept-2-ene-2-carboxylate and 56 mg of N-(2-aminoethyl)glycine in dimethylformamide. The mixture was stirred until reaction was complete, ethyl acetate added and the organic solution washed successively with water and brine, and dried over magnesium sulphate. The filtered solution was evaporated to leave 92 mg of the title compound.

$\nu_{max}$ (CDCl$_3$) 1778 cm$^{-1}$.

δ (d$_6$-acetone) 1.29 (3H, d, J=6.3 Hz); 3.36–3.70 (6H, m); 3.89 (1H, dd, J=1.5 Hz and 6.3 Hz); 4.13–4.23 (1H, m); 5.25,5.42 (2H, ABq, J=14.1 Hz); 5.83 (1H, d, J=1.5 Hz); 7.31,7.95 (4H, AA'BB', J=8.8 Hz); 7.63,8.17 (4H, AA'B', J=8.8 Hz).

EXAMPLE 113

Potassium 5(R),3-[4-((2-(carboxymethylamino)ethyl)carbamoyl)phenoxy]-6(S)-[1(R)-hydroxyethyl]-7-oxo-4-thia-1-azabicyclo[3.2.0]hept-2-ene-2-carboxylate 49 mg of the above compound were obtained from 92 mg of the 4-nitrobenzyl carboxylate defined in Example 112 by a procedure analogous to that described in Example 58, using 15.7 mg of potassium bicarbonate.

$\nu_{max}$ (KBr) 1769 cm$^{-1}$.

δ (D$_2$O) 1.33 (3H, d, J=6.4 Hz); 3.42–3.74 (6H, m); 3.96 (1H, dd, J=0.9 Hz and 6.1 Hz); 4.23–4.33 (1H, m); 5.72 (1H, d, J=0.9 Hz); 7.27,7.74 (4H, AA'BB', J=8.8 Hz).

EXAMPLE 114

4-Nitrobenzyl 5(R),6(S)-[1(R)-hydroxyethyl]-3-[4-((N-methylcarbamimidoylamino)carbonyl)phenoxy]-7-oxo-4-thia-1-azabicyclo[3.2.0]hept-2-ene-2-carboxylate 35 μl of triethylamine was added to a stirred solution of 84 mg of 4-nitrobenzyl 5(R),3-[4-(pentafluorophenoxycarbonyl)phenoxy]-6(S)-[1(R)-hydroxyethyl]-7-oxo-4-thia-1-azabicyclo[3.2.0]hept-2-ene-2-carboxylate, 49 mg of silver trifluoromethanesulphonate and 27 mg of methylguanidine hydrochloride in acetonitrile. The mixture was stirred in the dark until reaction was complete, ethyl acetate added and the organic solution washed successively with water and brine, and dried over magnesium sulphate. The filtered solution was evaporated to dryness and the residue chromatographed on deactivated silica gel using hexane/ethyl acetate/methanol mixtures as eluant to afford 29 mg of the title compound.

$\nu_{max}$ (CDCl$_3$) 1784 cm$^{-1}$.

δ (d$_6$-acetone) 1.31 (3H, d, J=6.3 Hz); 2.98 (3H, d, J=4.4 Hz); 3.90 (1H, dd, J=1.2 Hz and 6.1 Hz); 4.18–4.27 (1H, m); 5.31,5.38 (2H, ABq, J=14.2 Hz); 5.83 (1H, d, J=1.2 Hz); 7.26,8.21 (4H, AA'BB', J=8.7 Hz); 7.68,8.22 (4H, AA'BB', J=8.9 Hz).

EXAMPLE 115

Potassium 5(R),6(S)-[1(R)-hydroxyethyl]3-[4-((N-methylcarbamimidoylamino)carbonyl)phenoxy]-7-oxo-4-thia-1-azabicyclo[3.2.0]hept-2-ene-2-carboxylate 30 mg of the above compound were obtained from 68 mg of the 4-nitrobenzyl carboxylate defined in Example 114 by a procedure analogous to that described in Example 58, using 12.6 mg of potassium bicarbonate.

δ (D$_2$O) 1.25 (3H, d, J=6.4 Hz); 2.85 (3H, s); 3.90 (1H, dd, J=1.2 Hz and 6.1 Hz); 4.18–4.23 (1H, m); 6.15 (1H, d, J=1.2 Hz); 7.22,7.93 (4H, AA'BB', J=8.9 Hz).

EXAMPLE 116

4-Nitrobenzyl 5(R),3-[4-((2-amino-2-(4-nitrobenzyloxycarbonyl)ethyl)carbamoyl)phenoxy]-6(S)-[1(R)-hydroxyethyl]-7-oxo-4-thia-1-azabicyclo[3.2.0]hept-2-ene-2-carboxylate 88 μl of triethylamine was added to a stirred solution of 173 mg of 4-nitrobenzyl 5(R),3-[4-(pentafluorophenoxycarbonyl)phenoxy]-6(S)-[1(R)-hydroxyethyl]-7-oxo-4-thia-1-azabicyclo[3.2.0]hept-2-ene-2-carboxylate and 187 mg of 4-nitrobenzyl 2,3-diaminopropionate ditosylate in dimethylformamide. The mixture was stirred until reaction was complete, ethyl acetate added and the organic solution washed successively with water and brine, and dried over magnesium sulphate. The filtered solution was evaporated to leave 168 mg of the title compound as a yellow solid.

$\nu_{max}$ (CDCl$_3$) 1745, 1784 cm$^{-1}$.

δ (DMSO-d$_6$) 1.17 (3H, d, J=6.7 Hz); 3.56–3.67 (2H, m); 3.78 (1H, t, J=6.2 Hz); 3.92 (1H, dd, J=1.3 Hz and 5.7 Hz); 4.05–4.14 (1H, m); 5.23 (2H, br.s); 5.40,5.27 (2H, ABq, J=14.2 Hz); 5.78 (1H, d, J=1.3 Hz); 7.35,7.85 (4H, AA'BB', J=8.7 Hz); 7.56–7.67 (4H, m); 8.11–8.22 (4H, m); 8.65 (1H, m).

EXAMPLE 117

Dipotassium 5(R),3-[4-((2-amino-2-carboxyethyl)carbamoyl)phenoxy]-6(S)-[1(R)-hydroxyethyl]-7-oxo-4-thia-1-azabicyclo[3.2.0]hept-2-ene-2-carboxylate 90 mg of the above compound were obtained from 168 mg of the 4-nitrobenzyl carboxylate defined in Example 116 by a procedure analogous to that described in Example 58, using 23.8 mg of potassium bicarbonate.

$\nu_{max}$ 1763 cm$^{-1}$.

δ (D$_2$O) 1.27 (3H, d, J=6.3 Hz); 3.65–3.92 (3H, m); 3.93 (1H, dd, J=1.3 Hz and 5.6 Hz); 4.23–4.34 (1H, m); 5.68 (1H, d, J=1.3 Hz); 7.28,7.79 (4H, AA'BB', J=8.3 Hz).

EXAMPLE 118

4-Nitrobenzyl 5(R),3-[4-((N-hydroxycarbamoyl)methylcarbamoyl)phenoxy]-6(S)-[1(R)-hydroxyethyl]-7-oxo-4-thia-1-azabicyclo[3.2.0]hept-2-ene-2-carboxylate 27 mg of glycine hydroxamate was added to a stirred solution of 163 mg of 4-nitrobenzyl 5(R),3-[4-(pentafluorophenoxycarbonyl)phenoxy]-6(S)-[1(R)-hydroxyethyl]-7-oxo-4-thia-1-azabicyclo[3.2.0]hept-2-ene-2-carboxylate in dimethylformamide. The mixture was stirred until reaction was complete, ethyl acetate added and the organic solution washed successively with water and brine, and dried over magnesium sulphate. The filtered solution was evaporated to dryness and the residue chromatographed on deactivated silica gel using hexane/ethyl acetate/methanol mixtures as eluant to afford 104 mg of the title compound.

δ (DMSO-d$_6$) 1.16 (3H, d, J=6.3 Hz); 3.78 (2H, d, J=5.5 Hz); 3.92 (1H, dd, J=1.2 Hz and 5.8 Hz); 4.02–4.12 (1H, m); 5.28,5.40 (2H, ABq, J=14.2 Hz); 5.78 (1H, d, J=1.0 Hz); 7.38,7.93 (4H, AA'BB', J=8.8 Hz); 7.59,8.18 (4H, AA'BB', J=8.7 Hz); 8.82 (1H, t, J=5.4 Hz); 10.6 (1H, br.s).

EXAMPLE 119

Potassium 5(R),3-[4-((N-hydroxycarbamoyl)methylcarbamoyl)phenoxy]-6(S)-[1(R)-hydroxyethyl]-7-oxo-4-thia-1-azabicyclo[3.2.0]hept-2-ene-2-carboxylate A mixture of a solution of 104 mg of 4-nitrobenzyl 5(R),3-[4-((N-hydroxycarbamoyl)methylcarbamoyl)phenoxy]-6(S)-[1(R)-hydroxyethyl]-7-oxo-4-thia-1-azabicyclo[3.2.0]hept-2-ene-2-carboxylate, and 18.6 mg of potassium bicarbonate in water, and 104 mg of 10% palladium/charcoal was hydrogenated at about 3.5 barr (50 p.s.i.), until reaction was complete. The mixture was filtered through Celite (Trade Mark), the organic layer separated and the aqueous layer lyophilised to afford 70 mg of the title compound as an off-white solid.

$\nu_{max}$ (KBr) 1765 (cm$^{-1}$).

δ (D$_2$O) 1.27 (3H, d, J=6.4 Hz); 3.90 (1H, dd, J=1.1 and 5.5 Hz); 4.04–4.12 (2H, m); 4.24–4.31 (1H, m); 5.68 (1H, d, J=1.1 Hz); 7.29,7.84 (4H, AA'BB', J=8.3 Hz).

EXAMPLE 120

4-Nitrobenzyl 5(R),3-[4-((1-carbamoylethyl)carbamoyl)phenoxy]-6(S)-[1(R)-hydroxyethyl]-7-oxo-4-thia-1-azabicyclo[3.2.0]hept-2-ene-2-carboxylate 32 μl of triethylamine was added to a stirred solution of 125 mg of 4-nitrobenzyl 5(R),3-[4-(pentafluorophenoxycarbonyl)phenoxy]-6(S)-[1(R)-hydroxyethyl]-7-oxo-4-thia-1-azabicyclo[3.2.0]hept-2-ene-2-carboxylate and 39 mg of alaninamide hydrobromide in acetonitrile. The mixture was stirred until reaction was complete, the solvent was partially removed, ethyl acetate added and the organic solution washed successively with water and brine, and dried over magnesium sulphate. The filtered solution was evaporated to dryness and the residue chromatographed on deactivated silica gel using hexane/ethyl acetate mixtures as eluant to afford 75 mg of the title compound.

δ (DMSO-d₆) 1.16 (3H, d, J=6.2 Hz); 1.32 (3H, 2xd, J=7.5 Hz); 3.91 (1H, dd, J=0.8 Hz and 5.5 Hz); 4.01–4.14 (1H, m); 4.39–4.45 (1H, m); 5.27–5.40 (2H, ABq, J=14.9 Hz); 5.77 (1H, d, J=0.8 Hz); 7.37,7.95 (4H, AA'BB', J=8.7 Hz); 7.59,8.18 (4H, AA'BB', J=8.7 Hz); 8.48 (1H, t, J=7.5 Hz).

EXAMPLE 121

Potassium 5(R),3-[4-((1-carbamoylethyl)carbamoyl)phenoxy]-6(S)-[1(R)-hydroxyethyl]-7-oxo-4-thia-1-azabicyclo[3.2.0]hept-2-ene-2-carboxylate 40 mg of the above compound were obtained from 70 mg of the 4-nitrobenzyl carboxylate defined in Example 120 by a procedure analogous to that described in Example 58, using 15.3 mg of potassium bicarbonate.

$v_{max}$ (KBr) 1769 cm⁻¹.

δ (D₂O) 1.27 (3H, d, J=6.3 Hz); 1.50–1.57 (3H, m); 3.92 (1H, dd, J=1.1 Hz and 5.8 Hz); 4.25–4.34 (1H, m); 4.41–4.52 (1H, m); 5.68 (1H, d, J=1.1 Hz); 7.28,7.81 (4H, AA'BB', J=8.8 Hz).

EXAMPLE 122

4-Nitrobenzyl 5(R),6(S)-[1(R)-hydroxyethyl]-3-[4-((2-methylsulphonylethyl)carbamoyl)phenoxy]-7-oxo-4-thia-1-azabicyclo[3.2.0]hept-2-ene-2-carboxylate 112 mg of the title compound were obtained by a procedure analogous to that described in Example 96 using 100 mg of 4-nitrobenzyl 5(R),3-(4-carboxyphenoxy)-6(S)-[1(R)-hydroxyethyl]-7-oxo-4-thia-1-azabicyclo[3.2.0]hept-2-ene-2-carboxylate, 78.6 mg of 1-hydroxybenzotriazole hydrate, 77 mg of 1-(3-dimethylaminopropyl)-3-ethylcarbodiimide hydrochloride, 256 μl of triethylamine and 64 mg of 2-methylsulphonylethylamine hydrochloride.

$v_{max}$ (Nujol* mull) 1775, 1790 cm⁻¹.
* "Nujol" is a Trade Mark.

δ (DMSO-d₆) 1.18 (3H, d, J=5.8 Hz); 3.04 (3H, s); 3.38 (2H, m); 3.70 (2H, m); 3.90 (1H, dd, J=1.1 and 5.8 Hz); 4.05 (1H, m); 5.32 (3H, m); 5.80 (1H, d, J=1.1 Hz) 7.39,7.89 (4H, AA'BB', J=8.7 Hz); 7.58,8.19 (4H, AA'BB', J=8.8 Hz); 8.79 (1H, br.t).

EXAMPLE 123

Potassium 5NR),6(S)-[1(R)-hydroxyethyl]-3-[4-((2-methylsulphonylethyl)carbamoyl)phenoxy]-7-oxo-4-thia-1-azabicyclo[3.2.0]hept-2-ene-2-carboxylate 64 mg of the above compound were obtained from 110 mg of the 4-nitrobenzyl carboxylate defined in Example 122 by a procedure analogous to that described in Example 99, using 100 mg of 10%palladium on charcoal, 5 ml of dioxane, 18.6 mg of potassium bicarbonate and 5 ml of water.

δ(D₂O) 1.27 (3H, d, J=7.0 Hz); 3.12 (3H, s); 3.56 (2H, t); 3.88 (1H, dd, J=1.3 and 7.0 Hz); 3.92 (2H, m); 4.21 (1H, m); 5.68 (1H, d, J=1.3 Hz); 7.30,7.78 (4H, AA'BB' J=8.8 Hz).

EXAMPLE 124

4-Nitrobenzyl 5(R),6(S)-[1l(R)-hydroxyethyl]-3-[4-((2-methylthioethyl)carbamoyl)phenoxy]-7-oxo-4-thia-1-azabicyclo[3.2.0]hept-2-ene-2-carboxylate 195 mg of the title compound were obtained by a procedure analogous to that deescribed in Example 96 using 200 mg of 4-nitrobenzyl 5(R),3-(4-carboxyphenoxy)-6(S)-[1(R)-hydroxyethyl]-7oxo-4-thia-1-azabicyclo[3.2.0]hept-2-ene-2-carboxylate, 154 mg of 1-hydroxybenzotriazole hydrate, 157 mg of 1-(3-dimethylaminopropyl)-3-ethyl-carbodiimide hydrochloride, 576 μl of triethylamine and 74.7 mg of 2-methylthioethylamine.

$v_{max}$ 1788 cm⁻¹.

δ(CDCl₃) 1.38 (3H, d, J=6.3 Hz); 1.70 (1H, br.s); 2.15 (3H, s); 2.80 (2H, m); 3.72 (2H, m); 3.80 (1H, dd, J=1.2 and 6.3 Hz); 5.28,5.48 (2H, ABq, J=14 Hz); 5.70 (1H, d, J=1.2 Hz); 6.68 (1H, m); 7.22,7.88 (4H, AA'BB', J=8.8 Hz); 7.56,8.24 (4H, AA'BB', J=8.9 Hz).

EXAMPLE 125

Potassium 5(R),6(S)-[1(R)-hydroxyethyl]-3-[4-((2-methylthioethyl)carbamoyl)phenoxy]-7oxo-4-thia-1-azabicyclo[3.2.0]hept-2-ene-2-carboxylate 48 mg of the above compound were obtained from 99 mg of the 4-nitrobenzyl carboxylate defined in Example 124 by a procedure analogous to that described in Example 99, using 90 mg of 10% palladium on charcoal, 5 ml of dioxane, 16.1 mg of pastassium bicarbonate and 5 ml of water.

δ (D₂O) 1.24 (3H, d, J=6.3 Hz); 2.10 (3H, s); 2.76 (2H, t); 3.58 (2H, t); 3.90 (1H, dd, J=1.2 and 6.3 Hz); 4.21 (1H, m); 5.65 (1H, d, J=1.2 Hz); 7.25,7.75 (4H, AA'BB', J=8.9 Hz).

EXAMPLE 126

4-Nitrobenzyl 5(R),6(S)-[1(R)-hydroxyethyl]-3-[4-((2-methylsulphinylethyl)carbamoyl)phenoxy]-7-oxo-4-thia-1-azabicyclo[3.2.0]hept-2-ene-2-carboxylate To a stirred solution of 100 mg of 4-nitrobenzyl 5(R),6(S)-[1(R)-hydroxyethyl]-3-[4-((2-methylthioethyl)carbamoyl)phenoxy]-7-oxo-4-thia-1-azabicyclo]3.2.0]hept-2-ene-2-carboxylate in 10 ml of dichloromethane at −70° C. was added a solution of 42.4 mg of meta-chloroperbenzoic acid in 5 ml of dichloromethane. After warming to room temperature, the mixture was stirred for 1 hour and a further 30 ml of dichloromethane added. The organic solution was washed with sodium bicarbonate, brine, dried over anhydrous magnesium sulphate and the filtered solution evaporated to afford 87 mg of the title compound.

$v_{max}$ (KBr) 1780 cm⁻¹.

δ (DMSO-d₆) 1.17 (3H, d, J=6.5 Hz); 2.69 (3H, s); 2.90–3.15 (2H, m); 3.62 (2H, m); 3.90 (1H, dd, J=1.2 and 6.5 Hz); 5.30 (3H, m); 5.73 (1H, d, J=1.2 Hz); 7.37,7.88 (4H, AA'BB', J=8.9 Hz); 7.68,8.18 (4H, AA'BB', J=8.8 Hz).

EXAMPLE 127

Potassium 5(R),6(S)-[1(R)-hydroxyethyl]-3-[4-((2-methylsulphinylethyl)carbamoyl)phenoxy]-7-oxo-4-thia-1-azabicyclo[3.2.0]hept-2-ene-2-carboxylate 51 mg of the title compound were obtained from 80 mg of the 4-nitrobenzyl carboxylate defined in Example 126 by a procedure analogous to that described in Example 99, using 80 mg of 10% palladium on charcoal, 5 ml of dioxane, 13.9 mg of potassium bicarbonate and 5 ml of water. δ (D₂O) 1.27 (3H, d, J=6.4 Hz); 2.74 (3H, s); 3.18 (2H, m); 3.82 (2H, t, J=6.1 Hz); 3.91 (1H, dd, J=1.1 and 6.4 Hz); 4.21 (1H, m); 5.68 (1H, d, J=1.1 Hz); 7.28,7.68 (4H, AA'BB', J=8.7 Hz).

EXAMPLE 128

4-Nitrobenzyl 5(R),3-[4-((cyanomethyl)carbamoyl)phenoxy]-6(S)-[1(R)-hydroxyethyl]-7-oxo-4-thia-1-azabicyclo[3.2.0-]hept-2-ene-2-carboxylate 100 mg of the title compound were obtained by a procedure analogous to that described in Example 96 using 100 mg of 4-nitrobenzyl 5(R),3-[4-carboxy)-phenoxy]-6(S)-[1(R)-hydroxyethyl]-7-oxo-4-thia-1azabicyclo[3.2.0]hept-2-ene-2carboxylate, 79 mg of 1-hydroxybenzotriazole hydrate, 77 mg of 1-(3-dimethylaminopropyl)-3-ethylcarbodiimide hydrochloride, 256 μl of triethylamine and 38 mg of aminoacetonitrile hydrochloride.

$\nu_{max}$ (KBr) 1791 cm$^{-1}$.

δ (DMSO-d$_6$) 1.19 (3H, d, J=6.3 Hz); 3.92 (1H, dd, J=1.1 and 6.3 Hz); 4.05 (1H, m); 4.34 (2H, d, J=5.3 Hz); 5.30 (3H, m); 5.78 (1H, d, J=1.1 Hz); 7.40,7.93 (4H, AA'BB', J=8.8 Hz); 7.57,8.17 (4H, AA'BB', J=8.9 Hz); 9.25 (1H, br.t).

EXAMPLE 129

Potassium 5(R),3-[4-((cyanomethyl)carbamoly)phenoxy]-6(S)-[1(R)-hydroxyethyl]-7-oxo-4-thia-1-azabicyclo]3.2.0-]hept-2-ene-2-carboxylate 49 mg of the title compound were obtained from 100 mg of the 4-nitorbenzyl carboxylate defined in Example 128 by a procedure analogous to that described in Example 99, using 50 mg of 10% palladium on charcoal, 5 ml of dioxane, 19.1 mg of potassium bicarbonate and 5 ml of water. δ (D$_2$O) 1.28 (3H, d, J=6.4 Hz); 3.93 (2H, dd, J=1.1 and 6.2 Hz); 4.25 (1H, m); 4.80 (2H, d, J=9.2 Hz); 5.68 (1H, d, J=1.1 Hz); 7.30,7.81 (4H, AA'BB', J=8.8 Hz).

EXAMPLE 130

4-Nitrobenzyl 5(R),6(S)-[1(R)-hydroxyethyl]-3-[4-((3-sulphamoyl-propyl)carbamoyl)phenoxy]-7-oxo-4-thia-1-azabicyclo[3.2.0]hept-2-ene-2-carboxylate 98 mg of the title compound were obtained by a procedure analogous to that described in Example 96 using 200 mg of 4-nitrobenzyl 5(R),3-(4-carboxyphenoxy)-6(S)-[1(R)-hydroxyethyl]-7-oxo-4-thia-1-azabicyclo[3.2.0]hept-2-ene-2-carboxylate, 154 mg of 1-hydroxybenzotriazole hydrate, 158 mg of 1-(3-dimethylaminopropyl)-3-ethylcarbodiimide hydrochloride, 512 μl of triethylamine and 98 mg of 3-sulphamoylpropylamine hydrochloride.

$\nu_{max}$ (CDCl$_3$) 1785 cm$^{-1}$.

δ (DMSO-d$_6$) 1.16 (3H, d, J=6.4 Hz); 3.05 (2H, m); 3.60 (2H, m); 3.75 (2H, m); 3.92 (1H, dd, J=1.5 and 6.4 Hz) 4.05 (1H, m); 5.38 (3H, m); 5.78 (1H, d, J=1.5 Hz); 7.38,7.90 (4H, AA'BB', J=8.8 Hz); 7.59,8.18 (4H, AA'BB', 8.7 Hz); 8.65 (1H, m).

EXAMPLE 131

Potasium 5(R),6(S)-[1(R)-hydroxyethyl]-3-[4((3-sulphamoyl-propyl)carbamoyl)phenoxy]-7-oxo-4-thia-1-azabicyclo[3.2.0]hept-2-ene-2-carboxylate 57 mg of the title compound were obtained from 90 mg of the 4-nitrobenzyl carboxylate defined in Example 130 by a procedure analogous to that described in Example 99, using 50 mg of 10% palladium on charcoal, 5 ml of dioxane, 14.9 mg of potassium bicarbonate and 5 ml of water. δ (D$_2$O) 1.32 (3H, d, J=6.2 Hz); 2.18 (2H, m); 3.35 (2H, m); 3.58 (2H, m); 3.95 (1H, dd, J=1.2 and 6.2 Hz); 4.30 (1H, m); 5.68 (1H, d, J=1.2 Hz); 7.28,7.80 (4H, AA'BB' J=9.4 Hz).

EXAMPLE 132

S-(Pentafluorphenyl) 3-(acetoxy)thiobenzoate 14.1 ml of pyridine was added at room temperature to a mixture of 3-acetoxybenzoyl chloride (34.7 g) and pentafluorthiophenol (35.0 g) in 250 ml of acetonitrile. After an initial exotherm stirring was continued for 1 hour and the solution evaporated to small volume and extracted with ethyl acetate. The organic extracts were washed with dilute hydorchloric acid, water, brine, dried over anhydrous magnesium sulphate and the filtered solution evaporated to give the desired thioester (63.3 g).

δ (CDCl$_3$) 2.33 (3H, s); 7.26–8.09 (4H, m).

EXAMPLE 133

S-(Pentalfuorphenyl) 3-(hydroxy)thiobenzoate 54.1 g of the title compound was prepared from 63 g of S-(pentafluorphenyl) 3-(acetoxy)thiobenzoate by a procedure analogous to that described in Example 9.

δ (d$_6$-acetone) 7.13–7.76 (4H, m); 9.03 (1H, br.s).

EXAMPLE 134

S-(Pentafluorophenyl) 3-(chlorothiocarbonyloxy)thiobenzoate

A solution of 187 mg of sodium hydroxide in 5 ml of water was added to a stirred suspension of S-(pentafluorophenyl) 3-(hydroxy)thiobenzoate (1.0 g) in chloroform (10 ml) at −10° C. Thiophosgene (0.36 ml) was added and the solution stirred whilst being allowed to reach room temperature. The chloroform layer was separated, dried over anhydrous calcium chloride and evaporated to leave a reside which was chromatographed on silica gel using ethyl acetate/hexane mixtures as eluant to give 0.61 g of the title compound.

δ (CDCl$_3$) 7.25–8.18 (4H, m).

EXAMPLE 135

4-Nitrobenzyl 2-[3(S)-[1(R)-dimethyl-(2-methylprop-2-yl)silyloxyethyl]-4(R)-ethylthioazetidin-2-on-1-yl]-3-[3-(pentafluorophenylthio-(carbonyl))phenoxy]-3-trimethylacetylthiopropenoate 8.07 g of the title compound were obtained by a process analogous to that described in Example 25 using 5.83 g of 4-nitrobenzyl 2-[3(S)-[1(R)-dimethyl-(2-methylprop-2-yl)silyloxyethyl]-4(R)-ethylthioazetidin-2-on-1-yl]acetate, 5.30 g of S-(pentaflurophenyl)-3-(chlorothiocarbonyloxy)thiobenzoate, 7.65 ml of hexamethyldisilazane, 36.2 mM of n-butyllithium and 3.21 ml of trimethylacetyl bromide.

δ (CDCl$_3$) 0.02,0.03 (6H, 2s); 0.82,0.87 (9H, 2s); 1.24,1.27 (9H, 2s); 1.04–1.39 (6H, m); 2.52–2.86 (2H, m); 3.22–3.25 (1H, m); 4.20–4.38 (1H, m); 5.24–5.44 (3H, m); 7.26–8.25 (8H, m).

EXAMPLE 136

4-Nitrobenzyl 2-[4(R)-ethylthio-3(S)-[1(R)-hydroxyethyl]azetidin-2-on-1-yl]-3-[3-(pentafluorophenylthio-(carbonyl))-phenoxy]-3-trimethylacetylthiopropenoate 3.18 g of the above compound were obtained from 8.07 g of the corresponding [1(R)-dimethyl-2-methyl-prop-2-yl)silyloxyethyl]compound (see Example 135) by a procedure analogous to that described in Example 33 using 14 ml of water and 14 ml of concentrated hydrochloric acid.

$\nu_{max}$ (CDCl$_3$) 1764 cm$^{-1}$. δ (CDCl$_3$) 1.06,1.13 (9H, 2s); 1.27 (3H, t, J=7.6 Hz); 1.31 (3H, d, J=6.2 Hz); 1.59 (1H, br.s) 2.62–2.84 (2H, m); 3.28 (1H, dd, J=2.7 Hz and 4.9 Hz); 4.20–4.36 (1H, m); 5.30 (2H, d, J=2.7 Hz); 5.29,5.38 (2H, ABq, J=13.5 Hz); 7.26–8.26 (8H, m).

EXAMPLE 137

4-Nitrobenzyl 2-[4(S)-chloro-3(S)-]1(R)-hydroxyethyl]azetidin-2-on-1-yl]-3-[3-(pentafluorophenylthio-(carbonyl))phenoxy]-3-trimethylacetylthiopropenoate 1.18 g of the above compound was obtained by a procedure analogous to that described in Example 41 using 3.17 g of the 1(R)-hydroxyethylazetidinone derivative defined in Example 136 and a solution of 6.95 mmol of chlorine in carbon tetrachloride.

δ (CDCl$_3$) 1.06 (9H, s); 1.40 (3H, d, J=6.3 Hz); 1.58 (1H, broad s); 3.55 (1H, dd, J=4.3 Hz and 9.5 Hz); 4.26–4.42 (1H, m); 5.32 (2H, apparent s); 6.18 (1H, d, J=4.3 Hz); 7.26–8.27 (8H, m).

EXAMPLE 138

4-Nitrobenzyl 5(R),6(S)-[1(R)-hydroxyethyl]-7-oxo-3-[3-(pentafluorophenylthio-(carbonyl))phenoxy]-4thia-1-azabicyclo[3.2.0]hept-2-ene-2-carboxylate 61 μl of pyridine was added to a stirred solution of 300 mg of 4-nitrobenzyl 2-[4(S)-chloro-3(S)-[1(R)-hydroxyethyl]azetidin-2-on-1-yl]-3-[3-(pentafluorophenylthio-(carbonyl))phenoxy]-3-trimethylacetylthiopropenoate in tetrahydrofuran-water (9:1 v/v) at room temperature. Stirring was continued for 2 hours and the mixture partitioned between ethyl acetate and water. The organic layer was washed with water, brine, and dried over anhydrous magnesium sulphate. Evaporation of the filtered solution gave a residue which was chromatographed on silica gel using hexane/ethyl acetate mixtures as eluant to afford 160 mg of the title compound as a yellow foam.

δ (CDCl$_3$) 1.38 (3H, d, J=6.3 Hz); 1.58 (1H, br.s); 3.81 (1H, dd, J=1.2 Hz and 6.6 Hz); 4.23–4.37 (1H, m); 5.24,5.44 (2H, ABq, J=13.8 Hz); 5.70 (1H, d, J=1.2 Hz); 7.43–8.21 (8H, m).

EXAMPLE 139

4-Nitrobenzyl 5(R),6(S)-[1(R)-hydroxyethyl]-3-[3-(2-(4-nitrobenzyloxycarbonylamino)ethyl)carbamoylphenoxy]-7-oxo-4-thia-1-azabicyclo[3.2.0]hept-2-ene-2-carboxylate 86 mg of the above compound were obtained by a procedure ananlogous to that described in Example 71D using 150 mg of 4-nitrobenzyl 5(R),6(S)-[1(R)-hydroxyethyl]-7-oxo-3-[3-(pentafluorophenylthio-(carbonyl))phenoxy]-4-thia-1-azabicyclo[3.2.0]hept-2-ene-2-carboxylate, 124 mg of 2-(4-nitrobenzyloxycarbonylamino)ethylamine hydrochloride and 69 μl of triethylamine in acetonitrile. The mixture was stirred until reaction was complete, ethyl acetate added and the organic solution washed successively with water and brine, and dried over magnesium sulphate. The filtered solution was evaporated to dryness and the residue chromatographed on silica gel using ethyl acetate/hexane mixtures as eluants to afford the title compound.

$\nu_{max}$ (CDCl$_3$) 1786, 1720 cm$^{-1}$.

δ (CDCl$_3$) 1.36 (3H, d, J=6.3 Hz); 3.42–3.66 (4H, m); 3.79 (1H, dd, J=1.4 and 6.6 Hz); 4.20–4.31 (1H, m); 5.19 (2H, s); 5.22,5.42 (2H, ABq, J=13.8 Hz); 5.68 (1H, d, J=1.4 Hz); 7.03 (1H, broad s); 7.20–8.22 (12H, m).

EXAMPLE 140

5(R), 3-[3-(2-aminoethyl)carbamoylphenoxy]-6(S)-[1(R)-hydroxyethyl]-7-oxo-4-thia-1-azabicyclo[3.2.0]hept-2-ene-2-carboxylic acid A mixture of 83.4 mg of the 4-nitrobenzyl carboxylate defined in Example 139, 23.6 mg of potassium bicarbonate, 160 mg of 10% palladium on charcoal, 8 ml of water and 8 ml of ethyl acetate was hydrogenated in a Parr apparatus at about 345 kPa (50 psi) for 1 hour. Acetic acid (1 ml) was added to the mixture, the aqueous layer separated, filtered and lyophilised to afford the title compound (together with one equivalent of potassium acetate) as a pale yellow solid (50 mg).

$\nu_{max}$ (KBr) 1764 cm$^{-1}$.

δ (D$_2$O) 1.29 (3H, d, J=6.4 Hz); 3.21–3.31 (2H, m); 3.64–3.77 (2H, m); 3.93 (1H, dd, 1.3 and 6.1 Hz); 4.18–4.30 (1H, m); 5.69 (1H, d, J=1.3 Hz); 7.06–7.68 (4H, m).

EXAMPLE 141

4-Nitrobenzyl 5(R),3-[4-((2-dimethylaminoethyl)carbamoyl)phenoxy]-6(S)-[1(R)-hydroxyethyl]-7-oxo-4-thia-1-azabicyclo[3.2.0]hept-2-ene-2-carboxylate 54 μl of N,N-dimethylethylenediamine was added dropwise to a stirred solution of 150 mg of 4-nitrobenzyl 5(R),3-[4-(4-chlorophenylthio-(carbonyl))phenoxy]-6(S)-[1(R)-hydroxyethyl]-7-oxo-4-thia-1-azabicyclo[3.2.0]hept-2-ene-2-carboxylate and 94 mg of silver trifluoromethanesulphonate in dry dimethylformamide at room temperature. When the reaction was complete the mixture was filtered and the filtrate taken up in ethyl acetate, washed with water, dried over anhydrous magnesium sulphate and evaporated in vacuo. Chromatography of the residue over silica gel using hexane-ethyl acetate mixtures as eluant gave the title compound as a pale yellow solid (58 mg).

$\nu_{max}$ (film) 1786 cm$^{-1}$.

δ (CDCl$_3$) 1.38 (3H, d, J=7.2 Hz); 2.30 (6H, s); 2.46–2.62 (2H, m); 3.44–3.62 (2H, m); 3.78 (1H, dd, J=1.2 and 5.7 Hz); 4.42–4.31 (1H, m); 5.23,5.43 (2H, ABq, J=13.7 Hz); 5.65 (1H, d, J=1.2 Hz); 6.96 (1H, broad s); 7.17,7.82 (4H, AA'BB', J=8.6 Hz); 7.54,8.18 (4H, AA'BB', J=8.6 Hz).

EXAMPLE 142

Potassium 5(R),3-[4-((2-dimethylaminoethyl)carbamoyl)phenoxy]-6(S)-[1(R)-hydroxyethyl]-7-oxo-4-thia-1-azabicyclo[3.2.0]hept-2-ene-2-carboxylate 31 mg of the above compound were obtained from 48 mg of the corresponding 4-nitrobenzyl carboxylate defined in Example 141 by a procedure analogous to that described in Example 58, using 8.6 mg of potassium bicarbonate.

δ (D$_2$O) 1.27 (3H, d, J=6.2 Hz); 2.60 (6H, s); 2.94–3.08 (2H, m); 3.54–3.72 (2H, m); 3.93 (1H, dd, J=1 and 5.6 Hz); 4.16–4.26 (1H, m); 5.68 (1H, d, J=1); 7.28,7.79 (4H, AA'BB', J=8.5 Hz).

EXAMPLE 143

4-Nitrobenzyl 5(R),6(S)-[1(R)-acetoxyethyl]-3-[4-(pentafluorophenoxycarbonyl)phenoxy]-7-oxo-4-thia-1-azabicyclo[3.2.0]hept-2-ene-2-carboxylate 412 μl of acetic anhydride was added to a stirred solution of 570 mg of 4-nitrobenzyl 5(R),3-[4-(pentafluorophenoxycarbonyl)phenoxy]-6(S)-[1(R)-hydroxyethyl]-7-oxo-4-thia-1-azabicyclo[3.2.0]hept-2-ene-2-carboxylate and 10 mg of 4-dimethylaminopyridine in 15 ml of dry tetrahydrofuran. The mixture was stirred until reaction was complete, solvents evaporated in vacuo and the residue partitioned between ethyl acetate and water. The organic layer was separated, washed with saturated sodium bicarbonate solution, water and brine and dried over anhydrous magnesium sulphate. Evaporation of the filtered solution gave a residue which was chromatographed on deactivated silica gel using hexane/ethyl acetate mixtures as eluant to afford 292 mg of the title compound.

ν$_{max}$ (CDCl$_3$) 1793,1755 cm$^{-1}$

δ (CDCl$_3$) 1.44 (3H, d, J=6.4 Hz); 2.07 (3H, s); 3.97 (1H, dd, J=7.7 and 1.6 Hz); 5.21–5.42 (1H, m); 5.24,5.39 (2H, ABq, J=13.7 Hz); 5.70 (1H, d, J=1.6 Hz); 7.27,8.20 (4H, AA'BB', J=8.8 Hz); 7.53,8.22 (4H, AA'BB', J=8.7 Hz).

EXAMPLE 144

4-Nitrobenzyl 5(R),6(S)-[1(R)-acetoxyethyl]-3-[4-(carbamoylmethyl)carbamoylphenoxy]-7-oxo-4-thia-1-azabicyclo[3.2.0]hept-2-ene-2-carboxylate 33 μl of triethylamine was added to a stirred solution of 138 mg of the 4-nitrobenzyl carboxylate defined in Example 143 and 26 mg of glycinamide hydrochloride in 5 ml of dry dimethylformamide. Stirring was continued at room temperature until the reaction was complete as judged by t.l.c. The mixture was partitioned between ethyl acetate and water and the organic layer separated and the aqueous layer extracted with further portions of ethyl acetate. The combined organic layers were washed with water and brine and dried over anhydrous magnesium sulphate. Evaporation of the filtered solution and chromatography of the residue on silica gel using hexane/ethyl acetate/methanol mixture as eluant gave 78 mg of the title amide as a pale yellow solid.

δ (CD$_3$CN) 1.33 (3H, d, J=6.4 Hz); 2.17 (3H, s); 3.92 (2H, d, J=5.7 Hz); 4.06 (1H, dd, J=6.0 and 1.6 Hz); 5.17–5.33 (1H, m); 5.25,5.35 (2H, ABq, J=13.2 Hz); 5.75 (1H, d, J=1.6 Hz); 5.79 (1H, br.s); 6.38 (1H, br.s); 7.26,7.85 (4H, AA'BB', J=8.9 Hz); 7.38 (1H, br.t, J=5.7 Hz); 7.53,8.15 (4H, AA'BB', J=8.8 Hz).

EXAMPLE 145

Potassium 5(R),6(S)-[1(R)-acetoxyethyl]-3-[4-(carbamoylmethyl)carbamoyl-phenoxy]-7-oxo-4-thia-azabicyclo[3.2.0]hept-2-ene-2-carboxylate 42 mg of the above compound was prepared by a procedure analogous to that described in Example 58 using 76 mg of the 4-nitrobenzyl carboxylate defined in Example 144, 76 mg of 10% palladium on charcoal catalyst, 13.4 mg of potassium bicarbonate, 10 ml of ethyl acetate and 10 ml of water.

ν$_{max}$ (KBr disc) 1775,1735 cm$^{-1}$.

δ (D$_2$O) 1.29 (3H, d, J=6.5 Hz); 2.04 (3H, s); 4.01 (2H, s); 4.11 (1H, dd, J=5.4 and 1.3 Hz); 5.15–5.25 (1H, m); 5.70 (1H, d, J=1.3 Hz); 7.25,7.80 (4H, AA'BB', J=8.8 Hz).

We claim:

1. A compound of formula I

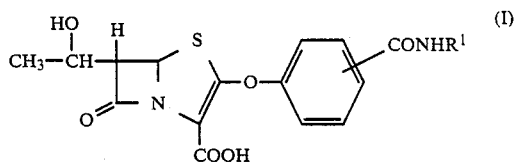

in which R$^1$ represents a straight or branched chain alkyl group having from 1 to 5 carbon atoms, which alkyl group is substituted by one or more substituents selected from (i) unsubstituted phenyl groups;
(ii) heterocyclic groups having 5 or 6 ring members and 1 nitrogen atom;
(iii) —CN groups;
(iv) guanidino and formimidoylamino groups;
(v) —OR$_a{}^2$ and —SR$_a{}^2$ groups in which R$_a{}^2$ represents a hydrogen atom or an alkyl group having 1 to 4 carbon atoms, especially a methyl or ethyl group;
(vi) —COOR$_b{}^2$ groups in which R$_b{}^2$ represents a hydrogen atom or a carboxy protecting group;
(vii) —SO$_2$N(R$_a{}^2$)$_2$ groups in which R$_a{}^2$ is as defined above,
(viii) —SO$_2$R$_c{}^2$ and —SOR$_c{}^2$ groups, in which R$_c{}^2$ represents an alkyl group having from 1 to 4 carbon atoms;
(ix) —N(R$_a{}^2$)$_2$ in which R$_a{}^2$ is as defined above;
(x) —OCON(R$_a{}^2$)$_2$ and —NHCON(R$_a{}^2$)$_2$ groups, in which R$_a{}^2$ is as defined above;
(xi) —NHCOR$_a{}^2$, and —CONHOR$_a{}^2$ groups, in which R$_a{}^2$ is as defined above;
(xii) —NHCOOR$_d{}^2$ and —NH—Q—COOR$_a{}^2$ groups in which R$_a{}^2$ is as defined above, R$_d{}^2$ represents a carboxy protecting group, and Q represents a methylene group which may be substituted by a methyl group or a phenyl group, or Q represents a straight or branched chain alkylene group having two or three carbon atoms which may be substituted by one or two substituents selected from amino, methyl and phenyl groups;
(xiii) —CON(R$_a{}^2$)$_2$ groups in which R$_a{}^2$ is as defined above;
(xiv) groups of the formula

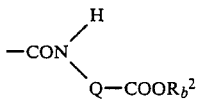

in which Q and $R_b^2$ are as defined above; and
(xv) groups of the formula

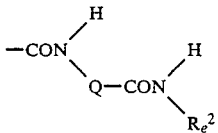

in which Q is as defined above and $R_e^2$ represents a hydrogen atom, an alkyl group having from 1 to 4 carbon atoms or a group

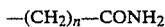

in which n is an integer of from 1 to 4; or $R^1$ represents an amidino group which may be unsubstituted or substituted by one, two or three groups, which may be the same or different, selected from methyl and ethyl groups; and esters thereof, which esters can be converted into the free acid by hydrolysis, photolysis, reduction or esterase enzyme action, at the 2-carboxy group or at the 8-hydroxy group or both; and physiologically tolerable salts thereof.

2. An ester as claimed in claim 1, wherein an esterified carboxy group at position 2 is a —$COOR_y$ group, in which $R_y$ represents a methyl or ethyl group which is substituted by an acyloxy group selected from the group consisting of acetoxymethyl, 1-(acetoxy)ethyl, pivaloyloxymethyl and 5-methyldioxalene-2-on-4-yl, by an aminoalkanoyloxy group, by an unsubstituted or substituted 2-aminoethyl group, or represents a methyl group substituted by one or more unsubstituted or substituted phenyl groups which $CO_2R_y$ group can be converted by hydrolysis, by photolysis, by reduction or by esterase enzyme action to give the corresponding free acid or salt thereof.

3. An ester as claimed in claim 1, wherein a methyl group is substituted by one phenyl group which is unsubstituted or is substituted by one or more substituents selected from nitro groups and F, Cl, Br atoms.

4. An ester as claimed in claim 1, which is an acyloxymethyl or 1'-(acyloxy)ethyl ester, a 5-methyldioxalen-2-on-4-yl-methyl ester, an aminoalkanoyloxymethyl ester, a phthalidyl ester, a 1'-(alkoxycarbonyloxy)ethyl ester, or a 2-aminoethyl ester, a glycyloxymethyl, L-valyloxymethyl, L-leucyloxymethyl, 1'-(methoxycarbonyloxy)ethyl, 2-diethyl-aminoethyl or 2-(1-morpholino)-ethyl ester, or a pivaloyloxymethyl, ethoxycarbonyloxymethyl, 5-methyldioxalen-2-on-4-yl-methyl, acetylmethyl, acetoxymethyl, 1'-(acetoxy)ethyl, 1'-(acetyl)ethyl or 1'-(ethoxycarbonyloxy)ethyl ester.

5. A compound as claimed in claim 1, wherein the ester group is removable by esterase enzyme action under physiological conditions to give the free acid or carboxylate salt.

6. A pharmaceutically acceptable salt of a compound as claimed in claim 1.

7. A compound as claimed in claim 1 having an esterified 8-hydroxy group, wherein the 8-ester group is removable under physiological conditions.

8. A compound I as claimed in claim 1, having R stereochemistry at position 5, S stereochemistry at position 6, and R stereochemistry at position 8.

9. A compound as claimed in claim 1 is selected from the group consisting of 5R,3-[3-(N-carbamoylmethyl)-carbamoyl)phenoxy]-6-S-(1R-hydroxyethyl)-7-oxo-4-thia-1-azabicyclo[3,2,0]hept-2-ene-2carboxylic acid, 5R,3-[4-(N-carbamoylmethyl)carbamoyl)phenoxy]-6S-(1R-hydroxyethyl)-7-oxo-4-thia-1-azabicyclo[3,2,0-]hept-2-ene-2-carboxylic acid, 5R,3-[4-(N-(N-(carbamoylmethyl)carbamoylmethyl)carbamoyl)phenoxy]-6S-(1R-hydroxyethyl)-7-oxo-4-thia-1-azabicyclo[3,2,0-]hept-2-ene-2-carboxylic acid, 5R,3-[4-(N-hydroxycarbamoyl)methylcarbamoyl)phenoxy]-6S-[1R-hydroxyethyl]-7-oxo-4-thia-1-azabicyclo[3,2,0]hept-2-ene-2-carboxylic acid, 5R,3-[4-((1-carbamoyl-2-hydroxyethyl)-carbamoyl)phenoxy]-6S-[1R-hydroxyethyl]-7-oxo-4-thia-1-azabicyclo[3,2,0]hept-2-ene-2-carboxylic acid, 5R,3-[4-((cyanomethyl)carbamoyl)phenoxy]-6S-[1R-hydroxyethyl]-7-oxo-4-thia-1-azabicyclo]3,2,0]-hept-2-ene-2-carboxylic acid, 5R,3-[4-((2-aminoethyl)carbamoyl)phenoxy]-6S-[1R-hydroxyethyl]-7-oxo-4-thia-1-azabiciyclo[3,2,0]hept-2-ene-2-carboxylic acid or an ester or salt of a compound of this group.

10. A pharmaceutical composition for the treatment of bacterial infections comprising a therapeutically effective amount of a compound as claimed in claim 1 or its physiologically tolerable salts in association with a pharmaceutically suitable carrier.

11. The method of using a compound as claimed in claim 1, for the manufacture of a medicament for the treatment of bacterial infections.

* * * * *